(12) United States Patent
Plückthun et al.

(10) Patent No.: US 6,815,540 B1
(45) Date of Patent: Nov. 9, 2004

(54) IMMUNOGLOBULIN SUPERFAMILY DOMAINS AND FRAGMENTS WITH INCREASED SOLUBILITY

(75) Inventors: Andreas Plückthun, Zürich (CH); Lars Nieba, Zürich (CH); Annemarie Honegger, Zürich (CH)

(73) Assignee: University of Zurich, Zurich (CH)

( * ) Notice: Subject to any disclaimer, the term of this patent is extended or adjusted under 35 U.S.C. 154(b) by 0 days.

(21) Appl. No.: 09/232,290

(22) Filed: Jan. 15, 1999

Related U.S. Application Data

(63) Continuation of application No. PCT/EP97/03792, filed on Jul. 16, 1997.

(30) Foreign Application Priority Data

Jul. 16, 1996 (EP) ............................................. 96111441

(51) Int. Cl.[7] .............................................. C07H 21/04
(52) U.S. Cl. ............................... 536/23.53; 435/320.1; 435/325; 435/326; 530/387.3
(58) Field of Search ................................ 435/69.1, 69.7, 435/752.3, 69.6, 320.1, 325, 326; 536/23.4, 23.5, 23.53; 530/387.3

(56) References Cited

U.S. PATENT DOCUMENTS 5,514,582 A * 5/1996 Capon et al.
6,485,943 B2 * 11/2002 Stevens et al.

FOREIGN PATENT DOCUMENTS

WO PCT WO 92 01787 2/1992

OTHER PUBLICATIONS

Nieba, Honnegar, Krebber and Pluckthun, Protein Engineering, 10(4):435–444, Apr. 1997.*
Knappik et al. Biotechniques 17(4):754–761, Oct. 1994.*
Kostelny et al The Journal of Immunology, 148:1547–1553, 1992.*
Dubel et al Journal of Immunological Methods 178:201–209, 1995.*
Hopp, T.P. et al., "A short polypeptide marker sequence useful for recombinant protein identification and purification", *BIO/TECHNOLOGY* 6, 1204–1210 (1988).
Muyldermans, S. et al., "Sequence and structure of Vh domain from naturally occurring camel heavy chain immunoglobulins lacking light chains", *Protein Engineering* 7(9), 1129–1135 (1994).
Jenkins, T.M. et al., "Catalytic domain of human immunodefiency virus type 1 integrase: Identification of a soluble mutant by systemic replacement of hydrophobic residues", *PNAS* 92, 6057–6061 (1995).
Breitling, F. et al., "A surface expression vector for antibody screening", *Gene* 104, 147–153 (1991).
Dale, J.E., et al., "Improving protein solubility through reationally designed amino acid replacements: solubilization of the trimethoprim resistant type S1 dihydrofolate reductase", *Protein Engineering* 7(7), 933–939 (1994).

* cited by examiner

*Primary Examiner*—Larry R. Helms
(74) *Attorney, Agent, or Firm*—Heller Ehrman White and McAuliffe LLP

(57) ABSTRACT

The present invention relates to the modification of immunoglobulin superfamily (IgSF) domains, IgSF fragments and fusion proteins thereof, especially to the modification of antibody derivatives, so as to improve their solubility, and hence the yield, and ease of handling. The inventors have found that this can be achieved by making the region which comprised the interface with domains adjoined to said IgSF domain in a larger fragment or a full IgSF protein, and which becomes exposed in the IgSF domain, more hydrophilic by modification. The present invention describes DNA sequences encoding modified IgSF domains or fragments and fusion proteins thereof, vectors and hosts containing these DNA sequences, IgSF domains or fragments or fusion proteins obtainable by expressing said DNA sequences in suitable expression systems, and a method for modifying IgSF domains, so as to improve their solubility, expressibility and ease of handling.

22 Claims, 28 Drawing Sheets

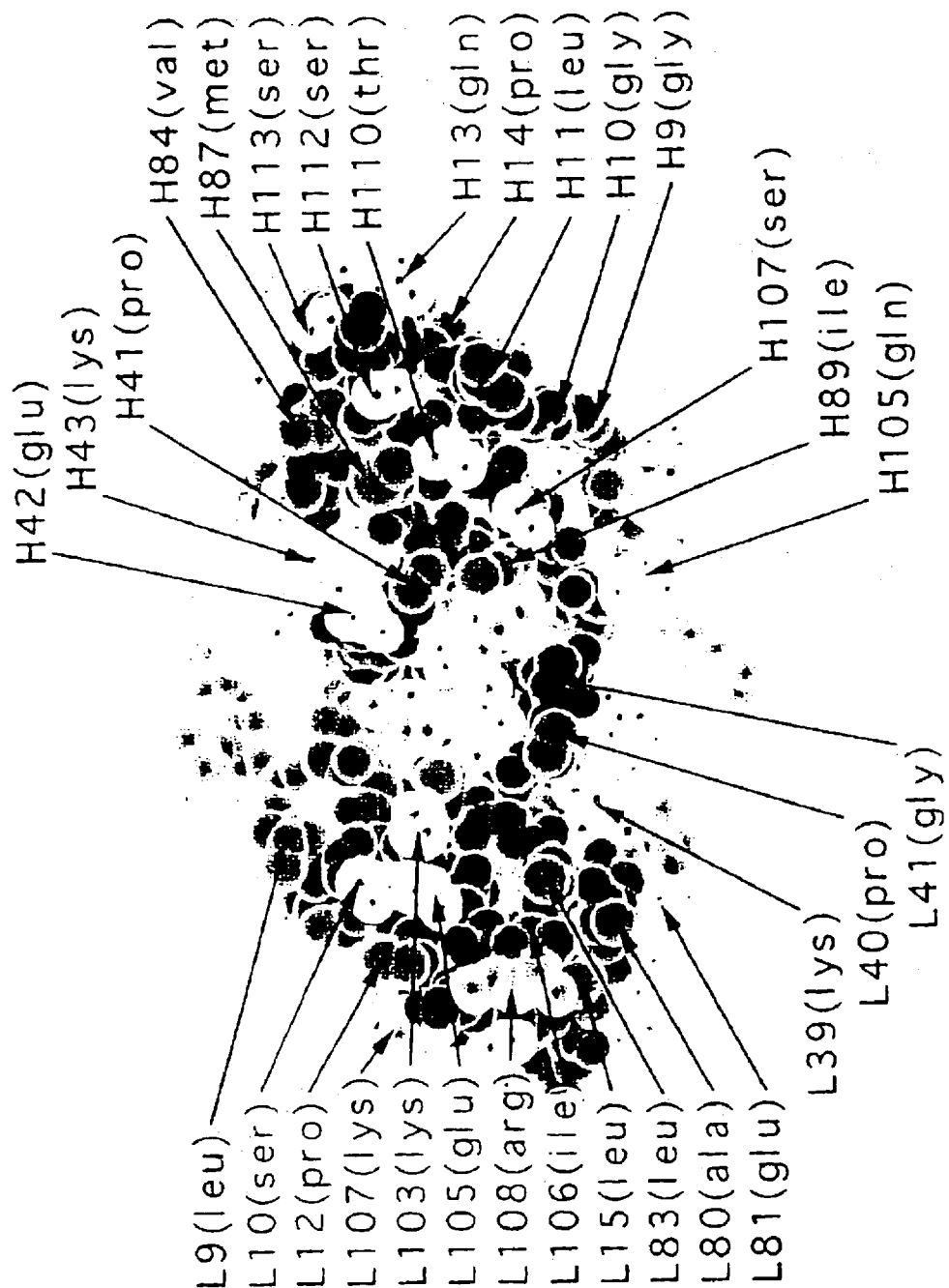
Figure 1: Space filling representation of the Fv fragment of the antibody 4-4-20

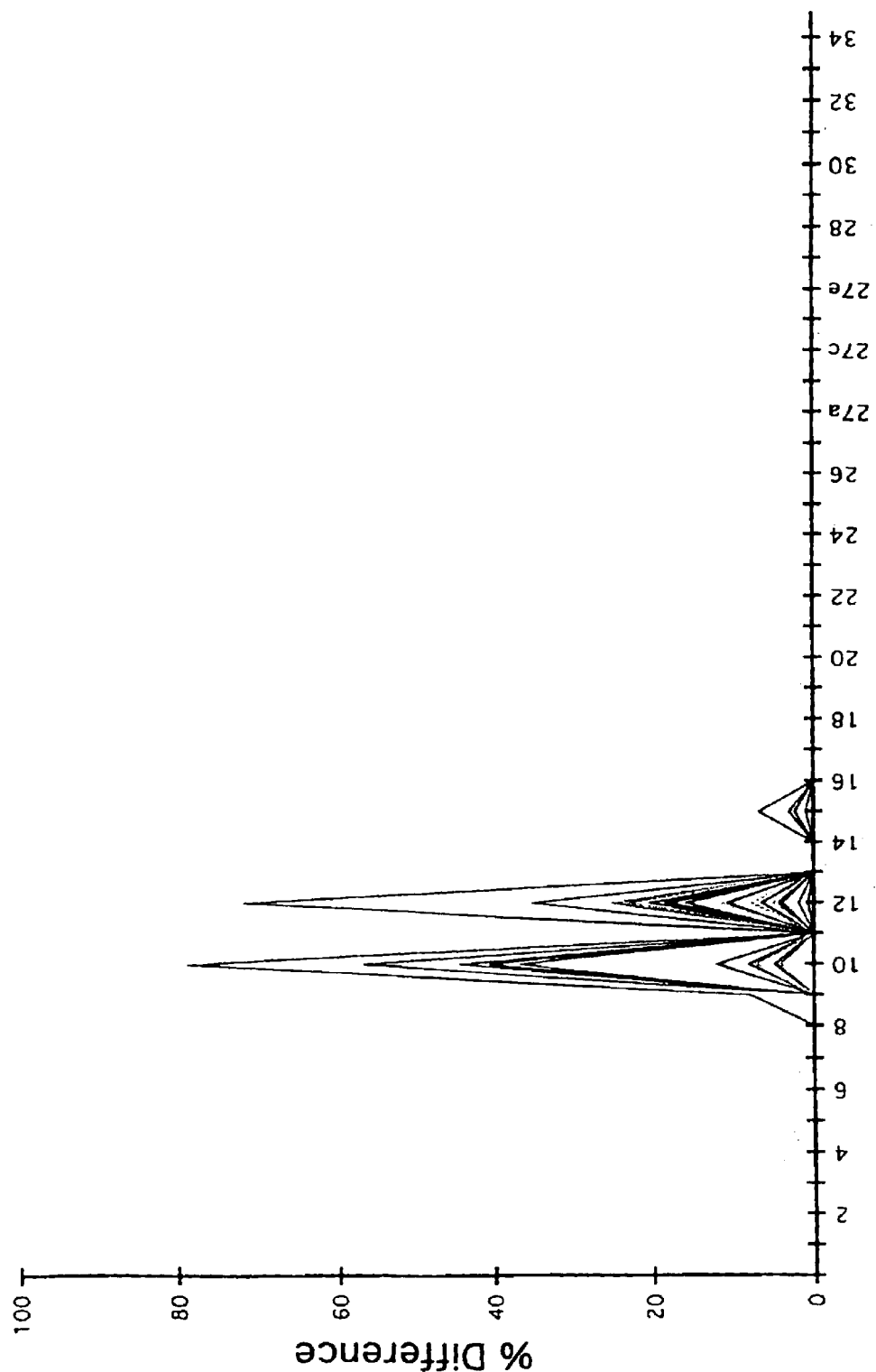
Figure 2a: Variable/constant domain interface residues for VL

Figure 2a: Variable/constant domain interface residues for VL (cont.)
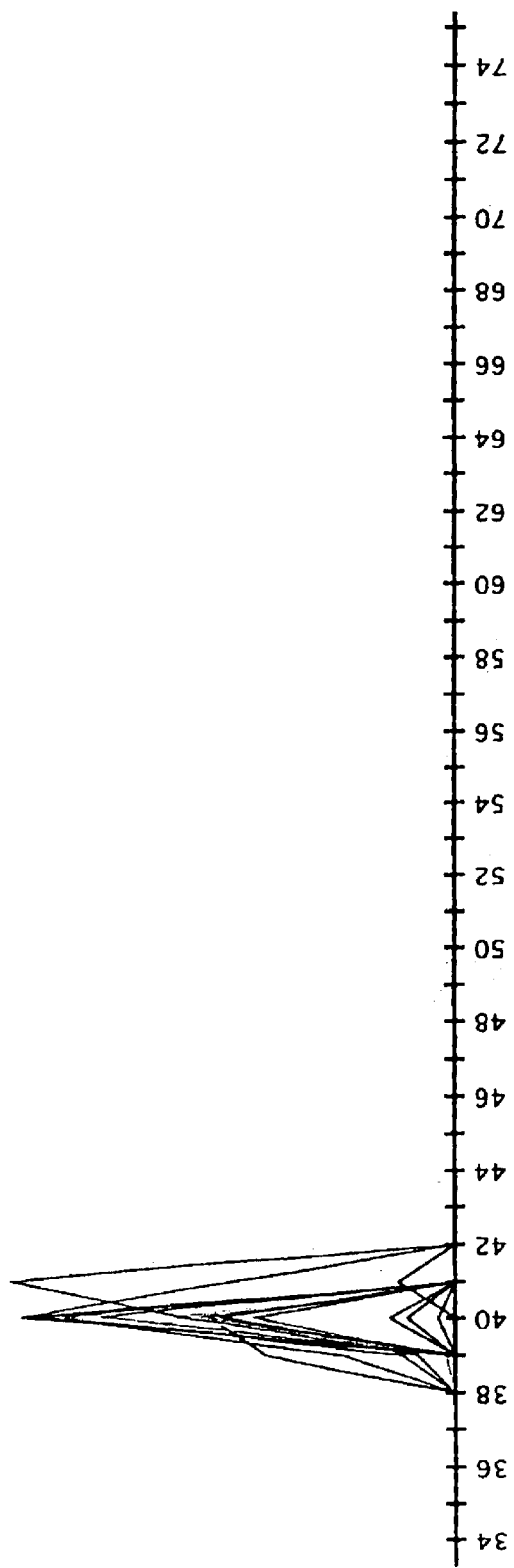

Figure 2a: Variable/constant domain interface residues for VL (cont.)
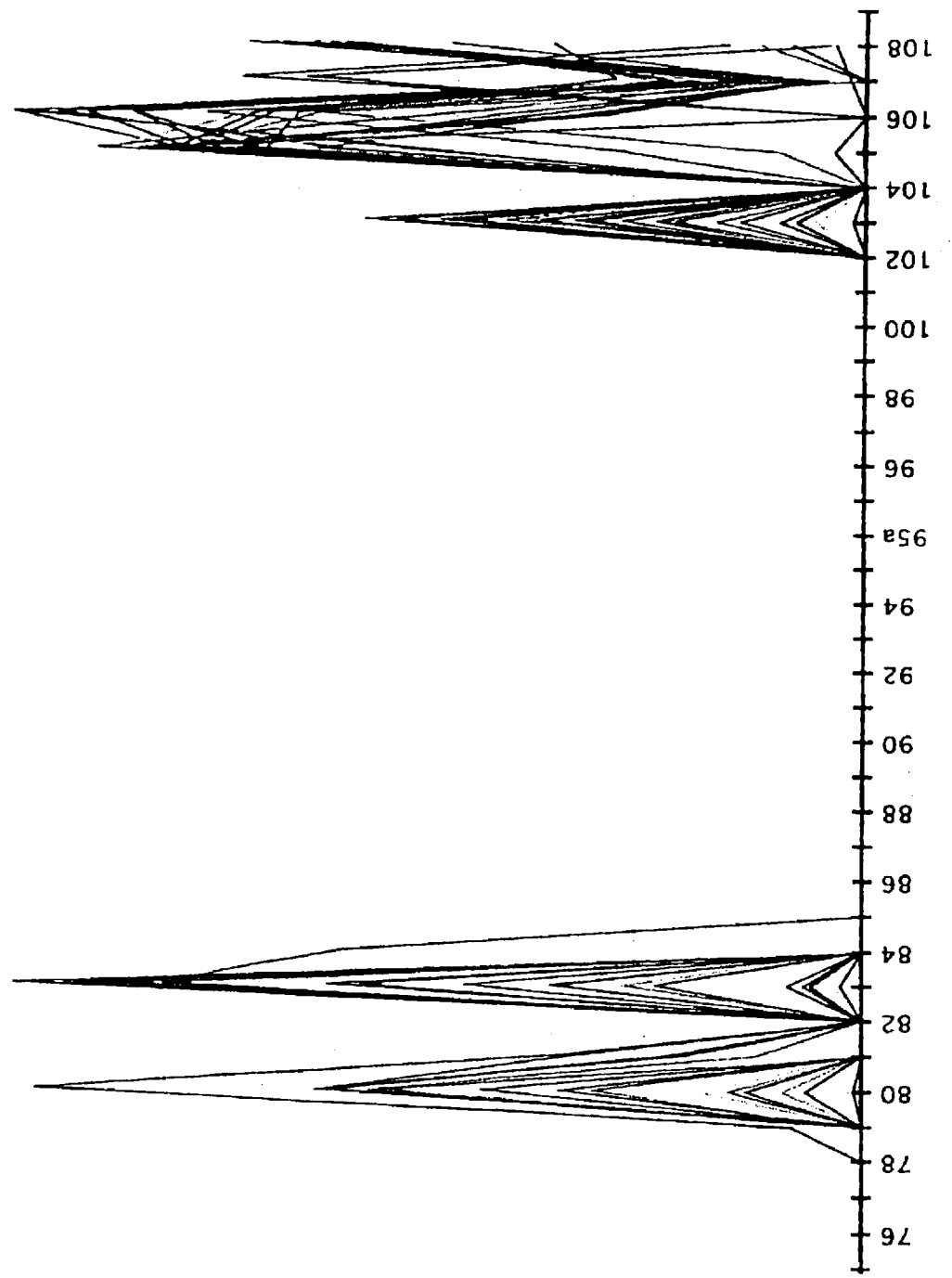

Figure 2a: Variable/constant domain interface residues for VL (cont.)

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 1acy | D | V | V | M | T | Q | S | P | A | S | L | V | V | S | L | G | Q | R | A | T | I | S |
| 1baf | Q | I | V | L | T | Q | S | P | A | - | M | S | A | S | P | G | E | K | V | T | M | T |
| 1bbj | D | I | V | M | T | Q | S | P | A | S | L | S | V | S | V | G | E | T | V | T | - | T |
| 1cbv | D | V | Q | M | T | Q | S | T | P | S | L | P | V | S | L | G | D | Q | A | S | - | S |
| 1dfb | D | V | V | M | T | Q | S | P | A | S | L | S | V | S | L | G | E | R | V | T | M | T |
| 1fdl | D | I | V | M | T | Q | S | P | A | T | L | S | V | T | L | G | E | T | V | T | - | T |
| 1fig | E | N | V | L | T | Q | S | P | S | S | M | S | A | S | L | G | E | K | V | T | M | A |
| 1frg | D | I | V | M | T | Q | S | P | A | S | L | L | T | S | A | G | D | R | V | S | - | S |
| 1fvd | D | I | V | M | T | Q | S | P | S | S | L | S | A | S | P | G | E | K | V | T | L | T |
| 1ggb | D | V | V | L | T | Q | T | P | G | S | L | A | V | S | L | G | Q | R | A | S | - | S |
| 1gig | Q | A | V | V | T | Q | E | - | S | A | L | T | G | S | L | G | E | T | V | T | - | S |
| 1hin | D | V | V | M | T | Q | S | P | S | S | L | T | V | T | P | G | D | Q | A | S | L | S |
| 1gi | A | V | V | L | T | Q | T | P | L | S | L | P | T | S | A | G | S | R | V | T | M | S |
| 1ind | D | L | V | M | T | Q | E | T | P | S | A | P | V | S | L | G | D | Q | A | S | - | S |
| 1jel | P | S | A | M | T | Q | S | P | K | L | M | P | S | N | - | - | - | - | - | - | - | - |
| 1mam | E | L | V | L | T | Q | - | - | L | - | L | S | V | G | - | G | D | R | A | T | - | S |
| 1mco | D | V | V | M | T | Q | - | P | P | S | L | P | V | T | L | G | D | S | A | T | - | S |
| 1nca | D | V | V | M | T | Q | T | P | A | - | M | S | A | S | P | G | D | Q | V | T | M | T |
| 2cgr | D | L | A | L | T | Q | S | P | A | S | T | S | G | S | - | G | D | R | V | S | - | S |
| 2dbl | D | L | V | M | T | Q | S | T | P | S | L | A | A | S | - | G | D | R | V | T | M | S |
| 2f19 | Q | I | V | M | T | Q | S | P | A | - | M | S | A | S | P | G | Q | K | V | T | L | T |
| 2fb4 | Q | L | V | L | T | Q | S | P | A | T | L | P | A | S | P | G | Q | K | V | T | - | S |
| 2fbj | D | V | V | M | T | Q | T | P | L | S | L | P | V | S | L | G | D | Q | A | S | M | T |
| 2hfl | D | V | L | M | T | Q | T | P | A | - | L | S | V | A | A | G | E | K | V | T | M | T |
| 2igf | D | V | V | M | T | Q | S | P | L | S | L | P | V | S | L | G | D | Q | A | S | L | S |
| 2mcp | D | V | V | L | T | Q | S | P | A | S | L | S | A | V | P | G | N | Q | V | T | - | S |
| 3hfm | D | V | V | M | T | Q | T | P | L | S | L | P | V | S | L | G | D | D | V | S | L | S |
| 4fab | D | V | V | M | T | Q | T | Q | - | - | V | P | A | S | A | G | D | R | V | S | - | S |
| 6fab | D | I | Q | M | T | Q | T | - | L | S | L | S | A | - | A | G | D | R | V | T | - | S |
| 8fab | E | L | T | Q | - | P | P | - | P | S | V | S | V | V | P | G | Q | T | A | R | I | T |

Figure 2a: Variable/constant domain interface residues for VL (cont.)

Figure 2a: Variable/constant domain interface residues for VL (cont.)

Figure 2a: Variable/constant domain interface residues for VL (cont.)

Figure 2a: Variable/constant domain interface residues for VL (cont.)

Figure 2a: Variable/constant domain interface residues for VL (cont.)

Figure 2b: Variable/constant domain interface residues for VH
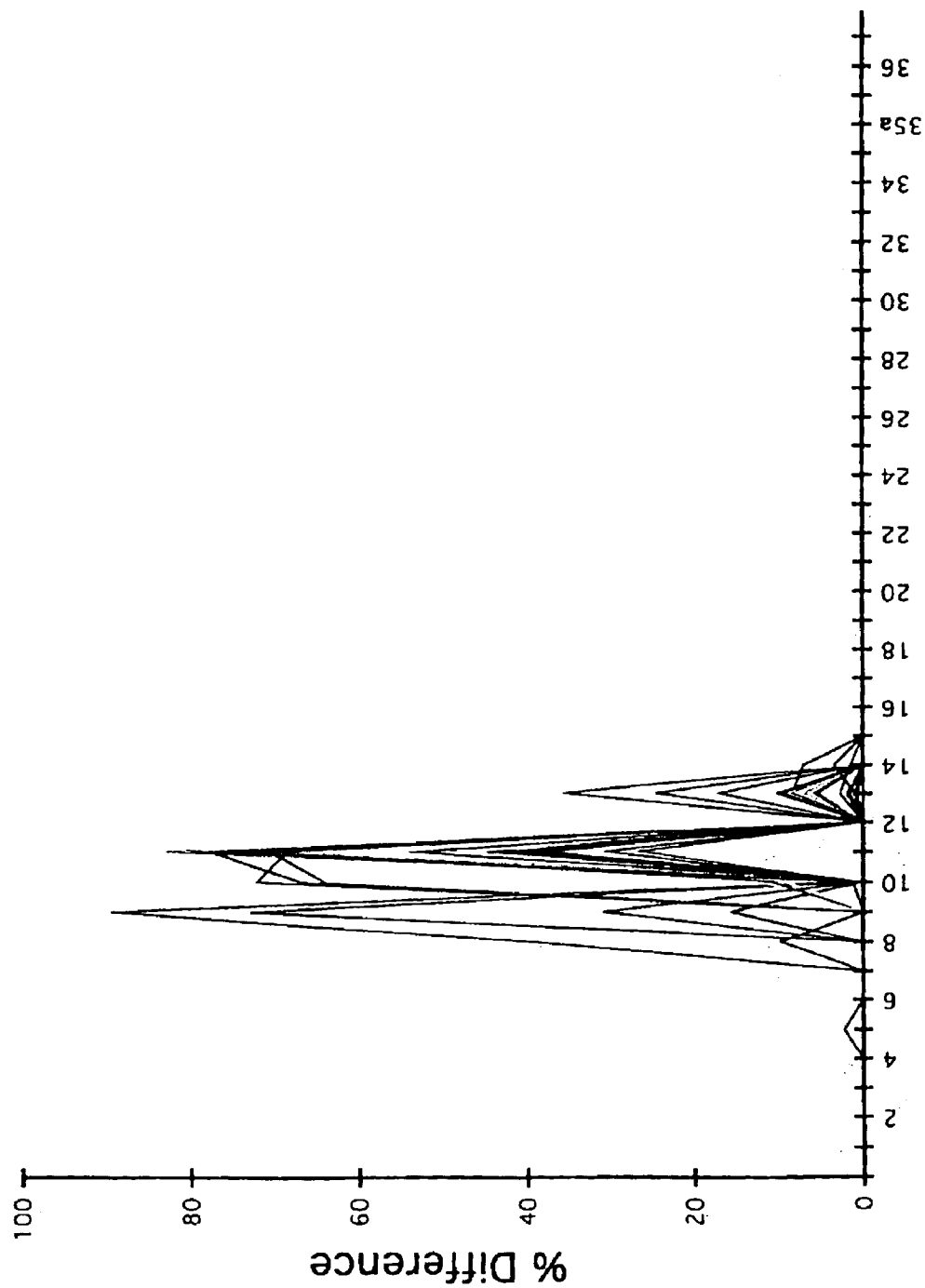

Figure 2b: Variable/constant domain interface residues for VH (cont.)
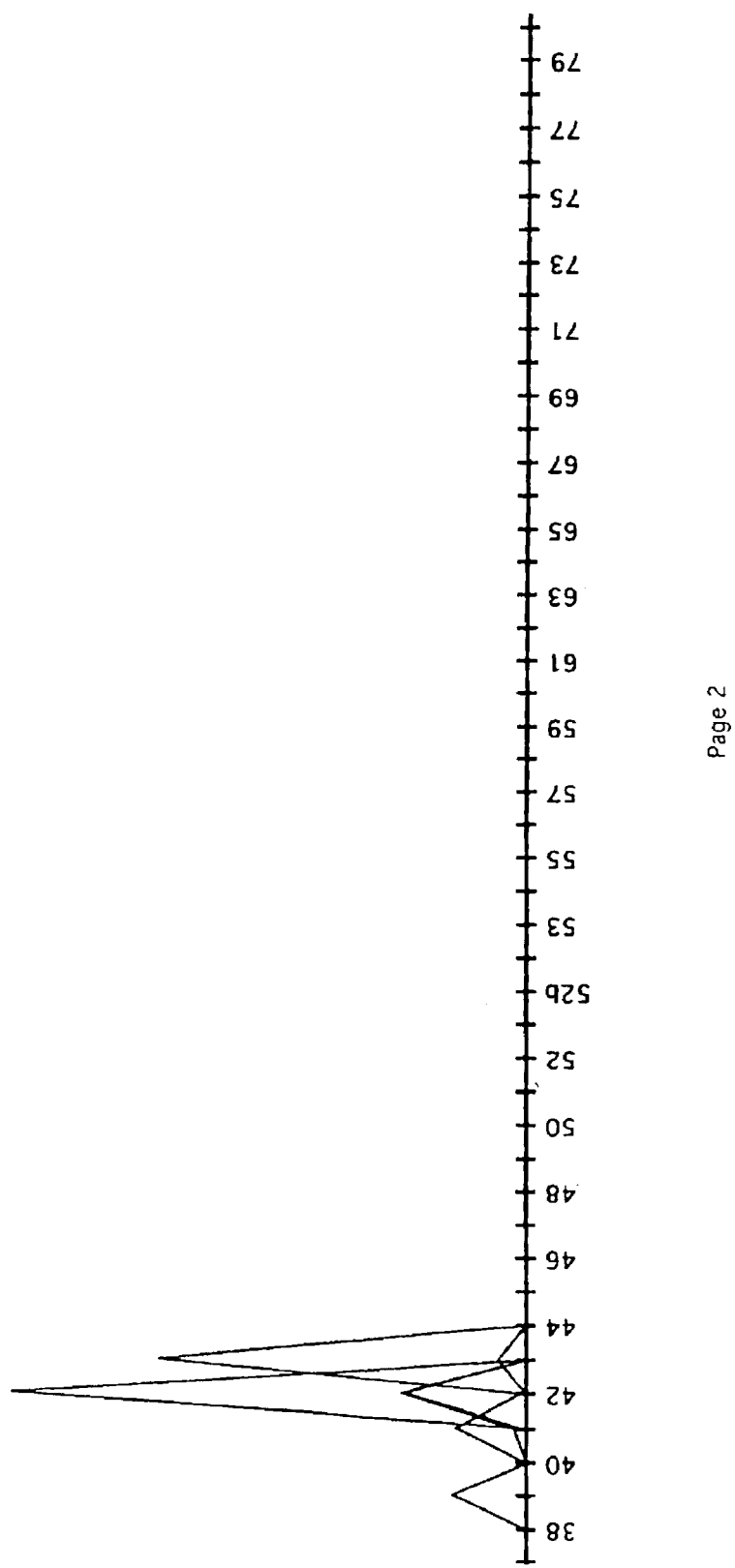

Figure 2b: Variable/constant domain interface residues for VH (cont.)
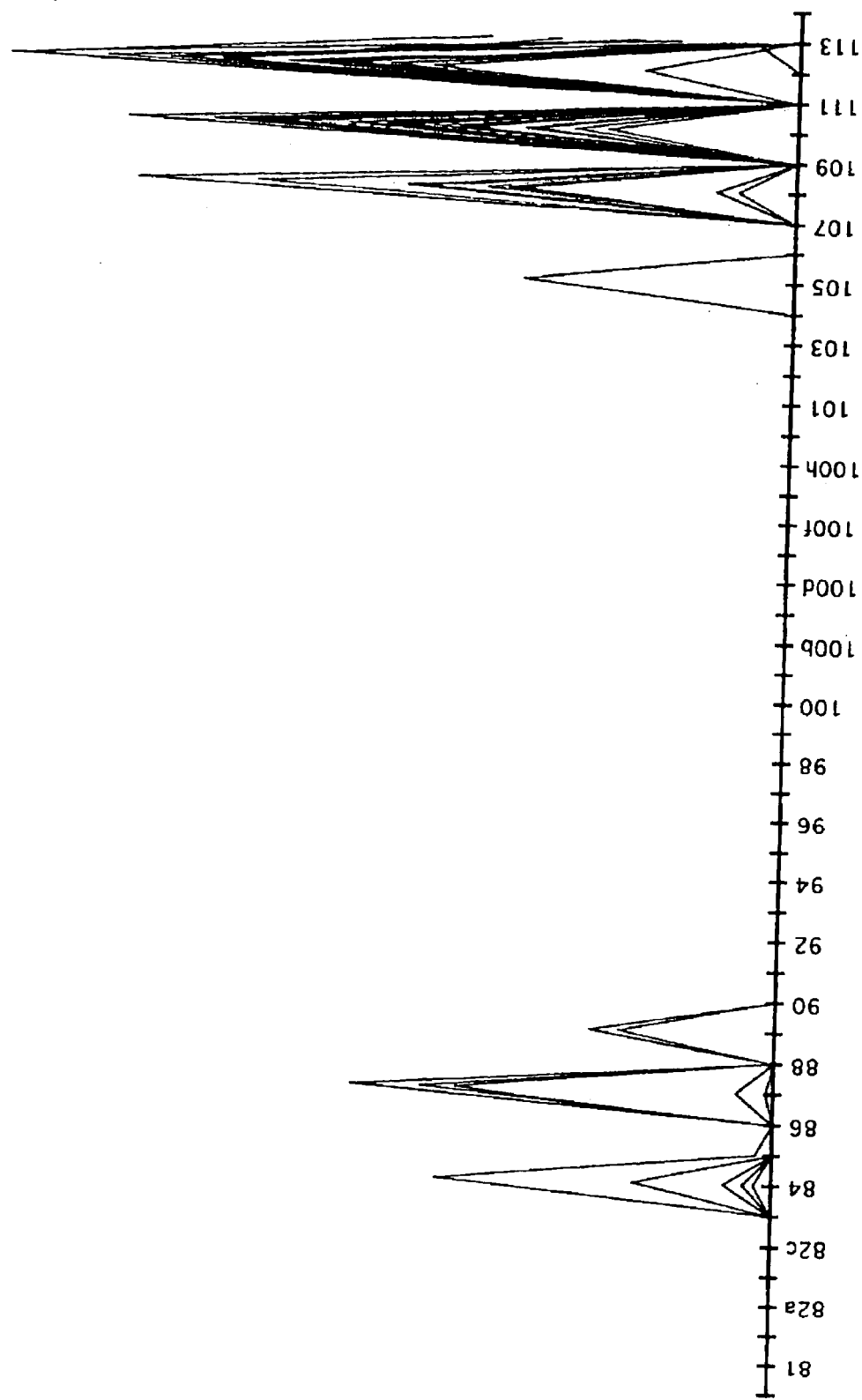

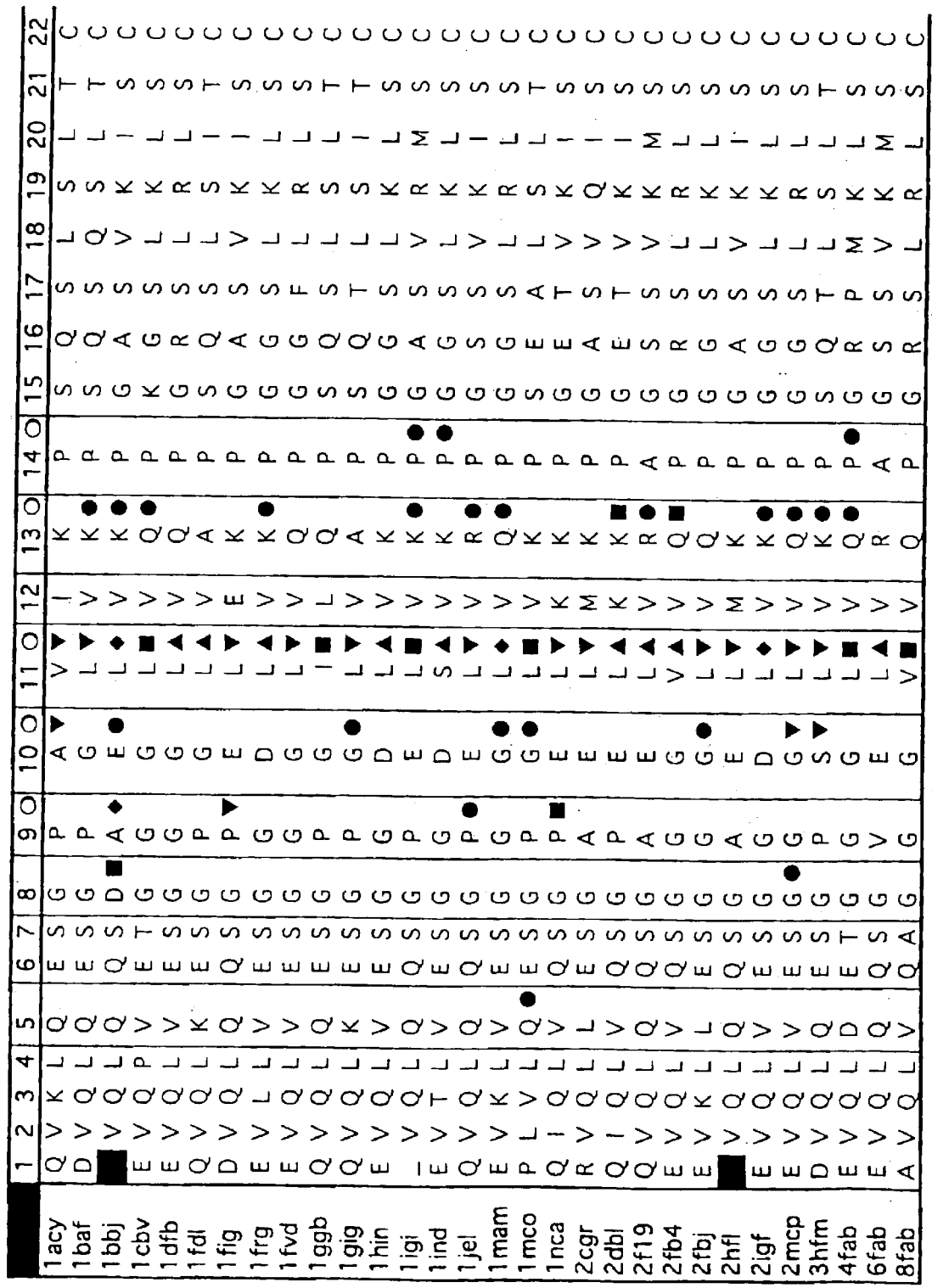
Figure 2b: Variable/constant domain interface residues for VH (cont.)

Figure 2b: Variable/constant domain interface residues for VH (cont.)

Figure 2b: Variable/constant domain interface residues for VH (cont.)

Figure 2b: Variable/constant domain interface residues for VH (cont.)

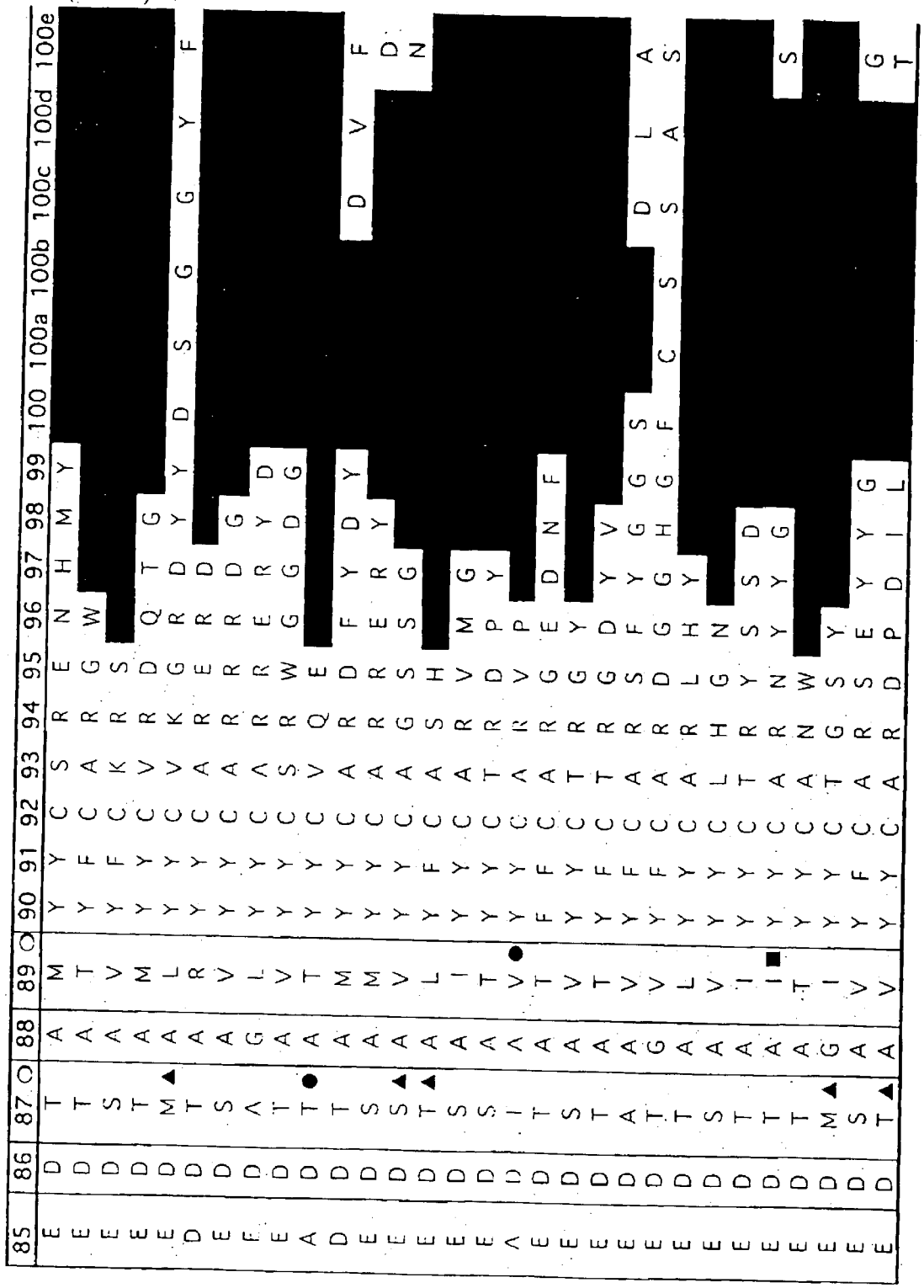
Figure 2b: Variable/constant domain interface residues for VH (cont.)

Figure 2b: Variable/constant domain interface residues for VH (cont.)
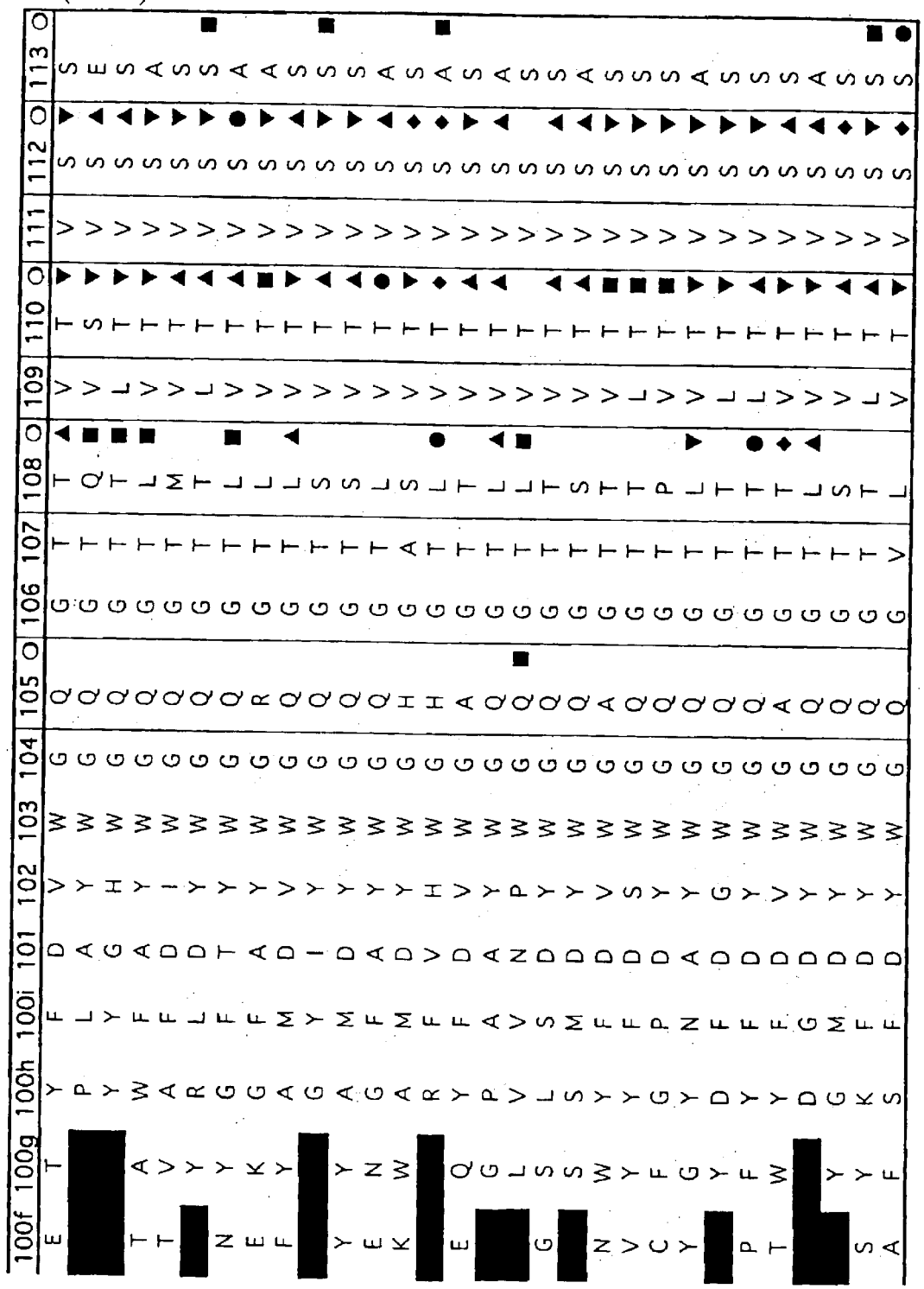

Figure 3: Western blots showing the insoluble (i) and soluble (s) fractions of cell extracts
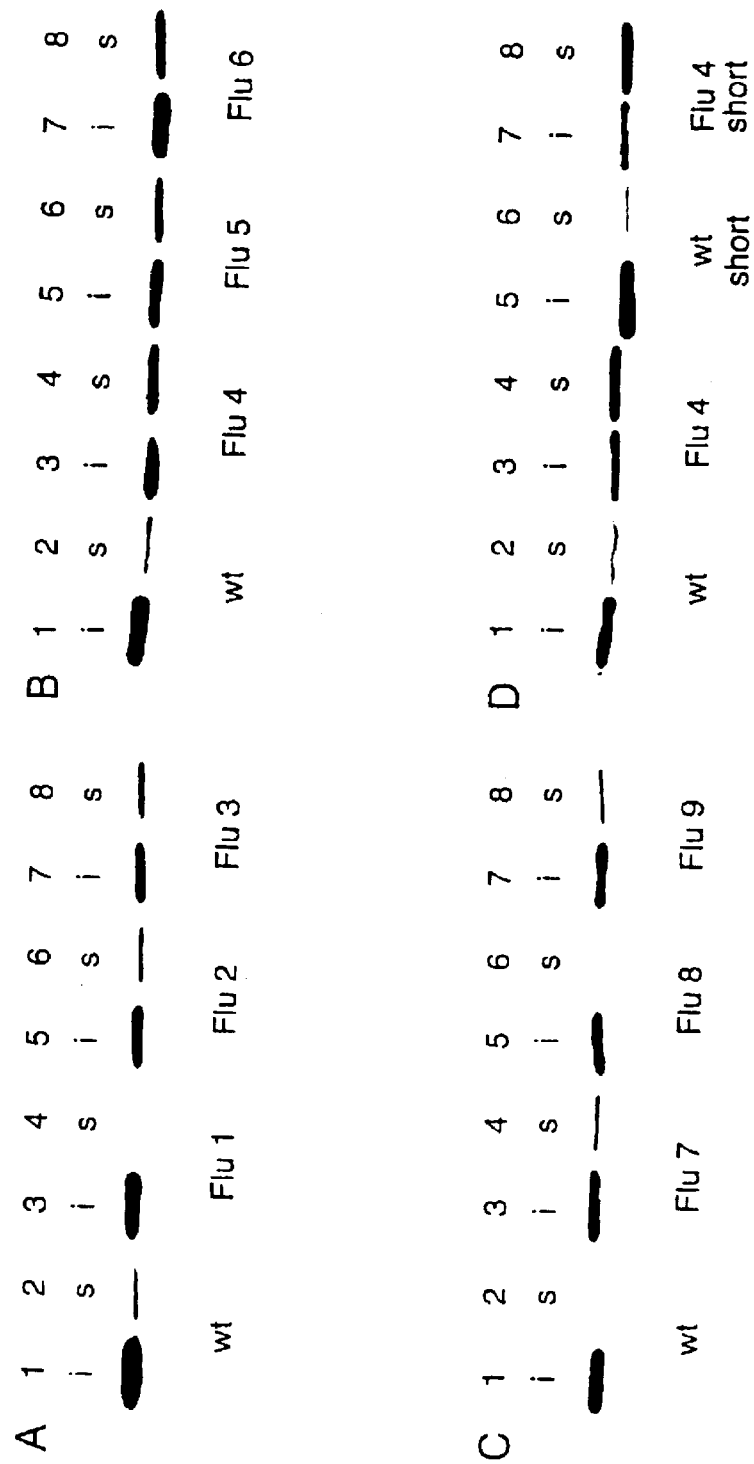

Figure 4: Scatchard plots of fluorescence titration of fluorescein with antibody: a) Titration of wt scFv; b) Titration of Flu4(V84D)
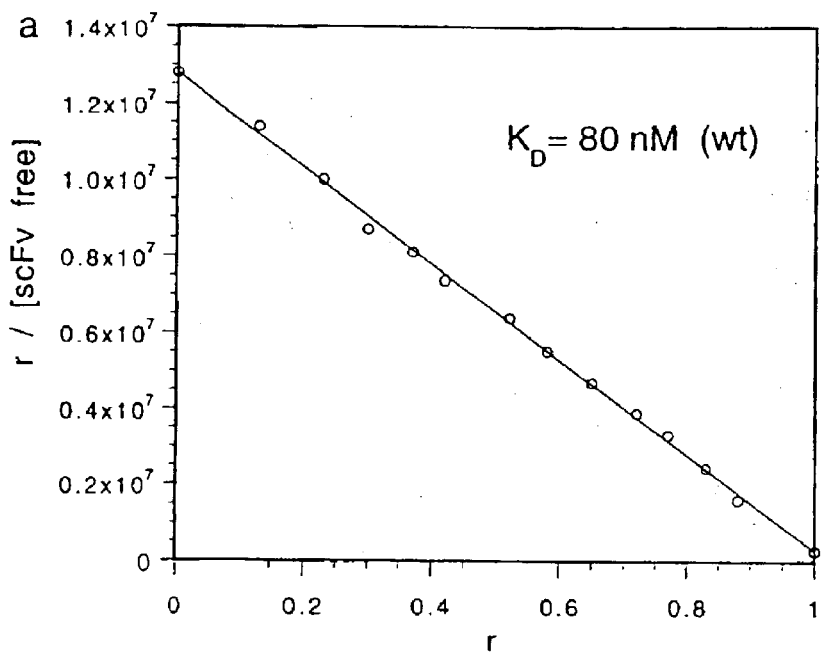
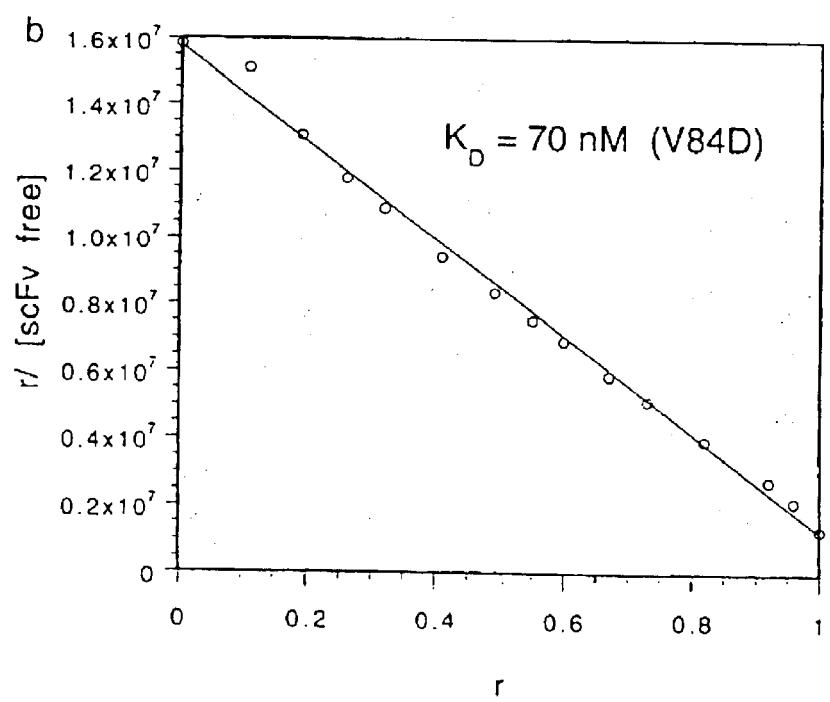

Figure 5: Overlay plot of urea denaturation. (x) wt scFv, (o) Flu4
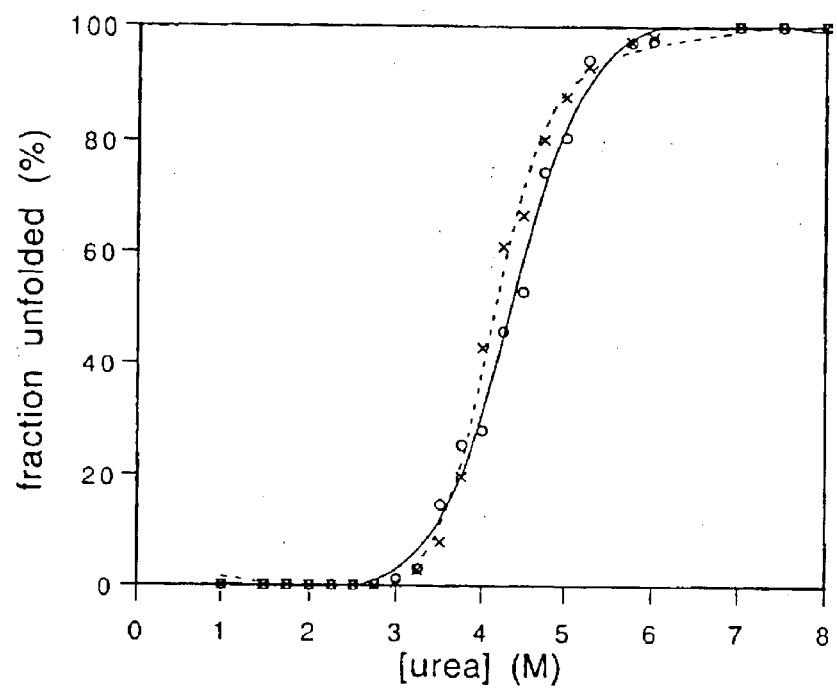
Figure 6: Thermal denaturation time courses at 40°C and 44°C for wt and Flu4 scFv fragments
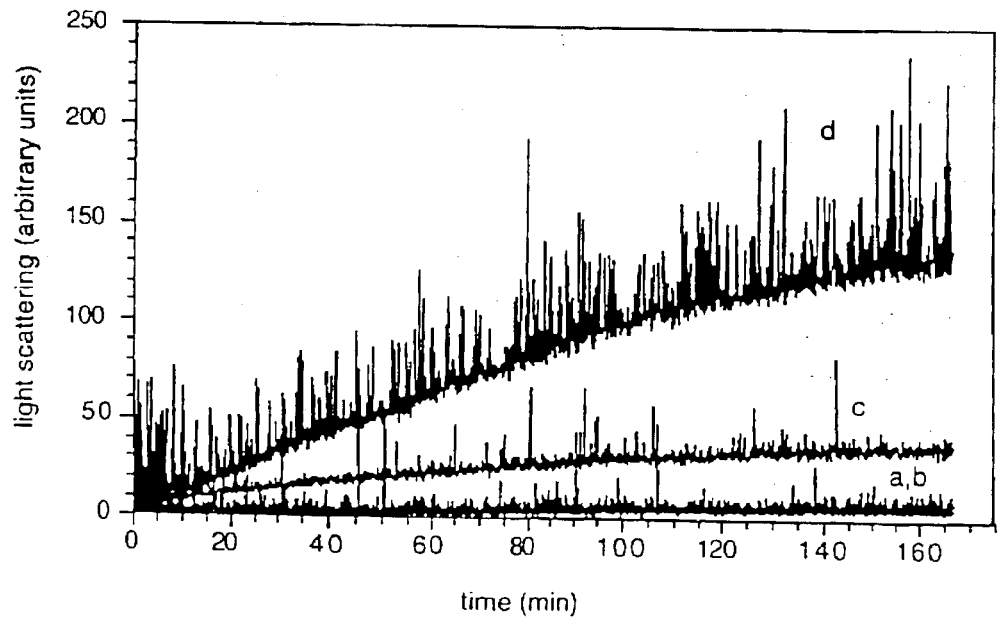

Table 1: Sequence variability of residues contributing to the v/c interface

| Position | L9 | | | | L10 | | L12 | | | | L15 | | | | L39 | | | |
|---|---|---|---|---|---|---|---|---|---|---|---|---|---|---|---|---|---|---|
| % exp. (FAB) | 91 | | | | 59 | | 41 | | | | 48 | | | | 37 | | | |
| % exp. (ind.) | 91 | | | | 65 | | 47 | | | | 49 | | | | 37 | | | |
| % buried v/c | 0 | | | | 10 | | 12 | | | | 0 | | | | 1 | | | |
| Species | kappa | | lambda | | kappa | | kappa | | lambda | | kappa | | lambda | | kappa | | lambda | |
| | hu | mu | hu | mu | hu | mu | hu | mu | hu | mu | hu | mu | hu | mu | hu | mu | hu | mu |
| Seq. 4-4-20 | Leu | | | | Ser | | Pro | | | | Leu | | | | Lys | | | |
| Consensus | Ser | Leu | Ser | Ala | Ser | Thr | Ser | Ser | Ser | Thr | Pro | Leu | Pro | Pro | Lys | Lys | Lys | Lys |
| Distribution: | | | | | | | | | | | | | | | | | | |
| Asp | 8 | 0 | 0 | 0 | 0 | 0 | 0 | 0 | 0 | 0 | 0 | 0 | 0 | 0 | 0 | 0 | 0 | 0 |
| Glu | 0 | 0 | 0 | 0 | 0 | 0 | 0 | 0 | 0 | 0 | 0 | 0 | 0 | 0 | 0 | 1 | 0 | 0 |
| Lys | 0 | 6 | 0 | 0 | 0 | 0 | 0 | 0 | 0 | 0 | 0 | 0 | 0 | 0 | 83 | 92 | 30 | 96 |
| Arg | 0 | 0 | 0 | 0 | 0 | 0 | 0 | 0 | 0 | 0 | 0 | 0 | 0 | 0 | 14 | 7 | 11 | 0 |
| His | 0 | 0 | 0 | 1 | 0 | 0 | 0 | 0 | 0 | 0 | 0 | 0 | 0 | 0 | 0 | 0 | 20 | 0 |
| Thr | 0 | 4 | 0 | 4 | 49 | 6 | 0 | 3 | 0 | 93 | 1 | 0 | 0 | 0 | 1 | 0 | 1 | 0 |
| Ser | 43 | 24 | 90 | 0 | 48 | 60 | 84 | 50 | 99 | 0 | 0 | 1 | 0 | 0 | 1 | 0 | 0 | 0 |
| Asn | 0 | 0 | 0 | 0 | 0 | 0 | 0 | 0 | 0 | 0 | 0 | 0 | 0 | 0 | 0 | 0 | 1 | 0 |
| Gln | 0 | 0 | 0 | 0 | 0 | 0 | 0 | 0 | 0 | 0 | 0 | 0 | 0 | 0 | 0 | 0 | 0 | 0 |
| Gly | 25 | 1 | 7 | 0 | 0 | 0 | 0 | 0 | 0 | 0 | 0 | 0 | 0 | 0 | 0 | 1 | 4 | 1 |
| Ala | 11 | 41 | 0 | 90 | 0 | 0 | 4 | 23 | 0 | 0 | 0 | 8 | 0 | 0 | 0 | 0 | 0 | 0 |
| Cys | 0 | 0 | 0 | 0 | 0 | 0 | 0 | 0 | 0 | 0 | 0 | 0 | 1 | 0 | 0 | 0 | 0 | 0 |
| Pro | 0 | 2 | 2 | 1 | 0 | 0 | 11 | 20 | 0 | 0 | 45 | 28 | 84 | 96 | 0 | 0 | 0 | 0 |
| Val | 1 | 0 | 0 | 3 | 0 | 24 | 0 | 0 | 0 | 1 | 41 | 10 | 0 | 0 | 0 | 0 | 3 | 0 |
| Ile | 0 | 0 | 0 | 0 | 0 | 2 | 0 | 0 | 0 | 0 | 2 | 2 | 14 | 4 | 0 | 0 | 0 | 0 |
| Leu | 11 | 19 | 0 | 0 | 2 | 7 | 0 | 0 | 0 | 0 | 11 | 49 | 0 | 0 | 0 | 0 | 24 | 0 |
| Met | 0 | 0 | 0 | 0 | 0 | 1 | 0 | 0 | 0 | 0 | 0 | 0 | 0 | 0 | 0 | 0 | 0 | 0 |
| Phe | 0 | 1 | 0 | 0 | 0 | 0 | 0 | 0 | 0 | 0 | 0 | 1 | 0 | 0 | 0 | 0 | 3 | 0 |
| Tyr | 0 | 0 | 0 | 0 | 0 | 0 | 0 | 0 | 0 | 0 | 0 | 0 | 0 | 0 | 0 | 0 | 2 | 3 |
| Trp | 0 | 0 | 0 | 0 | 0 | 0 | 0 | 0 | 0 | 0 | 0 | 0 | 0 | 0 | 0 | 0 | 0 | 0 |

Table 1: Sequence variability of residues contributing to the v/c interface (cont.)

| | L40 | | | | L41 | | | | L80 | | | | L81 | | | | L83 | | | | L103 | | |
|---|---|---|---|---|---|---|---|---|---|---|---|---|---|---|---|---|---|---|---|---|---|---|---|
| | kappa | | lambda | | kappa | | lambda | | kappa | | lambda | | kappa | | lambda | | kappa | | lambda | | kappa | | |
| | 64 | 82 | 22 | | 114 | 121 | 3 | | 57 | 74 | 21 | | 70 | 74 | 5 | | 17 | 38 | 46 | | 42 | 58 | 26 |
| | hu | mu | hu | mu | hu | mu | hu | mu | hu | mu | hu | mu | hu | mu | hu | mu | hu | mu | hu | mu | hu | mu |
| consensus | Pro | Pro | Pro | Pro | Gly | Gly | Gly | Asp | Pro | Ala | Ala | Thr | Glu | Glu | Glu | Glu | Phe | Leu | Leu | Glu | Lys | Lys |
| | 0 | 0 | 0 | 0 | 0 | 10 | 3 | 96 | 0 | 0 | 0 | 0 | 10 | 7 | 4 | 0 | 0 | 0 | 0 | 15 | 0 | 0 |
| | 0 | 0 | 0 | 0 | 0 | 4 | 0 | 0 | 0 | 8 | 0 | 0 | 86 | 93 | 69 | 82 | 0 | 0 | 99 | 68 | 0 | 0 |
| | 0 | 0 | 0 | 0 | 0 | 0 | 0 | 0 | 0 | 0 | 0 | 0 | 0 | 0 | 0 | 0 | 0 | 0 | 0 | 0 | 88 | 98 |
| | 1 | 0 | 0 | 0 | 0 | 1 | 2 | 0 | 0 | 0 | 0 | 0 | 0 | 0 | 0 | 0 | 0 | 0 | 0 | 0 | 8 | 1 |
| | 0 | 0 | 0 | 0 | 0 | 2 | 3 | 0 | 0 | 0 | 0 | 0 | 0 | 0 | 0 | 0 | 0 | 0 | 0 | 0 | 0 | 0 |
| | 0 | 1 | 1 | 0 | 0 | 0 | 0 | 0 | 0 | 3 | 17 | 94 | 0 | 0 | 0 | 0 | 2 | 3 | 0 | 0 | 2 | 0 |
| | 2 | 19 | 5 | 0 | 0 | 0 | 0 | 0 | 9 | 6 | 19 | 0 | 0 | 0 | 0 | 0 | 0 | 0 | 0 | 0 | 0 | 0 |
| | 0 | 3 | 0 | 0 | 0 | 0 | 0 | 3 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 0 | 0 | 0 | 0 | 0 | 0 | 0 | 0 | 0 | 1 | 0 | 0 | 0 | 0 |
| | 0 | 0 | 0 | 0 | 99 | 80 | 90 | 0 | 16 | 64 | 56 | 4 | 1 | 0 | 17 | 0 | 0 | 31 | 0 | 0 | 0 | 0 |
| | 1 | 0 | 1 | 1 | 0 | 0 | 2 | 0 | 0 | 0 | 0 | 0 | 0 | 0 | 0 | 0 | 0 | 0 | 0 | 0 | 0 | 0 |
| | 0 | 0 | 0 | 0 | 0 | 0 | 0 | 0 | 74 | 9 | 2 | 1 | 0 | 0 | 0 | 0 | 20 | 0 | 0 | 0 | 0 | 0 |
| | 94 | 77 | 92 | 96 | 0 | 0 | 0 | 0 | 0 | 2 | 5 | 0 | 0 | 0 | 0 | 0 | 6 | 12 | 0 | 0 | 0 | 0 |
| | 1 | 0 | 0 | 0 | 0 | 0 | 0 | 0 | 0 | 0 | 0 | 0 | 0 | 0 | 0 | 0 | 1 | 11 | 0 | 0 | 0 | 0 |
| | 0 | 0 | 0 | 0 | 0 | 0 | 0 | 0 | 0 | 0 | 0 | 0 | 0 | 0 | 0 | 0 | 0 | 32 | 0 | 0 | 0 | 0 |
| | 0 | 0 | 0 | 3 | 0 | 0 | 0 | 0 | 0 | 0 | 0 | 0 | 0 | 0 | 0 | 0 | 72 | 2 | 0 | 0 | 0 | 0 |
| | 0 | 0 | 0 | 0 | 0 | 0 | 0 | 0 | 0 | 2 | 0 | 0 | 0 | 0 | 0 | 0 | 0 | 7 | 0 | 0 | 0 | 0 |
| | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 0 | 0 | 0 | 0 | 0 | 2 | 0 | 0 | 0 | 0 | 0 | 0 | 0 | 0 | 0 | 0 | 0 | 0 | 0 | 0 | 0 | 0 |

Table 1: Sequence variability of residues contributing to the v/c interface (cont.)

| | | L105 19 57 66 | | | | L106 14 28 56 | | | | L106A 56 65 15 | | L107 56 65 15 | | | | L108 47 103 55 | | | |
|---|---|---|---|---|---|---|---|---|---|---|---|---|---|---|---|---|---|---|---|
| lambda | | kappa | | lambda | | kappa | | lambda | | lambda | | kappa | | lambda | | kappa | | lambda | |
| hu | mu | hu | mu | hu | mu | hu | mu | hu | mu | hu | mu | hu | mu | hu | mu | hu | mu | hu | mu |
| Lys | Lys | Glu | Glu | Thr | Thr | Ile | Ile | Val | Val | Leu | Leu | Lys | Lys | Gly | Gly | Arg | Arg | Gln | Gln |
| 0 | 0 | 12 | 0 | 0 | 0 | 0 | 0 | 0 | 0 | 0 | 0 | 0 | 0 | 0 | 0 | 0 | 0 | 0 | 0 |
| 2 | 0 | 84 | 99 | 97 | 0 | 0 | 0 | 0 | 0 | 0 | 0 | 94 | 97 | 0 | 0 | 0 | 0 | 0 | 0 |
| 83 | 100 | 0 | 0 | 0 | 0 | 0 | 0 | 0 | 0 | 0 | 0 | 2 | 1 | 8 | 3 | 97 | 100 | 0 | 0 |
| 6 | 0 | 0 | 0 | 0 | 0 | 1 | 0 | 0 | 0 | 0 | 0 | 0 | 0 | 0 | 0 | 0 | 0 | 0 | 0 |
| 0 | 0 | 1 | 0 | 0 | 0 | 0 | 0 | 0 | 0 | 0 | 0 | 0 | 0 | 0 | 0 | 0 | 0 | 0 | 6 |
| 2 | 0 | 0 | 0 | 0 | 100 | 0 | 0 | 0 | 0 | 0 | 0 | 0 | 0 | 0 | 0 | 0 | 0 | 0 | 0 |
| 0 | 0 | 0 | 0 | 1 | 0 | 0 | 0 | 0 | 0 | 0 | 0 | 1 | 0 | 5 | 0 | 0 | 0 | 0 | 0 |
| 4 | 0 | 0 | 0 | 0 | 0 | 1 | 0 | 0 | 0 | 0 | 0 | 0 | 0 | 0 | 0 | 0 | 0 | 0 | 0 |
| 2 | 0 | 1 | 0 | 0 | 0 | 0 | 0 | 0 | 0 | 0 | 0 | 0 | 1 | 0 | 0 | 0 | 0 | 95 | 54 |
| 0 | 0 | 0 | 0 | 0 | 0 | 0 | 0 | 0 | 0 | 0 | 0 | 0 | 0 | 0 | 0 | 1 | 0 | 2 | 0 |
| 0 | 0 | 0 | 0 | 0 | 0 | 0 | 0 | 0 | 0 | 0 | 0 | 0 | 0 | 83 | 92 | 0 | 0 | 1 | 0 |
| 0 | 0 | 0 | 0 | 1 | 0 | 0 | 0 | 0 | 0 | 0 | 0 | 0 | 0 | 0 | 0 | 0 | 0 | 0 | 0 |
| 0 | 0 | 1 | 0 | 0 | 0 | 3 | 1 | 100 | 100 | 0 | 0 | 0 | 0 | 1 | 0 | 0 | 0 | 1 | 0 |
| 0 | 0 | 0 | 0 | 0 | 0 | 88 | 73 | 0 | 0 | 2 | 2 | 0 | 0 | 0 | 0 | 0 | 0 | 0 | 0 |
| 0 | 0 | 1 | 0 | 0 | 0 | 1 | 25 | 0 | 0 | 97 | 97 | 0 | 0 | 0 | 0 | 0 | 0 | 0 | 6 |
| 0 | 0 | 0 | 0 | 0 | 0 | 3 | 0 | 0 | 0 | 0 | 0 | 0 | 0 | 3 | 0 | 0 | 0 | 0 | 0 |
| 0 | 0 | 0 | 0 | 0 | 0 | 2 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 1 | 0 | 0 | 0 | 0 | 0 |

Table 1: Sequence variability of residues contributing to the v/c interface (cont.)

| Position | H9 | | H10 | | H11 | | H13 | | H14 | | H41 | | H42 | | H43 | |
|---|---|---|---|---|---|---|---|---|---|---|---|---|---|---|---|---|
| % exp. (FAB) | 29 | | 65 | | 31 | | 69 | | 36 | | 72 | | 111 | | 65 | |
| % exp. (ind.) | 33 | | 72 | | 71 | | 73 | | 36 | | 72 | | 115 | | 78 | |
| % buried v/c | 7 | | 8 | | 58 | | 5 | | 0 | | 0 | | 3 | | 2 | |
| Species | hu | mu | hu | mu | hu | mu | hu | mu | hu | mu | hu | mu | hu | mu | hu | mu |
| Seq. 4-4-20 | Gly | Gly | Gly | Gly | Leu | Leu | Lys | Gln | Pro | Pro | Pro | Pro | Glu | Glu | Lys | Lys |
| Consensus | Gly | Pro | Gly | Glu | Leu | Leu | Lys | Lys | Pro | Pro | Ala | Arg | Pro | Pro | Gly | Gly |
| Distribution: | | | | | | | | | | | | | | | | |
| Asp | 0 | 0 | 5 | 2 | 0 | 0 | 0 | 0 | 0 | 0 | 0 | 0 | 0 | 0 | 0 | 2 |
| Glu | 2 | 0 | 27 | 54 | 0 | 0 | 2 | 0 | 0 | 0 | 0 | 0 | 0 | 0 | 1 | 19 |
| Lys | 0 | 0 | 0 | 0 | 0 | 0 | 59 | 54 | 0 | 0 | 0 | 3 | 0 | 0 | 0 | 0 |
| Arg | 0 | 0 | 1 | 0 | 0 | 0 | 3 | 18 | 0 | 0 | 1 | 36 | 1 | 0 | 0 | 1 |
| His | 0 | 0 | 0 | 0 | 0 | 0 | 1 | 0 | 0 | 0 | 1 | 0 | 0 | 0 | 0 | 0 |
| Thr | 1 | 2 | 1 | 0 | 0 | 0 | 0 | 0 | 0 | 1 | 1 | 13 | 1 | 11 | 0 | 0 |
| Ser | 1 | 1 | 0 | 2 | 0 | 0 | 0 | 0 | 2 | 3 | 10 | 18 | 2 | 3 | 8 | 0 |
| Asn | 0 | 0 | 0 | 0 | 0 | 0 | 0 | 0 | 0 | 0 | 0 | 1 | 0 | 1 | 0 | 0 |
| Gln | 0 | 0 | 0 | 0 | 0 | 1 | 34 | 22 | 0 | 0 | 0 | 0 | 1 | 0 | 0 | 0 |
| Gly | 42 | 29 | 61 | 38 | 0 | 0 | 0 | 0 | 0 | 0 | 0 | 0 | 0 | 0 | 90 | 76 |
| Ala | 33 | 31 | 3 | 1 | 0 | 0 | 0 | 5 | 1 | 8 | 59 | 7 | 1 | 0 | 1 | 2 |
| Cys | 0 | 0 | 0 | 0 | 0 | 0 | 0 | 0 | 0 | 85 | 0 | 0 | 0 | 0 | 0 | 0 |
| Pro | 21 | 36 | 0 | 0 | 0 | 0 | 0 | 0 | 96 | 0 | 18 | 14 | 94 | 83 | 1 | 0 |
| Val | 0 | 1 | 0 | 1 | 38 | 1 | 0 | 0 | 0 | 0 | 1 | 1 | 0 | 0 | 0 | 0 |
| Ile | 0 | 0 | 0 | 0 | 0 | 2 | 0 | 0 | 0 | 3 | 0 | 1 | 0 | 0 | 1 | 0 |
| Leu | 0 | 0 | 0 | 0 | 60 | 95 | 0 | 0 | 0 | 0 | 1 | 0 | 0 | 0 | 0 | 0 |
| Met | 0 | 0 | 0 | 0 | 0 | 0 | 0 | 0 | 0 | 0 | 7 | 0 | 0 | 0 | 0 | 0 |
| Phe | 0 | 0 | 0 | 0 | 2 | 0 | 0 | 0 | 0 | 0 | 0 | 6 | 0 | 0 | 0 | 0 |
| Tyr | 0 | 0 | 0 | 0 | 0 | 0 | 0 | 0 | 0 | 0 | 0 | 0 | 0 | 0 | 0 | 0 |
| Trp | 0 | 0 | 0 | 0 | 0 | 0 | 0 | 0 | 0 | 0 | 0 | 0 | 0 | 0 | 0 | 0 |

Table 1: Sequence variability of residues contributing to the v/c interface (cont.)

| | | | | | | | | | | | | | | | | | | | | | | | |
|---|---|---|---|---|---|---|---|---|---|---|---|---|---|---|---|---|---|---|---|---|---|---|---|
| H113 72 78 7 | mu | Ser | Ser | 0 | 0 | 0 | 0 | 0 | 0 | 77 | 0 | 0 | 1 | 22 | 0 | 0 | 0 | 0 | 0 | 0 | 0 | 0 | 0 |
| | hu | | Ser | 0 | 0 | 0 | 0 | 0 | 0 | 97 | 0 | 0 | 0 | 0 | 2 | 0 | 0 | 0 | 0 | 0 | 0 | 0 |
| H112 25 68 62 | mu | Ser | Ser | 0 | 0 | 0 | 0 | 0 | 0 | 100 | 0 | 0 | 0 | 0 | 0 | 0 | 0 | 0 | 0 | 0 | 0 | 0 |
| | hu | | Ser | 0 | 0 | 0 | 0 | 0 | 0 | 98 | 0 | 0 | 0 | 0 | 0 | 1 | 1 | 0 | 0 | 0 | 0 | 0 |
| H110 26 55 52 | mu | Thr | Thr | 0 | 0 | 0 | 0 | 0 | 99 | 0 | 0 | 0 | 0 | 0 | 0 | 0 | 0 | 0 | 0 | 0 | 0 | 0 |
| | hu | | Thr | 0 | 0 | 0 | 0 | 0 | 89 | 2 | 0 | 0 | 0 | 0 | 0 | 0 | 1 | 7 | 0 | 0 | 0 | 0 |
| H108 52 64 18 | mu | Ser | Thr | 0 | 0 | 0 | 0 | 0 | 51 | 23 | 0 | 0 | 0 | 0 | 0 | 0 | 0 | 0 | 25 | 0 | 0 | 0 |
| | hu | | Leu | 0 | 0 | 1 | 3 | 0 | 23 | 0 | 0 | 0 | 0 | 0 | 0 | 1 | 0 | 0 | 63 | 9 | 0 | 0 |
| H105 72 82 1 | mu | Gln | Gln | 0 | 0 | 0 | 0 | 1 | 4 | 0 | 0 | 83 | 0 | 11 | 0 | 0 | 0 | 0 | 0 | 0 | 0 | 0 |
| | hu | | Gln | 0 | 1 | 10 | 5 | 1 | 0 | 0 | 0 | 80 | 0 | 0 | 2 | 0 | 0 | 0 | 0 | 0 | 0 | 0 |
| H89 34 37 1 | mu | Ile | Val | 0 | 0 | 0 | 1 | 0 | 15 | 0 | 0 | 0 | 0 | 0 | 0 | 0 | 50 | 13 | 7 | 13 | 0 | 0 |
| | hu | | Val | 0 | 0 | 0 | 0 | 0 | 4 | 0 | 0 | 0 | 0 | 0 | 0 | 0 | 76 | 5 | 6 | 7 | 0 | 0 |
| H87 28 31 8 | mu | Met | Ser | 0 | 0 | 0 | 0 | 0 | 46 | 51 | 0 | 0 | 0 | 1 | 0 | 0 | 0 | 0 | 0 | 1 | 0 | 0 |
| | hu | | Thr | 0 | 0 | 0 | 0 | 0 | 96 | 2 | 0 | 0 | 0 | 0 | 0 | 0 | 0 | 0 | 0 | 0 | 0 | 0 |
| H84 76 77 2 | mu | Val | Ser | 0 | 0 | 0 | 0 | 0 | 12 | 70 | 3 | 0 | 0 | 12 | 0 | 1 | 0 | 1 | 0 | 0 | 1 | 0 |
| | hu | | Ala | 1 | 0 | 0 | 0 | 0 | 4 | 18 | 0 | 0 | 0 | 55 | 0 | 14 | 4 | 1 | 0 | 0 | 2 | 0 |

Table 2: Mutations introduced in the scFv fragment of the antibody 4-4-20

| | L15E ($V_L$) | L11N ($V_H$) | L11D ($V_H$) | V84D ($V_H$) |
|---|---|---|---|---|
| Flu 1 | • | | | |
| Flu 2 | | • | | |
| Flu 3 | | | • | |
| Flu 4 | | | | • |
| Flu 5 | | • | | • |
| Flu 6 | | | • | • |
| Flu 7 | • | • | | |
| Flu 8 | • | | • | |
| Flu 9 | • | • | | • |
| Flu 4 short | | | | • |

Table 3: $K_D$ values of the different scFv mutants determined in fluorescence titration

| | Flu wt | Flu 3 | Flu 4 | Flu 6 | Flu wt# |
|---|---|---|---|---|---|
| $K_D$ (nM) | 80 ± 7 | 60 ± 12 | 70 ± 10 | 75 ± 13 | 90 |

IMMUNOGLOBULIN SUPERFAMILY DOMAINS AND FRAGMENTS WITH INCREASED SOLUBILITY

CROSS-REFERENCE TO RELATED APPLICATIONS

This application is a Continuation of International Application PCT/EP97/03792, filed Jul. 16, 1997, which claims priority from European patent application EP 96111441.0, filed Jul. 16, 1996.

BACKGROUND OF THE INVENTION

The present invention relates to the modification of immunoglobuling superfamily (IgSF) domains and derivatives thereof so as to increase their solubility, and hence the yield, and ease of handling.

Small antibody fragments show exciting promise for use as therapeutic agents, diagnostic reagents, and for biochemical research. Thus, they are needed in large amounts, and the expression of antibody fragments, e.g. Fv, single-chain-Fv (scFv), or Fab in the periplasm of *E. coli* (Skerra & Plückthun 1988; Better et al., 1988) is now used routinely in many laboratories. Expression yields vary widely, however, especially in the case of scFvs. While some fragments yield up to several mg of functional, soluble protein per litre and OD of culture broth in shake flask 25 culture (Carter et al., 1992, Plückthun et al. 1996), other fragments may almost exclusively lead to insoluble material, often found in so-called inclusion bodies. Functional protein may be obtained from the latter in modest yields by a laborious and time-consuming refolding process. The factors influencing antibody expression levels are still only poorly understood.

Folding efficiency and stability of the antibody fragments, protease lability and toxicity of the expressed proteins to the host cells often severely limit actual production levels, and several attempts have been tried to increase expression yields. For example, Knappik & Plückthun (1995) have identified key residues in the antibody framework which influence expression yields dramatically. Similarly, Ullrich et al. (1995) found that point mutations in the CDRs can increase the yields in periplasmic antibody fragment expression. Nevertheless, these strategies are only applicable to a few antibodies.

The observations by Knappik & Plückthun (1995) indicate that optimizing those parts of the antibody fragment which are not directly involved in antigen recognition can significantly improve folding properties and production yields of recombinant Fv and scFv constructs. The causes for the improved expression behavior lie in the decreased aggregation behavior of these molecules. For other molecules, fragment stability and protease resistance may also be affected. The understanding of how specific sequence modifications change these properties is still very limited and currently under active investigation.

Difficulties in expressing and manipulating protein domains may arise because amino acids which are normally buried within the protein structure become exposed when only a portion of the whole molecule is expressed. Aggregation may occur through interaction of newly solvent-exposed hydrophobic residues originally forming the contact regions between adjacent domains. Leistler and Perham (1994) could show that a certain domain of glutathione reductase may be expressed separately from its neighboring domains, but the protein showed non-specific association in vitro forming multimeric protein species. The introduction of hydrophilic residues instead of exposed hydrophobic amino acids could decrease this aggregation tendency and thus stabilize this isolated domain. Both wild type and modified domains were exclusively found in inclusion bodies and had to be refolded. Although in vitro experiments contributed a lot to define various intermolecular interactions, which drive folding processes, they are only of limited value in predicting the folding behaviour of different polypeptide chains in vivo (Gething & Sambrook, 1992). Thus, Leistler and Perham do not teach or suggest how to increase expression yields of soluble protein domains.

In the case of antibodies, two chains comprising several domains dimerize, each domain consisting of a b-barrel whose two b-sheets are held together by a disulphide bond, forming the so-called immunoglobulin fold. Two domains, one variable domain (VL) and one constant domain (CL) are adjacent along the longitudinal axis in the light chain (VL-CL), and four domains, one variable domain (VH) and three constant domain (CH1 to CH3) are adjacent along the longitudinal axis in the heavy chain (VH-CH1-CH2-CH3). In the dimer formed by chains a and b, two such domains associate laterally: VLa with VHa, CLa with CH1a, VLb with VHb, CLb with CH1b CH2a with CH2b and CH3a with CH3b. In WO 92/01787 (Johnson et al., 1992), it is taught that isolated single domains, e.g. VH, can be modified in the former VL/VH interface region by exchanging hydrophobic residues by hydrophilic ones without changing the specificity of the parent domain. The rationale for WO 92/01787 was the assumption that exposed hydrophobic residues might lead to non-specific binding, interaction with surfaces and decreased stability. Data for increase in binding specificity was given, but increase in expression level was not shown. Furthermore, WO 92/01787 would not be applicable to any antibody fragment containing the complete antigen binding site, as it must contain VL and VH. In the case of T cell receptors, two chains (a and b) dimerize, each consisting of a variable (V) and a constant (C) domain with the immunoglobulin fold, and one transmembrane domain. In each chain, the variable and constant domains are adjacent along the longitudinal axis in the chains (Va-Ca; Vb-Cb) and associate laterally with the corresponding domains of the second chain (Va-Vb; Ca-Cb).

Various other molecules of the immunoglobulin superfamily, such as CD2, CD4, CD16, CD22, comprise only one chain, wherein two or more domains (variable and/or constant) with the immunoglobulin fold are adjacent along the longitudinal axis in the chains.

SUMMARY OF THE INVENTION

The present inventors have found that expression problems are largely associated with a part of the molecule that has hitherto not been regarded relevant for expression studies and which comprises the interface between adjacent domains within an immunoglobulin chain. This surprising finding forms the basis of the present invention, which provides a general solution to the problems associated with production of domains or fragments of the immunoglobulin superfamily (IgSF), especially antibody fragments, which exhibit poor solubility or reduced levels of expression.

In addition to lateral interactions between domains of different chains described above, there are well documented contacts between adjacent domains within individual chains along the longitudinal axis. For example, in the case of an antibody (Lesk & Chothia, 1988), the "bottom" of VL makes contact with the "top" of CL, and, in a similar manner there are contacts between VH and CH1. The contacts at these inter-domain interfaces are probably essential for the compact arrangement of the Fab fragment, and, as is typical for such contacts, are at least partially hydrophobic in nature (Lesk & Chothia, 1988).

The basis of the present invention is the surprising finding that the solubility (and hence the yield) of antibody fragments comprising at least one domain can be dramatically increased by decreasing the hydrophobicity of former interfaces at the "end" of said domain, where it would normally adjoin a second domain within a chain in a larger antibody fragment or full antibody. This is surprising and could not have been predicted from the prior art (WO 92/01787), because the size of the longitudinal interface, for example, in a scFv fragment, is much smaller than that between VH and VL, and therefore, the amino acids which make up the interfaces between VH and CH1 or between VL and CL in a Fab fragment represent a much smaller proportion of the total surface area of the scFv molecule, and would accordingly be expected to play less of a role in determining the physical properties of the molecule.

The present invention has the additional advantage that because the alterations effected in the molecules that lead to said decreased hydrophobicity of former interfaces are located at the most distant part of the domain from the CDRs, applying the invention is unlikely to have a deleterious effect on the binding properties of the molecule. This is not the case in WO 92/01787, where at least one modification is close to the CDRs and may therefore be expected to have an impact on antigen binding. Furthermore, WO 92/01787 cannot be applied to VL/VH heterodimers, as explained above.

BRIEF DESCRIPTION OF THE DRAWINGS

FIG. 1 provides a space filling representation of the Fv fragment of the antibody 4-4-20.

FIG. 2 presents the variable/constant domain interface residues for VL (2a) and VH (2b). For 30 non-redundant Fab fragments taken from the Brookhaven Databank, the solvent accessible surface of the amino acid side chains was calculated in the context of an Fv and of an Fab fragment. The plot shows the relative reduction in accessible surface upon contact with the constant domains (overlay plot for all 30 Fv fragments). In the sequence alignment, residues contributing to the v/c interface are highlighted. The symbols indicate the relative reduction of solvent accessible surface upon removing the constant domains (symbols: no symbol <1%; 1<20%; n<40%; s<60%; t<80%, and $u^3$ 80%). Circles indicate those positions which are further analyzed (see Table 1).

FIG. 3 presents Western blots showing the insoluble (i) and soluble (s) fractions of cell extracts, prepared as described in Material and Methods, expressing the scFv fragments of the antibody 4-4-20. The amino acids substituted in the various mutants are given in Table 2.

FIG. 4 presents a Scatchard plot of the fluorescence titration of fluorescein (20 nM) with antibody (4 to 800 nM), measured at 510 nm. The value r was obtained from (F-Fo)/(FY-Fo), where F is the measured fluorescein fluorescence at a given antibody concentration, Fo is the fluorescence in the absence of antibody and FY when antibody is present in large excess. Note that r gives the saturation of fluorescein by antibody. (a) Titration of wt scFv, (b) titration of Flu4 (V84D).

FIG. 5 presents an overlay plot of the urea denaturation curves ((X) wt scFv, (o) Flu4).

FIG. 6 presents the thermal denaturation time courses at 40 and 44° C. for wt and Flu4 scFv fragment ((a) wt scFv at 40° C., (b) Flu4 at 40° C., (c) Flu4 at 44° C., (d) wt scFv at 44° C.).

Table 1 describes the sequence variability of residues contributing to the v/c interface. Residue statistics are based on the variable domain sequences in the Kabat database (March 1996). Sequences which were <90% complete were excluded from the analysis. Number of sequences analyzed: human VL kappa: 404 of 881, murine VL kappa: 1061 of 2239, human VL lambda: 223 of 409, murine VL lambda: 71 of 206, human VH: 663 of 1756, murine VH: 1294 of 3849. Position refers to the sequence position according to Kabat et al. 1991, %exp. (Fab) to the relative side chain accessibility in an Fab fragment as calculated by the program NACCESS (NACCESS v2.0 by Simon Hubbard, %exp. (ind.) to the relative side chain accessibility in the isolated VL or VH domain, %buried to the relative difference in side chain accessibility between Fv and Fab fragment. Consensus refers to the sequence consensus, and Distribution to the distribution of residue types.

Table 2 describes mutations introduced in the scFv fragment of the antibody 4-4-20. Each line represents a different protein carrying the mutations indicated. The residues are numbered according to Kabat et al. (1991).

Table 3 describes KD values of the different scFv mutants determined in fluorescence titration. The KD values are given in nM, the error was calculated from the Scatchard analysis (FIG. 4). # determined by Miklasz et al. (1995).

DESCRIPTION OF THE PREFERRED EMBODIMENTS

The present invention relates to a modified immunoglobulin superfamily (IgSF) domain or fragment which differs from a parent IgSF domain or fragment in that the region which comprised or would comprise the interface with a second domain adjoined to said parent IgSF domain or fragment within the protein chain of a larger IgSF fragment or a full IgSF protein, and which is exposed in said parent IgSF domain or fragment in the absence of said second domain, is made more hydrophilic by modification.

In the context of the present invention, the term immunoglobulin superfamily (IgSF) domain refers to those parts of members of the immunoglobulin superfamily which are characterized by the immunoglobulin fold, said superfamily comprising the immunoglobulins or antibodies, and various other proteins such as T-cell receptors or integrins. The term IgSF fragment refers to any portion of a member of the immunoglobulin superfamily, said portion comprising at least one IgSF domain. The term adjoining domain refers to a domain which is contiguous with a first domain. The term interface refers to a region of said first domain where interaction with the adjoining domain takes place. The terms hydrophobic and hydrophilic refer to a physical property of amino acids, which can be estimated quantitatively: tabulated values of hydrophobicity for the twenty naturally-occurring amino acids are available (Nozaki & Tanford, 1971; Casari & Sippl, 1992; Rose & Wolfenden, 1993).

The residues to be modified can be identified in a number of ways. For example, in one way, the solvent accessibilities (Lee & Richards, 1971) of hydrophobic interface residues in said parent IgSF fragment compared to said larger IgSF fragment or full IgSF protein are calculated, with high accessibilities indicating highly exposed residues. In a second way, the number of van der Waals contacts of hydrophobic interface residues in said larger IgSF fragment or full IgSF protein is calculated. A large number for a residue of said parent domain indicates that it will be highly solvent-exposed in the absence of an adjoining domain. There are other ways of calculating or determining residues to be modified according to the present invention, and one of ordinary skill in the art will be able to identify and practice these ways.

By analyzing computer models of said parent IgSF fragment, interactions of said highly exposed residues within the fragment can be identified. Such interactions could stabilize the parent IgSF fragment. Residues, which interact closely with other hydrophobic residues and which can be identified by anyone of ordinary skill in the art, should not preferentially be mutated.

The modification referred to above may be effected in a number of ways which are well known to one skilled in the art. In a preferred embodiment, the modification is a substitution of one or more amino acids at the exposed interface, identified as described above, with amino acids which are more hydrophilic Alternatively, one or more amino acids can be inserted in said interface, or one or more amino acids can be deleted from said interface, so as to increase its overall hydrophilicity. Furthermore, any combination of substitution, insertion and deletion can be effected to reduce the hydrophobicity of said interface. Also comprised by the present invention is the possibility that the substitution or insertion comprises amino acids with a relatively high hydrophobicity value, or that the deletion comprises amino acids with relatively low hydrophobicity value, as long as the overall hydrophilicityvalue is increased in said interface region. Modifications such as substitution, insertion and deletion can be effected using standard methods which are well known to practitioners skilled in the art. By way of example, the skilled artisan can use either site-directed or PCR-based mutagenesis (Ho et al., 1989; Kunkel et al., 1991; Trower, 1994; Viville, 1994), or total gene synthesis (Prodromou & Pearl, 1992) to effect the necessary modifications). In a further embodiment, the mutations may be obtained by random mutagenesis and screening of random mutants, using a suitable expression and screening system (see, for example, Stemmer, 1994; Crameri et al., 1996).

In a preferred embodiment, the amino acid(s) which replace(s) the more hydrophobic amino acids include Asn, Asp, Arg, Gln, Glu, Gly, His, Lys, Ser, and Thr. These are among the more hydrophilic of the 20 naturally-occurring amino acids, and have proven to be particularly effective in the application of the present invention. Said amino acids, alone or in combination, or in combination with other amino acids, can also be used to form the above mentioned insertion which makes the interface region more hydrophilic.

The parent IgSF domain or fragment referred to above can be one of several different types. In a preferred embodiment, said parent domain or fragment is derived from an antibody. In one embodiment, said parent antibody fragment comprises an Fv fragment. In this context, the term Fv fragment refers to a complex comprising the VL (variable light) and VH (variable heavy) portions of the antibody molecule. In a further embodiment, the parent antibody fragment may be a single-chain Fv fragment (scFv; Bird et al., 1988; Huston et al., 1988), in which the VL and VH chains are joined, in either a VL-VH, or VH-VL orientation, by a peptide linker. In yet a further embodiment, the parent antibody fragment may be an Fv fragment stabilized by an inter-domain disulphide bond. This is a structure which can be made by engineering into each chain a single cysteine residue, wherein said cysteine residues from two chains become linked through oxidation to form a disulphide (Glockshuber et al., 1990; Brinkmann et al., 1993).

In a most preferred embodiment, the interface region of the variable domains mentioned above comprises residues 9, 10, 12, 15, 39, 40, 41, 80, 81, 83, 103, 105, 106, 106A, 107, 108 for VL, and residues 9, 10, 11, 13, 14, 41, 42, 43, 84, 87, 69, 105, 108, 110, 112, 113 for VH according to the Kabat numbering system (Kabat et al., 1991). Said numbering system was established for the sequences of whole antibodies, but can be adapted correspondingly to describe the sequences of isolated antibody domains or antibody fragments, even in the case of scFv fragments, where VL and VH are connected via a peptide linker, and where the protein sequence from N- to C-terminus has to be numbered differently. This means that the Kabat numbering system is used in the present invention as a sequence description relative to the existing data on antibody sequences, not as an absolute description of actual positions within the antibody fragment sequences of interest.

In a further embodiment, said parent antibody fragment comprises a Fab fragment. In this context, the term Fab refers to a complex comprising the VL-CL (variable and constant light) and VH-CH1 (variable and first constant heavy) portions of the antibody molecule, and the term interface region refers to a region in the first constant domain of the heavy chain (CH1) which is, or would be adjoined to, the CH2 domain in a larger antibody fragment or full antibody.

In a still further embodiment, said parent IgSF fragment is a fusion protein of any of said domains or fragments and another protein domain, derived from an antibody or any other protein or peptide. The advent of bacterial expression of antibody fragments has opened the way to the construction of proteins comprising fusions between antibody fragments and other molecules. A further embodiment of the present invention relates to such fusion proteins by providing for a DNA sequence which encodes both the modified IgSF domain or fragment, as described above, as well as an additional moiety. Particularly preferred are moieties which have a useful therapeutic function. For example, the additional moiety may be a toxin molecule which is able to kill cells (Vitetta et al., 1993). There are numerous examples of such toxins, well known those skilled in the art, such as the bacterial toxins *Pseudomonas* exotoxin A, and diphtheria toxin, as well as the plant toxins ricin, abrin, modeccin, saporin, and gelonin. By fusing such a toxin to an antibody fragment, the toxin can be targeted to, for example, diseased cells, and thereby have a beneficial therapeutic effect. Alternatively, the additional moiety may be a cytokine, such as IL-2 (Rosenberg & Lotze, 1986), which has a particular effect (in this case a T-cell proliferative effect) on a family of cells. In a further preferred embodiment, the additional moiety is at least part of a surface protein which may direct the fusion protein to the surface of an organism, for example, a cell or a phage, and thereby displays the IgSF partner. Preferably, the additional moiety is at least part of a coat protein of filamentous bacteriophages, most preferably of the geneIII protein. In a further embodiment, the additional moiety may confer on its IgSF partner a means of detection and/or purification. For example, the fusion protein could comprise the modified IgSF domain or fragment and an enzyme commonly used for detection purposes, such as alkaline phosphatase (Blake et al., 1984). There are numerous other moieties which can be used as detection or purification tags, which are well known to the practitioner skilled in the art. Particularly preferred are peptides comprising at least five histidine residues (Hochuli et al., 1988), which are able to bind to metal ions, and can therefore be used for the purification of the protein to which they are fused (Lindner et al., 1992). Also provided for by the invention are additional moieties such as the commonly used c-myc and FLAG tags (Hopp et al., 1988; Knappik & Plückthun, 1994).

By engineering one or more fused additional domains, IgSF domains or fragments can be assembled into larger molecules which also fall under the scope of the present invention. To the extent that the physical properties of the IgSF domain or fragment determine the characteristics of the assembly, the present invention provides a means of increasing the solubility of such larger molecules. For example, mini-antibodies (Pack, 1994) are dimers comprising two antibody fragments, each fused to a self-associating dimerization domain. Dimerization domains which are particularly preferred include those derived from a leucine zipper (Pack & Plückthun, 1992) or helix-turn-helix motif (Pack et al., 1993).

All of the above embodiments of the present invention can be effected using standard techniques of molecular biology known to anyone skilled in the art.

The compositions described above may have utility in any one of a number of settings. Particularly preferred are diagnostic and therapeutic compositions.

The present invention also provides methods for making the compositions and compounds comprised therein described above. Particularly preferred is a method comprising the following steps:
i) analyzing the interface region of an IgSF domain for hydrophobic residues which are solvent-exposed using either a solvent-accessibility approach (Lee & Richards, 1971), analysis of van der Waals interactions in the interface region, or similar methods which are well known to one skilled in the art,
ii) identifying one or more of the hydrophobic residues to be substituted by more hydrophilic residues, or one or more positions where hydrophilic residues or amino acid stretches enhancing the overall hydrophilicity of the interface region can be inserted into said interface region, or one or more positions where hydrophobic residues or amino acid stretches enhancing the overall hydrophobicity of the interface region can be deleted from said interface region, or any combination of said substitutions, said insertions, and said deletions to give one or more mutants of said parent IgSF domain,
iii) preparing DNA encoding mutants of said IgSF domain, characterized by the changes identified in ii), by using e.g. conventional mutagenesis or gene synthesis methods, said DNA being prepared either separately or as a mixture,
iv) introducing said DNA or DNA mixture in a vector system suitable for expression of said mutants,
v) introducing said vector system into suitable host cells and expressing said mutant or mixture of mutants,
vi) identifying and characterizing mutants which are obtained in higher yield in soluble form, and
vii) if necessary, repeating steps iii) to vi) to increase the hydrophilicity of said identified mutant or mutants further.

The host referred to above may be any of a number commonly used in the production of heterologous proteins, including but not limited to bacteria, such as *E. coli* (Ge et al, 1995), or *Bacillus subtilis* (Wu et al., 1993), fungi, such as yeasts (Horwitz et al., 1988; Ridder et al., 1995) or filamentous fungus (Nyyssönen et al., 1993), plant cells (Hiatt, 1990, Hiatt & Ma, 1993; Whitelam et al., 1994), insect cells (Potter et al., 1993; Ward et al., 1995), or mammalian cells (Trill et al., 1995).

The invention also relates to a method for the production of an IgSF domain or fragment of the invention comprising culturing a host cell of the invention and isolating said domain or fragment.

The invention is now demonstrated by the following examples, which are presented for illustration only and are not intended to limit the scope of the invention.

EXAMPLES i) Abbreviations

Abbreviations are defined as follows: CDR: complementarity determining region; dsFv: disulfide-linked Fv fragment; IMAC: immobilized metal ion affinity chromatography; IPTG: isopropyl-b-D-thiogalactopyranoside; i/s: ratio insoluble/soluble; H(X): heavy chain residue number X; L(X): light chain residue number X; NTA: nitrilo-triacetic acid; OD550: optical density at 550 nm; PDB: protein database; scFv: single-chain Fv fragment; SDS-PAGE: sodium dodecyl sulfate polyacrylamide gel electrophoresis; v/c: variable/constant; wt: wild type.

ii) Material and Methods (a) Calculation of Solvent Accessibility

Solvent accessible surface areas for 30 non-redundant Fab fragments and the Fv fragments derived from these by deleting the constant domain coordinates from the PDB file were calculated using the latest version, as of March 1996, of the program NACCESS (http://www.biochem.ucl.ac.uk/~roman/naccess/naccess) based on the algorhithm described by Lee & Richards (1971).

(b) scFv Gene Synthesis

The single-chain Fv fragment (scFv) in the orientation VL-linker-VH of the antibody 4-4-20 (Bedzyk et al., 1990) was obtained by gene synthesis (Prodromou and Pearl, 1992). The VL domain carries a three-amino acid long FLAG tag (Knappik and Plückthun, 1994). We have used two different linkers with a length of 15 (Gly4Ser)3 and 30 amino acids (Gly4Ser)6, respectively. The gene so obtained was cloned into a derivative of the vector pIG6 (Ge et al., 1995). The mutant antibody fragments were constructed by site-directed mutagenesis (Kunkel et al., 1987) using single-stranded DNA and up to three oligonucleotides per reaction.

(c) Expression

Growth curves were obtained as follows: 20 ml of 2xYT medium containing 100 g/ml ampicillin and 25 g/ml streptomycin were inoculated with 250 1 of an overnight culture of *E. coli* JM83 harboring the plasmid encoding the respective antibody fragment and incubated at 24.5° C. until an OD550 of 0.5 was reached. IPTG (Biomol Feinchemikalien GmbH) was added to a final concentration of 1 mM and incubation was continued for 3 hours. The OD was measured every hour, as was the b-lactamase activity in the culture supernantant to quantify the degree of cell leakiness. Three hours after induction an aliquot of the culture was removed and the cells were lysed exactly as described by Knappik and Plückthun (1995). The b-lactamase activity was measured in the supernatant, in the insoluble and in the soluble fraction. The fractions were assayed for antibody fragments by reducing SDS-PAGE, with the samples normalized to OD and b-lactamase activity to account for possible plasmid loss as well as for cell leakiness. The gels were blotted and immunostained using the FLAG antibody Ml (Prickett et al., 1989) as the first antibody, an Fc-specific anti-mouse antiserum conjugated to horseradish peroxidase (Pierce) as the second antibody, using a chemoluminescent detection assay described elsewhere (Ge et al., 1995).

(d) Purification

Mutant scFv fragments were purified by a two-column procedure. After French press lysis of the cells, the raw *E. coli* extract was first purified by IMAC (Ni-NTA superflow, Qiagen) (20 mM HEPES, 500 mM NaCl, pH 6.9; step gradient of imidazole 10, 50 and 200 mM) (Lindner et al., 1992) and, after dialyzing the IMAC eluate against 20 mM MES pH 6.0, finally purified by cation exchange chromatography (S-Sepharose fast flow column, Pharmacia) (20 mM MES, pH 6.0; salt gradient 0-500 mM NaCl). Purity was controlled by Coomassie stained SDS-PAGE. The functionality of the scFv was tested by competition ELISA.

Because of its very poor solubility in the periplasmic system, the wt 4-4-20 was expressed as cytoplasmic inclusion bodies in the T7-based system (Studier & Moffatt, 1986; Ge et al., 1995). The refolding procedure was carried out as described elsewhere (Ge et al., 1995). For purification, the refolding solution (21) was loaded over 10 h without prior dialysis onto a fluorescein affinity column, followed by a washing step with 20 mM HEPES, 150 mM NaCl, pH 7.5. Two column volumes of 1 mM fluorescein (sodium salt, Sigma Chemicals Co.) pH 7.5 were used to elute all functional scFv fragment. Extensive dialysis (7 days with 12 buffer changes) was necessary to remove all fluorescein. All purified scFv fragments were tested in gel filtration (Superose-12 column, Pharmacia SMART-System, 20 mM HEPES, 150 mM NaCl, pH 7.5).

(e) KD Determination by Fluorescence Titration

The concentrations of the proteins were determined photometrically using an extinction coefficient calculated according to Gill and von Hippel (1989). Fluorescence titration experiments were carried out by taking advantage of the intensive fluorescence of fluorescein. Two ml of 20 mM HEPES, 150 mM NaCl, pH 7.5 containing 10 or 20 nM fluorescein were placed in a cuvette with integrated stirrer. The excitation wavelength was 485 nm, emission spectra were recorded from 490 to 530 nm. Purified scFv (in 20 mM HEPES, 150 mM NaCl, pH 7.5) was added in 5 to 100 1 aliquots, and after a 3 min equilibration time a spectrum was recorded. All spectra were recorded at 20° C. The maximum of emission at 510 nM was used for determining the degree of complexation of scFv to fluorescein, seen as quenching as a function of the concentration of the antibody fragment. The KD value was determined by Scatchard analysis.

(f) Equilibrium denaturation measurement

Equilibrium denaturation curves were obtained by denaturation of 0.2 M protein in HEPES buffered saline (HBS) buffer (20 mM HEPES, 150 mM NaCl, 1 mM EDTA, pH 7.5) and increasing amounts of urea (1.0-7.5 M; 20 mM HEPES, 150 mM NaCl, pH 7.4; 0.25 M steps) in a total volume of 1.7 ml. After incubating the samples at 10° C. for 12 hours and an additional 3 hours at 20° C. prior to measurements, the fluorescence spectra were recorded at 20° C. from 320-360 nm with an excitation wavelength of 280 nm. The emission wavelength of the fluorescence peak shifted from 341 to 347 nm during denaturation and was used for determining the fraction of unfolded molecules. Curves were fitted according to Pace (1990).

(g) Thermal Denaturation

For measuring the thermal denaturation rates, purified scFv was dissolved in 2 ml HBS buffer to a final concentration of 0.5 M. The aggregation was followed for 2.5 h at 40° C. and at 44° C. by light scattering at 400 nm.

iii) Results (a) Comparison of Known Antibody Sequences

Compared to other domain/domain interfaces in proteins, the interface between immunoglobulin variable and constant domains is not very tightly packed. A comparison of 30 non-redundant Fab structures in the PDB database showed that between the light chain variable and constant domain an area of 410 ±90 Å2 per domain is buried, while the heavy chain variable and constant domains interact over an area of 710 ±180 Å2. Some, but not all of the interface residues are hydrophobic, predominantly aliphatic. Generally, sequence conservation of the residues contributing to the v/c domain interface is not particularly high. Still, the v/c domain interface shows up as a marked hydrophobic patch on the surface of an Fv fragment (FIG. 1).

Figure 2A:
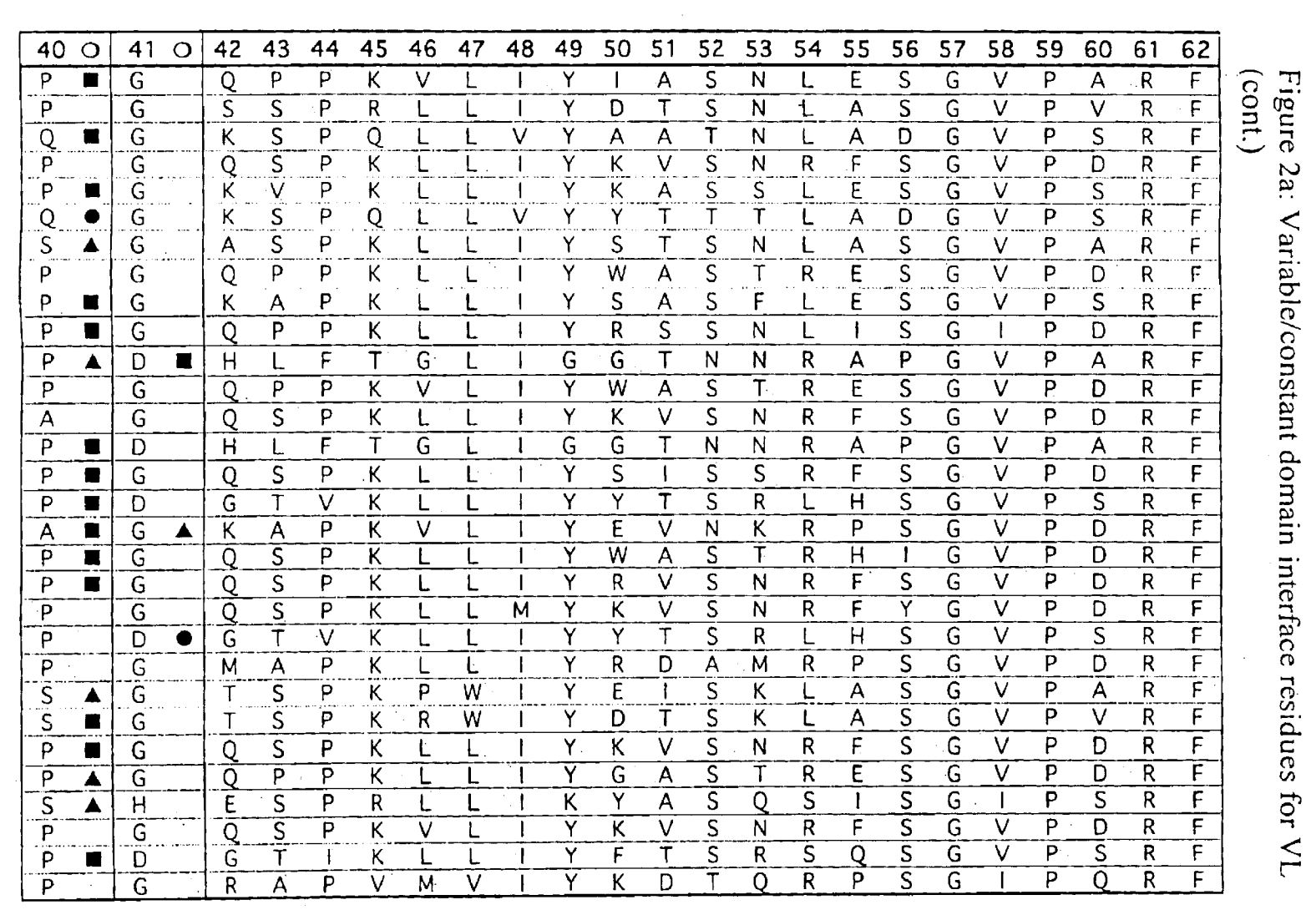
Figure 2A:
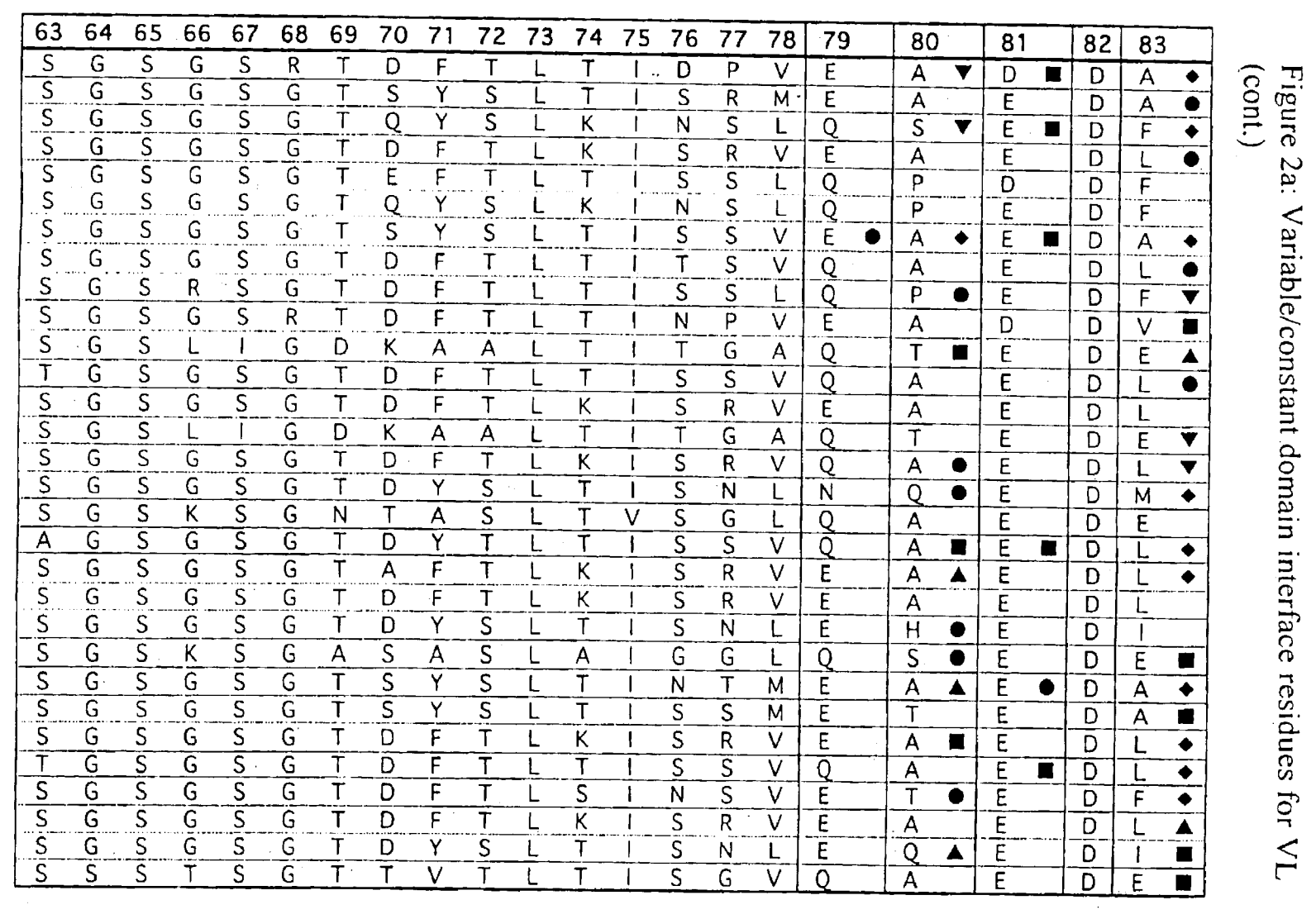
Figure 2A:
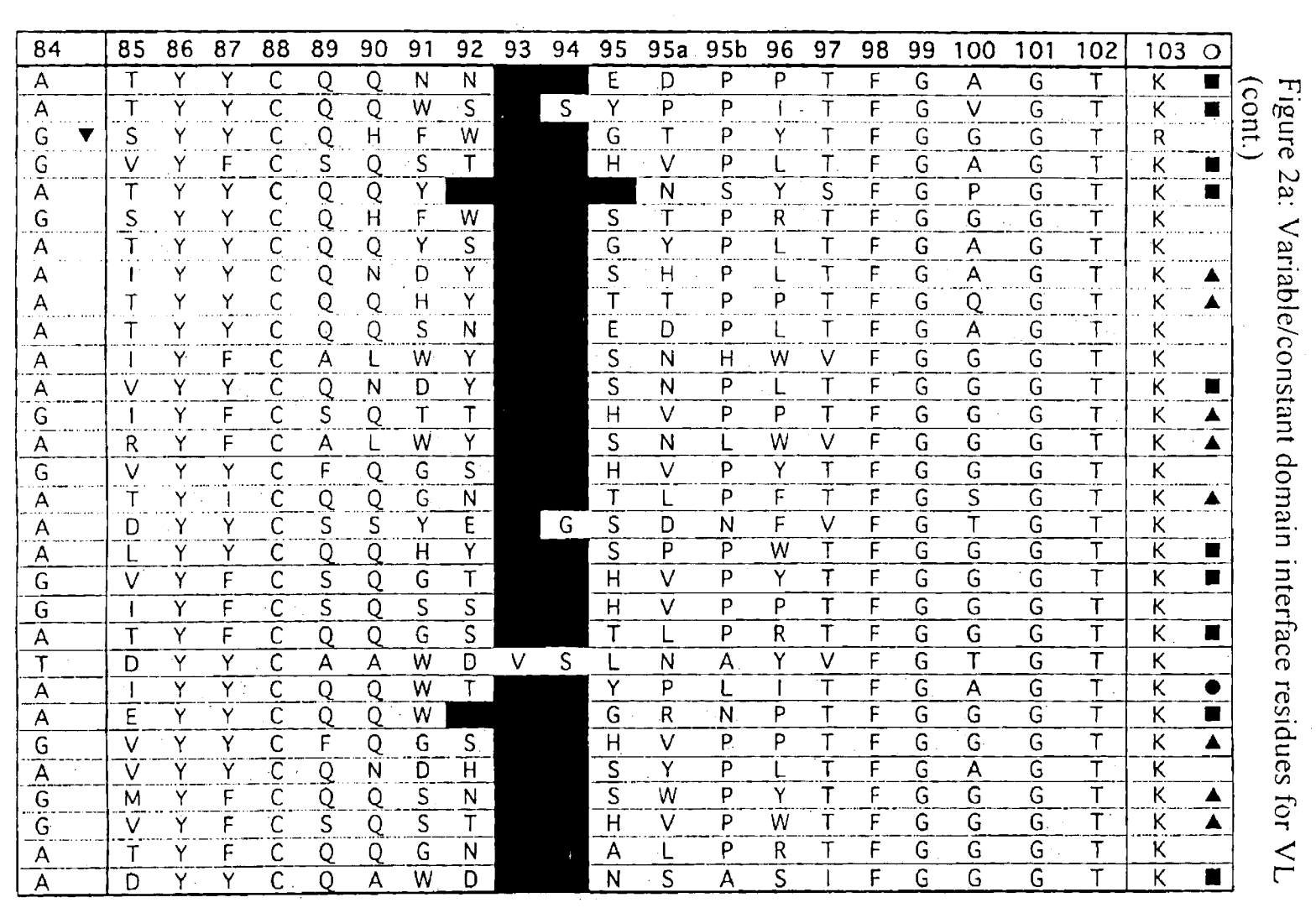
Figure 2B:
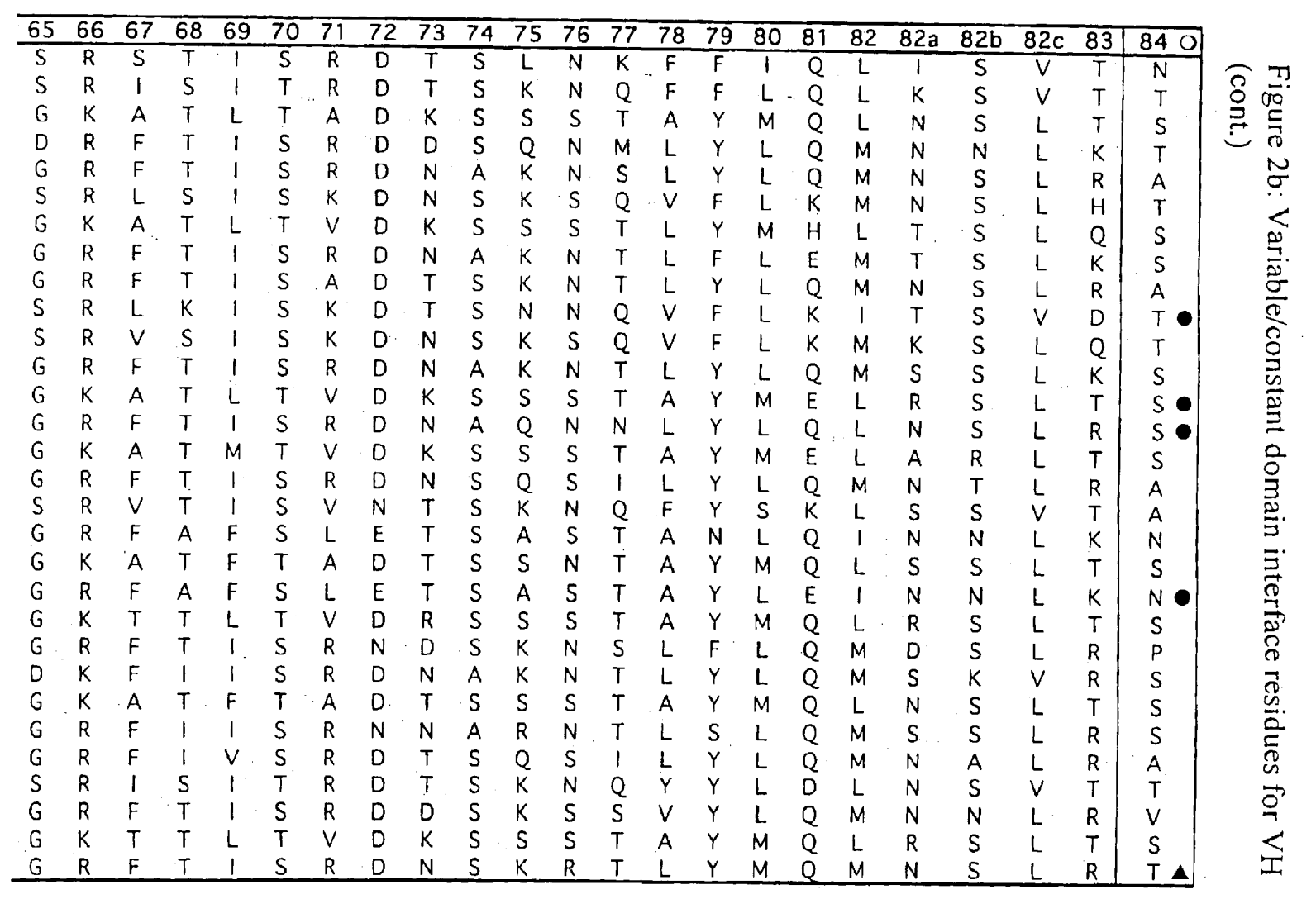

Solvent accessible surface areas for 30 non-redundant Fab fragments and their corresponding Fv fragments (derived from the Fab fragment by deleting the constant domain coordinates from the PDB file) were calculated using the program NACCESS (Lee & Richards, 1971). Residues participating in the v/c domain interface were identified by comparing the solvent-accessible surface area of each amino acid side chain in the context of an Fv fragment to its accessible surface in the context of an Fab fragment. FIG. 2 shows a plot of the relative change in side chain accessibility upon deletion of the constant domains as a function of sequence position. Residues which show a significant reduction of side chain accessibility are also highlighted in the sequence alignment. To assess sequence variability in the positions identified in FIG. 2, the variable domain sequences collected in the Kabat database (status March 1996) were analyzed (Table 1). Of the 15 interface residues identified in the VL domain of the antibody 4-4-20 (FIG. 1 and Table 1), L9(leu), L12(pro), L15(leu), L40(pro), L83(leu), and L106 (ile) are hydrophobic and therefore candidates for replacement. Of the 16 interface residues in the VH domain, Hll(leu), H14(pro), H41(pro), H84(val), H87(met) and H89 (ile) were identified as possible candidates for substitution by hydrophilic residues in the scFv fragment of the antibody 4-4-20 (FIG. 1 and Table 1).

Not all of these hydrophobic residues are equally good candidates for replacements, however. While residues which are hydrophobic in one particular sequence but hydrophilic in many other sequences may appear most attractive, the conserved hydrophobic residues listed in Table 1 have also been investigated, since the evolutionary pressure which kept these conserved residues acted on the Fab fragment within the whole antibody, but not the isolated Fv portion. In this study, we did not replace the proline residues since proL40 and pro H41 form the hairpin turns at the bottom of the framework II region, while the conserved VL cis-proline L8 and proline residues H9 and H14 determine the shape of framework I of the immunoglobulin variable domains.

Excluding prolines, this leaves residues L9 (leu in 4-4-20, ser in most kappa chains), L15 (leu, usually hydrophobic), L83 (leu, usually val or phe) and L106 (Ile, as in 86% of all kappa chains) in the VL domain and Hll (leu as in 60% of all heavy chains), H84 (val, in other VH domains frequently ala or ser), H87 (met, usually ser) and H89 (ile, most frequently val) in VH as possible candidates for replacement in the 4-4-20 scFv fragment.

(b) Mutations in the 4-4-20 scFv

For the 4-4-20 scFv fragment some of the crucial residues identified in the sequence analysis described above are already hydrophilic, but nevertheless 9 residues are of hydrophobic nature (including pro12 in the light chain) (Table 1). We chose three residues for closer analysis by mutations.

Leu15 in VL is a hydrophobic amino acid in 98% of all kappa chains (Table 1). Leu11 is conserved in VH (Table 1) and is involved in v/c interdomain contacts (Lesk & Chothia, 1988). In contrast, valine occurs very infrequently at position H84; mainly found at this position are threonine and serine and alanine (Table 1). As can be seen in FIG. 1, val84 is contributing to a large hydrophobic patch at the newly exposed surface of VH. All three positions were mutated into acidic residues, and L11 was also changed to asparagine (Table 2).

The scFv fragment was tested and expressed with two different linkers, the 15-mer linker (Gly4Ser)3 (Huston et al., 1995) and the same motif extended to 30 amino acids (Gly4Ser)6. All mutations were tested in both constructs. The in vivo results of the different mutations on solubility were identical, and therefore only the results of the 30-mer linker are described in more detail. The periplasmic expression experiments were carried out at 24.5° C., and all constructs were tested for soluble and insoluble protein by immunoblotting. The ratio of insoluble to soluble (i/s) protein was determined for every mutant. In FIG. 3 A–D, insoluble (lane 1) and soluble (lane 2) fractions of the wt scFv are shown. Nearly no soluble material occurs in periplasmic expression, which is consistent with previous reports of Bedzyk et al. (1990) and Denzin et al. (1991), who described earlier that the periplasmic expression of the wt scFv leads mainly to periplasmic inclusion bodies.

The single point mutation L15E in VL (Flu1) shows no effect on the ratio i/s when compared with the wt (FIG. 3A, lane 3, 4). Mutating leu at position 11 in the heavy chain to asparagine (Flu2) also shows nearly no effect compared to the wt, whereas the subtitution with aspartic acid (Flu3) changes the i/s ratio to more soluble protein, but still this effect is not very dramatic. In contrast, the point mutation at position 84 (Flu4, FIG. 3B, lane 3, 4 and FIG. 3D, lane 3, 4) had a dramatic influence on the solubility of the scFv fragment of the antibody 4-4-20. The ratio i/s is changed to about 1:1, resulting in a 25-fold increase of soluble protein compared to the wt.

The combination of V84D with L1N or L11D (Flu5, Flu6) also changes the ratio i/s compared to the wt, but this ratio compared to V84D alone is not improved further (FIG. 3B). Interestingly, the combination of Flu5 with the light chain mutation at position 15 (Flu9) leads to less soluble material (FIG. 3C lane 7,8) than Flu5 itself (FIG. 3B, lane 5, 6). The negative influence of the L15E mutations can also be seen in Flu8 (FIG. 3C, lane 5, 6) compared with Flu3 (FIG. 3A, lane 7, 8). In FIG. 3D the comparison of the wt (lane 1, 2 and 5, 6) and Flu4 (lane 3, 4 and 7, 8) is shown in both the 15-mer and the 30-mer construct.

The negative effect of L15E can be rationalized by looking at a model of the 4-4-20 scFv fragment. L15 is forming a hydrophobic pocket together with residues A80, L83, and L106. Apparently, L15 stabilizes the scFv fragment by hydrophobic interactions with its closest neighbours. Thus the exchange L15E for making the scFv fragment more hydrophilic and more soluble is made at the expense of the fragment stability. The analysis of hydrophobic interactions within a fragment should thereby by used to choose the solvent-exposed residues to be mutated in the case of any other antibody fragment. Combinations of various serine mutations in VH led to further improvements in the i/s ratio. The mutants FH15 (V84S, M87S, I89S) and FH20 (L11S, v84s, M87S, I89S) both showed more than 70% of soluble protein in immunoblots (data not shown). The negative effect of L15E (c) Functional Expression and Purification The oligomerization of scFv fragments as a function of linker length has been investigated previously. A continuous decrease in the amount of dimer and multimer formation as a function of linker length has been reported (Desplancq et al., 1994; Whitlow et al., 1994). While the (Gly4Ser)3 linker has been shown to lead to monomeric scFvs in many cases in the VH-VL direction, this is often not the case in the VL-VH direction. This is caused by an asymmetry in the VL/VH arrangement, leading to a longer distance between the end of VH and the N-terminus of VL than between C-terminus of VL and N-terminus of VH (Huston et al., 1995). Consequently, a linker of identical length may lead to different properties of the resulting molecules.

Since we have chosen to use the minimal pertubation FLAG (Knappik & Plückthun, 1994) at the N-terminus of VL in our constructs and thus the VL-linker-VH orientation, we have investigated the use of longer linkers. In the periplasmic expression in E. coli no difference between the 15-mer and the 30-mer linker in the corresponding mutants is visible (FIG. 3D), but when we attempted to purify the two Flu4 scFvs with long and short linker, a big discrepancy between the two constructs was found. The purification of the Flu4 mutant (V84D) with the 15-mer linker leads to very small amounts of partially purified protein (about 0.015 mg per liter and OD; estimated from SDS-PAGE after IMAC purification), whereas the 30-mer linker construct gives about 0.3 mg per liter and OD of highly pure functional protein. All mutants with 30-mer linker were tested in gel filtration and found to be monomeric (data not shown).

For further in vitro characterization five mutants were purified with the 30-mer linker, V84D (Flu4), V84D/L11D (Flu6), L11D (Flu3), and the serine mutants FH15 and FH20 (see iii(b)). A two-step chromatography, first using IMAC and then cation-exchange chromatography, led to homogeneous protein. The i/s ratio of the antibody fragments (FIG. 3) was also reflected in the purification yield of functional protein. The highly soluble mutant Flu4 (V84D) (FIG. 3B lane 3, 4) yielded about 0.3 mg purified and functional protein per liter and OD, Flu6 (L11D/V84D) (FIG. 3B lane 7, 8) yielded about 0.25 mg per liter and OD and Flu3 (less soluble material on the blot in FIG. 3A lane 7, 8) yielded 0.05 mg per liter and OD. The serine mutants FH15 and FH20 yielded 0.3 mg and 0.4 mg per liter and OD, respectively. The wt scFv of the antibody 4-4-20 did not give any soluble protein at all in periplasmic expression with either linker, and it was therefore expressed as cytoplasmic inclusion bodies, followed by refolding in vitro and fluorescein affinity chromatography. The refolded wt scFv was shown by gel filtration to be monomeric with the 30-mer linker (data not shown).

(d) Biophysical Properties of the Mutant scFvs

Since we changed amino acids which are conserved, it cannot be excluded that changes at these positions may be transmitted through the structure and have an effect on the binding constant, even though they are very far from the binding site (Chatellier et al., 1996). To eliminate this possibility, we determined the binding constant of the mutants Flu3, Flu4, Flu6 and the wt scFv. Fluorescence titration was used to determine KD in solution by using the quenching of the intrinsic fluorescence of fluorescein when it binds to the antibody. The fluorescence quenching at 510 nm was measured as a function of added scFv. The KD values (Table 3 and FIG. 4) obtained for all three mutant scFvs and the wt scFv are very similar and correspond very well to the recently corrected KD of the monoclonal antibody 4-4-20 (Miklasz et al., 1995).

To determine whether the mutations had an influence on the thermodynamic stability of the protein we determined the equilibrium unfolding curves by urea denaturation. V84D mutant and the wt scFv were used for this analysis, and in FIG. 5 an overlay plot is shown. The midpoint of both curves is at 4.1 M urea. Both curves were fitted by an algorithm for a two-state model described by Pace (1990), but the apparent small difference between the V84D mutant and the wt scFv is not of statistical significance. Aggregation of folding intermediates could be another explanation for the different in vivo results between the mutant scFvs and the wt scFv (FIG. 3). In the periplasm of *E. coli*, the protein concentrations are assumed to be rather high (van Wielink & Duine, 1990) and the aggregation effects could thus be pronounced. In order to estimate the aggregation behavior in vitro, we have measured the thermal aggregation rates at different temperatures. In FIG. 6 it is clearly seen that the wt scFv is significantly aggregating already at 44° C., whereas the mutant V84D tends to aggregate more slowly. The wt scFv is thus clearly more aggregation prone than the mutant scFv. This is very similar to the observations made with different mutations on the antibody McPC603 (Knappik and Plückthun, 1995), where no correlation was found between equilibrium denaturation curves and expression behavior, but a good correlation was found with the thermal aggregation rates.

OTHER PUBLICATIONS

Better, M., Chang, P., Robinson, R. & Horwitz, A. H. (1988). *E. coli* secretion of an active chimeric antibody fragment. Science 240, 1041–1043.

Bird, R. E., Hardman, K. D., Jacobson, J. W., Johnson, S., Kaufman, B. M., Lee S. M., Lee T., Pope S. H., Riordan G. S., & Whitlow M. (1988). Single-chain antigen-binding proteins [published erratum appears in (1989). Science 244, 4091]. Science 242, 423–6.

Bedzyk, W. D., Weidner, K. M., Denzin, L. K., Johnson, L. S., Hardman, K. D., Pantoliano, M. W., Asel, E. D. & Voss, E. W., Jr. (1990). Immunological and structural characterization of a high affinity anti-fluorescein single-chain antibody. J. Biol. Chem. 265, 18615–18620.

Blake, M. S., Johnston, K. H., Russel-Jones, G. J. & Gotschlich, E. C. (1984). A rapid, sensitive method for detection of alkaline phosphatase-conjugated anti-antibody on Western blots. Anal. Biochem. 136, 175–179.

Brinkmann, U., Reiter, Y., Jung, S., Lee, B. & Pastan, I. (1993). A recombinant immunotoxin containing a disulfide-stabilized Fv fragment. Proc. Natl. Acad. Sci. U.S.A. 90, 7538∝7542.

Carter, P., Kelley, R. F., Rodrigues, M. L., Snedecor, B., Covarrubias, M., Velligan, M. D., Wong, W. L. T., Rowland, A. M., Kotts, C. E., Carver, M. E., Yang, M., Bourell, J. H., Shepard, H. M. & Henner, D. (1992). High level *Escherichia coli* expression and production of a bivalent humanized antibody fragment. Bio/Technology 10, 163–167.

Casari, G. & Sippl, M. J. (1992). Structure-derived hydrophobic potential. Hydrophobic potential derived from X-ray structures of globular proteins is able to identify native folds. J. Mol. Biol., 224, 725–32.

Chatellier, J., van Regenmortel, M. H. V., Vernet, T. & Altschuh, D. (1996). Functional mapping of conserved residues located at the VL and VH domain interface of an Fab. J. Mol. Biol., in press.

Denzin, L. K., Whitlow, M & Voss, E. W., Jr. (1991). Single-chain site-specific mutation of fluorescein-amino acid contact residues in high affinity monoclonal antibody 4-4-20. J. Biol. Chem. 266, 14095–14102.

Desplancq, D., King, D. J., Lawson, A. D. & Mountain, A. (1994). Multimerization behaviour of single chain Fv variants for the tumour-binding antibody B72.3. Protein Eng. 7, 1027–1033.

Ge, L., Knappik, A., Pack, P., Freund, C. & Plückthun, A. (1995). Expressing antibodies in *Escherichia coli*. Antibody Engineering. A Practical Approach (Ed. C.A.K. Borrebaeck). IRL Press, Oxford, pp. 229–266.

Gething, M. J. & Sambrook, J. (1992). Protein folding in the cell. Nature 355, 33–45.

Gill, S. C. von Hippel, P. H. (1989). Calculation of protein extinction coefficients from amino acid sequence data. Anal. Biochem. 182, 319–326.

Glockshuber, R., Malia, M., Pfitzinger, I. & Plückthun, A. (1992). A comparison of strategies to stabilize immunoglobulin Fv-fragments. Biochemistry 29, 1362–1366.

Hiatt,. A. (1990). Antibodies produced in plants. Nature 344, 469–470.

Hiatt, A. & Ma, J. K. (1993). Characterization and applications of antibodies produced in plants. Int. Rev. Immunol. 10, 139–152.

S. N., nt, H. D., Horton, R. M., Pullen, J. K. & Pease, L. R. (1989). Site-directed mutagenesis by overlap extension using the polymerase chain reaction. Gene 77, 51–9.

Hochuli, E., Bannwarth, W., Ddbeli, H., Gentz, R. & Stuber, D. (1988). Genetic approach to facilitate purification of recombinant proteins with a novel metal chelate adsorbent. Bio/Technology 6, 1321–1325.

Hopp, T. P., Prickett, K. S.,Price V. L., Libby, R. T., March, C. J., Cerretti, D. P., Urdal, D. L. & Conlon, P. J. (1988). A short polypeptide marker sequence useful for recombinant protein identification and purification. Bio/Technology 6, 1204–1210.

Horwitz, A. H., Chang, C. P., Better, M., Hellstrom, K. E. & Robinson, R. R. (1988). Secretion of functional antibody and Fab fragment from yeast cells. Proc. Natl. Acad. Sci. U.S.A. 85, 8678–8682.

Huston, J., George, A. J. T., Tai, M., McCartney, J. E., Jin, D., Segal, D.M., Keck, P. & Oppermann, H. (1995). Single-chain Fv design and production by preparative folding. Antibody Engineering. A Practical Approach (Ed. C.A.K. Borrebaeck). IRL Press, Oxford, pp. 185–228.

Huston, J. S., Levinson, D., Mudgett-Hunter, M., Tai, M. S., Novotny, J., Margolies, M. N., Ridge, R. J., Bruccoleri, R. E., Haber, E. & Crea, R. (1988). Protein engineering of antibody binding sites recovery of specific activity in an anti-digoxin single-chain Fv analogue produced in *Escherichia coli*. Proc. Natl. Acad. Sci. U. S. A. 85, 5879–83.

Johnson, K. S., Jackson, R. H. & Chiswell, D. J. (1992). Binding Domains. PCT Application WO92/01787.

Kabat, E. A., Wu, T. T., Perry, H. M., Gottesmann, K. S. & Foeller, C. (1991). Sequences of proteins of immunological interest. U.S. Dept. of Health and Human Services, Public Health Service, National Institutes of Health. NIH Publication 91–3242.

Knappik, A. & Plückthun, A. (1994). An improved affinity tag based on the FLAG peptide for detection and purification of recombinant antibody fragments. BioTechniques 17, 754–761.

Knappik, A. & Plückthun, A. (1995). Engineered turns of a recombinant antibody improve its in vivo folding. Protein Eng. 8, 81–89.

Kunkel, T. A., Bebenek, K. & McClary, J. (1991). Efficient site-directed mutagenesis using uracil-containing DNA. Methods in Enzymol. 204, 125–39.

Kunkel, T. A., Roberts, J. D. & Zakour, R. A. (1987). Rapid and efficient site-specific mutagenesis without phenotypic selection. Methods in Enzymol. 154: 367–382.

Lee, B. & Richards, F. M. (1971). The interpretation of protein structures: estimation of static accessibility. J. Mol. Biol. 55, 379–400.

Lesk, A. M. & Chothia, C. (1988). Elbow motion in the immunoglobulins involves a molecular ball-and-socket joint. Nature (London) 335,188–190.

Leistler, B. & Perham, R. N. (1994). Solubilizing buried domain proteins: A self-assembling interface domain from glutathione reductase. Biochemistry 33, 2773–2781.

Lindner, P., Guth, B., Wülfing, C., Krebber, C., Steipe, B., Müller, F. & Plückthun, A. (1992). Purification of native proteins from the cytoplasm and periplasm of *Escherichia coli* using IMAC and histidine tails: a comparison of proteins and protocols. Methods: A Companion to Methods Enzymol. 4, 41–56.

Miklasz, S. D., Gulliver, G. A. & Voss, E. W., Jr. (1995). High-affinity rat anti-fluorescein monoclonal antibody with unique fine specificity properties including differential recognition of dynamic ligand analogues. J. Mol. Recognition 8, 258–269.

Munro, S. & Pelham, H. R. B. (1986). An Hsp70-like protein in the ER: identity with the 78 kd glucose-regulated protein and immunoglobulin heavy chain binding protein. Cell, 46, 291–300.

Nozaki, Y. & Tanford, C. (1971). The solubility of amino acids and two glycine peptides in aqueous ethanol and dioxaneolutions. Establishment of a hydrophobicity scale. J. Biol. Chem. 246, 2211–7.

Nyyssonen, E., Penttila, M., Harkki, A., Saloheimo, A., Knowles, J. K. & Keranen, S. (1993). Efficient production of antibody fragments by the filamentous fungus *Trichoderma reesei*. Bio/Technology 11, 591–595.

Pace, C.N. (1990). Measuring and increasing protein stability. Trends Biotechnol. 8,93–98. Pack, P. & Plückthun, A. (1992). Miniantibodies: use of amphipathic helices to produce functional, flexibly linked dimeric Fv fragments with high avidity in *Escherichia coli*. Biochemistry 31, 1579–1584.

Pack, P., Kujau, M., Schroeckh, V., Knüpfer, U., Wenderoth, R., Riesenberg D. & Plückthun, A. (1993). Improved bivalent miniantibodies, with identical avidity as whole antibodies, produced by high cell density fermentation of in *Escherichia coli*. Bio/Technology 11, 1271–1277.

Pack, P. (1994). Mini-Antikörper: Bivalente, tetravalente und bispezifische Immunglobuline aus *E. coli*. Ph.D. thesis, Ludwig-Maximilians-Universität München.

Plückthun, A. (1992). Mono- and bivalent antibody fragments produced in *Escherichia coli*: engineering, folding and antigen binding. Immun. Rev. 130,151–188.

Plückthun, A., Krebber, A., Krebber, C., Horn, U., Knüpfer, U., Wenderoth, R., Nieba, L., Proba, K. & Riesenberg, D. (1996). Producing antibodies in *Escherichia coli*: From PCR to fermentation. A practical apprach. Antibody Engineering (Ed. J. McCafferty). IRL Press, Oxford, pp. 203–252.

Potter, K. N., Li, Y. & Capra, J. D. (1993). Antibody production in the baculovirus expression system. Int. Rev. Immunol. 10, 103–112.

Prickett, K. S., Amberg, D.C. & Hopp, T. P. (1989). A calcium-dependent antibody for identification and purification of recombinantproteins. BioTechniques 7, 580–589.

Prodromou, C. & Pearl, L.H. (1992). Recursive PCR: a novel technique for total gene synthesis. Protein Eng. 5, 827–829.

Ridder, R., Schmitz, R., Legay, F. & Gram, H. (1995). Generation of rabbit monoclonal antibody fragments from a combinatorial phage display library and their production in the yeast *Pichia pastoris*. Bio/Technology 13, 255–260.

Rose, G. D. & Wolfenden, R. (1993). Hydrogen bonding, hydrophobicity, packing, and protein folding. Annu Rev. Biophys. Biomol. Struct. 22, 381–415.

Rosenberg, S. A. & Lotze, M. T. (1986). Cancer immunotherapy using interleukin-2 and interleukin-2 activated lymphocytes. Ann. Rev. Immunol. 4, 681–709.

Skerra, A. & Plückthun(1988). Assembly of a functional immunoglobulin Fv fragment in *Escherichia coli*. Sclence 240, 1038–1041.

Studier, F. W. & Moffatt, B. A. (1986). Use of bacteriophage T7 RNA polymerase to direct selective high-level expression of cloned genes. J. Mol. Biol. 189, 113–130.

Trill, J. J., Shatzman, A. R. & Ganguly, S. (1995). Production of monoclonal antibodies in COS and CHO cells. Curr. 9pin. Biotechnol. 6, 553–560.

Trower,. M. K. (1994). Site-directed mutagenesis using a uracil-containing phagemid template. Methods Mol. Biol. 31, 67–77.

Ullrich, H. D., Patten, P. A., Yang, P. L., Romesberg, F. E. & Schultz, P. G. (1995). Expression studies of catalytic antibodies. Proc. Natl. Acad. Sci. USA 92, 11907–11911.

Van Wielink, J. E. & Duine, J. A. (1990). How big is the periplasmic space. Trends Biochem. Sci. 15, 136–137.

Vitetta, E. S., Thorpe, P. E. & Uhr, J. (1993). Immunotoxins: magic bullets or misguided missiles. Immunol. Today 14, 253–259.

Viville, S. (1994). Site-directed mutagenesis using a double-stranded DNA template. Methods Mol. Biol. 31, 57–65.

Ward, V. K., Kreissig, S. B., Hammock, B. D. & Choudary, P. V. (1995). Generation of an expression library in the baculovirus expression vector system. J. Virol. Methods 53, 263–272.

Whitelam, G. C., Cockburn, W. & Owen, M. R. (1994). Antibody production in transgenic plants. Biochem. Soc. Trans. 22, 940–944.

Whitlow, M., Filupa, D., Rollence, M. L., Feng, S. & Wood, J. F. (1994). Multivalent Fvs: characterization of single-chain Fv oligomers and preparation of a bispecific Fv. Protein Eng. 7, 1017–1026.

Wu, X. C., Ng, S. C., Near, R. I. & Wong, S. L. (1993). Efficient production of a functional single-chain anti-digoxin antibody via an engineered *Bacillus subtilis* expression-secretion system. Bio/Technology 11, 71–76.

---

SEQUENCE LISTING

<160> NUMBER OF SEQ ID NOS: 60

<210> SEQ ID NO 1
<211> LENGTH: 113
<212> TYPE: PRT
<213> ORGANISM: Murine

<400> SEQUENCE: 1

```
Asp Ile Val Met Thr Gln Ser Pro Ala Ser Leu Val Ser Leu Gly
 1               5                  10                  15
Gln Arg Ala Thr Ile Ser Cys Arg Ala Ser Glu Ser Val Asp Ser Tyr
            20                  25                  30
Gly Lys Ser Phe Met His Trp Tyr Gln Gln Lys Pro Gly Gln Pro Pro
            35                  40                  45
Lys Val Leu Ile Tyr Ile Ala Ser Asn Leu Glu Ser Gly Val Pro Ala
        50                  55                  60
Arg Phe Ser Gly Ser Gly Ser Arg Thr Asp Phe Thr Leu Thr Ile Asp
 65                 70                  75                  80
Pro Val Glu Ala Asp Asp Ala Ala Thr Tyr Tyr Cys Gln Gln Asn Asn
                85                  90                  95
Glu Asp Pro Pro Pro Thr Phe Gly Ala Gly Thr Lys Leu Glu Met Arg
            100                 105                 110
Arg
```

<210> SEQ ID NO 2
<211> LENGTH: 108
<212> TYPE: PRT
<213> ORGANISM: Murine

<400> SEQUENCE: 2

```
Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Tyr Tyr Met
            20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
 65                 70                  75                  80

Asp Ala Ala Thr Tyr Tyr Cys Gln Gln Trp Ser Ser Tyr Pro Pro Ile
                85                  90                  95

Thr Phe Gly Val Gly Thr Lys Leu Asp Leu Lys Thr
            100                 105
```

<210> SEQ ID NO 3
<211> LENGTH: 108
<212> TYPE: PRT
<213> ORGANISM: Murine

<400> SEQUENCE: 3

```
Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
 65                 70                  75                  80

Glu Asp Phe Gly Ser Tyr Tyr Cys Gln His Phe Trp Gly Thr Pro Tyr
                85                  90                  95

Thr Phe Gly Gly Gly Thr Arg Leu Glu Ile Lys Arg
            100                 105
```

<210> SEQ ID NO 4
<211> LENGTH: 113
<212> TYPE: PRT
<213> ORGANISM: Murine

```
<400> SEQUENCE: 4

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Tyr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

Arg

<210> SEQ ID NO 5
<211> LENGTH: 106
<212> TYPE: PRT
<213> ORGANISM: Homo sapiens

<400> SEQUENCE: 5

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Val Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Gly Pro Gly Thr Lys Val Asp Ile Lys Arg
            100                 105

<210> SEQ ID NO 6
<211> LENGTH: 108
<212> TYPE: PRT
<213> ORGANISM: Murine

<400> SEQUENCE: 6

Asp Ile Gln Met Thr Gln Ser Pro Ala Ser Leu Ser Ala Ser Val Gly
 1               5                  10                  15

Glu Thr Val Thr Ile Thr Cys Thr Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Tyr Thr Thr Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
```

85                  90                  95

Thr Phe Gly Gly Gly Thr Lys Leu Glu Ile Lys Arg
            100                 105

<210> SEQ ID NO 7
<211> LENGTH: 109
<212> TYPE: PRT
<213> ORGANISM: Murine

<400> SEQUENCE: 7

Glu Asn Val Leu Thr Gln Ser Pro Ala Ile Met Ser Ala Ser Pro Gly
  1               5                  10                  15

Glu Lys Val Thr Met Ala Cys Arg Ala Ser Ser Ser Val Ser Ser Thr
             20                  25                  30

Tyr Leu His Trp Tyr Gln Gln Lys Ser Gly Ala Ser Pro Lys Leu Leu
         35                  40                  45

Ile Tyr Ser Thr Ser Asn Leu Ala Ser Gly Val Pro Ala Arg Phe Ser
     50                  55                  60

Gly Ser Gly Ser Gly Thr Ser Tyr Ser Leu Tyr Ile Ser Ser Val Glu
 65                  70                  75                  80

Ala Glu Asp Ala Ala Thr Tyr Tyr Cys Gln Gln Tyr Ser Gly Tyr Pro
                 85                  90                  95

Leu Thr Phe Gly Ala Gly Thr Lys Leu Glu Leu Lys Arg
            100                 105

<210> SEQ ID NO 8
<211> LENGTH: 114
<212> TYPE: PRT
<213> ORGANISM: Murine

<400> SEQUENCE: 8

Asp Ile Val Met Thr Gln Ser Pro Ser Ser Leu Thr Val Thr Ala Gly
  1               5                  10                  15

Glu Lys Val Thr Met Ser Cys Lys Ser Ser Gln Ser Leu Phe Asn Ser
             20                  25                  30

Gly Lys Arg Lys Asn Phe Leu Thr Trp Tyr His Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Thr Ser Val Gln Ala Glu Asp Leu Ala Ile Tyr Tyr Cys Gln Asn
                 85                  90                  95

Asp Tyr Ser His Pro Leu Thr Phe Gly Ala Gly Thr Lys Leu Glu Leu
            100                 105                 110
    Lys Arg

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Humanized
      murine

<400> SEQUENCE: 9

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala

```
                20                  25                  30
Val Ala Trp Tyr Gln Gln Lys Pro Gly Lys Ala Pro Lys Leu Leu Ile
         35                  40                  45

Tyr Ser Ala Ser Phe Leu Glu Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg
            100                 105

<210> SEQ ID NO 10
<211> LENGTH: 112
<212> TYPE: PRT
<213> ORGANISM: Murine

<400> SEQUENCE: 10

Asp Ile Val Leu Thr Gln Ser Pro Gly Ser Leu Ala Val Ser Leu Gly
 1               5                  10                  15

Gln Arg Ala Thr Ile Ser Cys Arg Ala Ser Gln Ser Val Asp Asp Asp
                 20                  25                  30

Gly Asn Ser Phe Leu His Trp Tyr Gln Gln Lys Pro Gly Gln Pro Pro
             35                  40                  45

Lys Leu Leu Ile Tyr Arg Ser Ser Asn Leu Ile Ser Gly Ile Pro Asp
 50                  55                  60

Arg Phe Ser Gly Ser Gly Ser Arg Thr Asp Phe Thr Leu Thr Ile Asn
 65                  70                  75                  80

Asp Pro Val Glu Ala Asp Val Ala Thr Tyr Tyr Cys Gln Gln Ser Asn
                 85                  90                  95

Gln Asp Pro Leu Thr Phe Gly Ala Gly Thr Lys Leu Glu Ile Lys Arg
            100                 105                 110

<210> SEQ ID NO 11
<211> LENGTH: 111
<212> TYPE: PRT
<213> ORGANISM: Murine

<400> SEQUENCE: 11

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
                 20                  25                  30

Asn Tyr Ala Asn Trp Tyr Gln Glu Lys Pro Asp His Leu Phe Thr Gly
             35                  40                  45

Leu Ile Glu Glu Thr Asn Asn Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu Gly
            100                 105                 110

<210> SEQ ID NO 12
<211> LENGTH: 114
<212> TYPE: PRT
```

<213> ORGANISM: Murine

<400> SEQUENCE: 12

```
Asp Ile Val Met Thr Gln Ser Pro Ser Ser Leu Thr Val Thr Ala Gly
  1               5                  10                  15

Glu Lys Val Thr Met Ser Cys Thr Ser Ser Gln Ser Leu Phe Asn Ser
             20                  25                  30

Gly Lys Gln Lys Asn Tyr Leu Thr Trp Tyr Gln Gln Lys Pro Gly Gln
         35                  40                  45

Pro Pro Lys Val Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Asn Pro Leu Thr Phe Gly Gly Gly Thr Lys Leu Glu Leu
            100                 105                 110

Lys Arg
```

<210> SEQ ID NO 13
<211> LENGTH: 113
<212> TYPE: PRT
<213> ORGANISM: Murine

<400> SEQUENCE: 13

```
Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
             20                  25                  30

Asn Gly Asn Thr Tyr Leu Asn Trp Tyr Leu Gln Lys Ala Gly Gln Ser
         35                  40                  45

Pro Lys Leu Leu Ile Tyr Lys Val Ser Asn Arg Phe Ser Gly Val Pro
     50                  55                  60

Asp Thr Phe Ser Gly Ser Gly Ser Gly Thr Asp Phe Thr Leu Lys Ile
 65                  70                  75                  80

Ser Arg Val Glu Ala Glu Asp Leu Gly Ile Tyr Phe Cys Ser Gln Thr
                 85                  90                  95

Thr His Val Pro Pro Thr Phe Gly Gly Gly Thr Lys Leu Glu Ile Lys
            100                 105                 110

Arg
```

<210> SEQ ID NO 14
<211> LENGTH: 109
<212> TYPE: PRT
<213> ORGANISM: Murine

<400> SEQUENCE: 14

```
Ala Val Val Thr Gln Glu Ser Ala Leu Thr Thr Ser Pro Gly Glu Thr
  1               5                  10                  15

Val Thr Leu Thr Cys Arg Ser Ser Thr Gly Ala Val Thr Thr Ser Asn
             20                  25                  30

Tyr Ala Asn Trp Tyr Gln Glu Lys Pro Asp His Leu Phe Thr Gly Leu
         35                  40                  45

Ile Gly Gly Thr Asn Asn Arg Ala Pro Gly Val Pro Ala Arg Phe Ser
     50                  55                  60

Gly Ser Leu Ile Gly Asp Lys Ala Ala Leu Thr Ile Thr Gly Ala Gln
```

```
            65                  70                  75                  80
Thr Glu Asp Glu Ala Arg Tyr Phe Cys Ala Leu Trp Tyr Ser Asn Leu
                    85                  90                  95

Trp Val Phe Gly Gly Gly Thr Lys Leu Thr Val Leu Gly
                100                 105

<210> SEQ ID NO 15
<211> LENGTH: 113
<212> TYPE: PRT
<213> ORGANISM: Murine

<400> SEQUENCE: 15

Asp Val Leu Met Thr Gln Thr Pro Ile Ser Ile Pro Val Ser Leu Gly
 1               5                   10                  15

Asp Gln Ala Ser Ile Ser Cys Arg Ser Ser Gln Ser Ile Val His Gly
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Ser Ile Ser Ser Arg Phe Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Gln Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Thr

<210> SEQ ID NO 16
<211> LENGTH: 108
<212> TYPE: PRT
<213> ORGANISM: Murine

<400> SEQUENCE: 16

Asp Ile Gln Met Thr Gln Thr Thr Ser Ser Leu Ser Ala Ser Leu Gly
 1               5                   10                  15

Asp Arg Val Thr Ile Ser Cys Arg Ala Ser Gln Asp Ile Tyr Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Asn Gln
 65                 70                  75                  80

Glu Asp Met Ala Thr Tyr Ile Cys Gln Gln Gly Asn Thr Leu Pro Phe
                85                  90                  95

Thr Phe Gly Ser Gly Thr Lys Leu Glu Ile Lys Arg
                100                 105

<210> SEQ ID NO 17
<211> LENGTH: 111
<212> TYPE: PRT
<213> ORGANISM: Homo sapiens

<400> SEQUENCE: 17

Pro Ser Ala Leu Thr Gln Pro Pro Ser Ala Ser Gly Ser Leu Gly Gln
 1               5                   10                  15
```

Ser Val Thr Ile Ser Cys Thr Gly Thr Ser Ser Asp Val Gly Gly Tyr
            20                  25                  30

Asn Tyr Val Ser Trp Tyr Gln Gln His Ala Gly Lys Ala Pro Lys Val
            35                  40                  45

Leu Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Glu Gly Ser
                85                  90                  95

Asp Asn Phe Val Phe Gly Thr Gly Thr Lys Val Thr Val Leu Gly
            100                 105                 110

<210> SEQ ID NO 18
<211> LENGTH: 108
<212> TYPE: PRT
<213> ORGANISM: Anous minutus
<220> FEATURE:
<223> OTHER INFORMATION: Noddy Tern

<400> SEQUENCE: 18

Asp Ile Val Met Thr Gln Ser Pro Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Val Trp Tyr Gln Gln Lys Pro Gly Gln Ser Pro Lys Leu Leu Ile
            35                  40                  45

Tyr Trp Ala Ser Thr Arg His Ile Gly Val Pro Asp Arg Phe Ala Gly
        50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Pro Pro Trp
                85                  90                  95

Thr Phe Gly Gly Gly Thr Lys Leu Glu Ile Lys Arg
            100                 105

<210> SEQ ID NO 19
<211> LENGTH: 113
<212> TYPE: PRT
<213> ORGANISM: Murine

<400> SEQUENCE: 19

Glu Leu Val Met Thr Gln Ser Pro Leu Ser Leu Pro Val Ser Leu Gly
1               5                   10                  15

Asp Gln Ala Ser Ile Ser Cys Arg Pro Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Ser Gly Val Pro
        50                  55                  60

Asp Arg Phe Ser Gly Ser Gly Ser Gly Thr Ala Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Tyr Thr Phe Gly Gly Gly Thr Lys Leu Glu Leu Lys
            100                 105                 110

Arg

<210> SEQ ID NO 20
<211> LENGTH: 113
<212> TYPE: PRT
<213> ORGANISM: Murine

<400> SEQUENCE: 20

Asp Val Val Met Thr Gln Ile Pro Leu Ser Leu Pro Val Asn Leu Gly
1               5                   10                  15

Asp Gln Ala Ser Ile Ser Cys Arg Ser Ser Gln Ser Leu Ile His Ser
            20                  25                  30

Asn Gly Asn Thr Tyr Leu His Trp Tyr Leu Gln Lys Pro Gly Gln Ser
        35                  40                  45

Pro Lys Leu Leu Met Tyr Lys Val Ser Asn Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Ser His Val Pro Pro Thr Phe Gly Gly Gly Thr Lys Leu Glu Ile Lys
            100                 105                 110

Arg

<210> SEQ ID NO 21
<211> LENGTH: 108
<212> TYPE: PRT
<213> ORGANISM: Murine

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu His
65                  70                  75                  80

Glu Asp Ile Ala Thr Tyr Phe Cys Gln Gln Gly Ser Thr Leu Pro Arg
                85                  90                  95

Thr Phe Gly Gly Gly Thr Lys Leu Glu Ile Lys Arg
            100                 105

<210> SEQ ID NO 22
<211> LENGTH: 111
<212> TYPE: PRT
<213> ORGANISM: Homo sapiens

<400> SEQUENCE: 22

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Ser Ser
            20                  25                  30

Thr Val Asn Trp Tyr Gln Gln Leu Pro Gly Met Ala Pro Lys Leu Leu
        35                  40                  45

Ile Tyr Arg Asp Ala Met Arg Pro Ser Gly Val Pro Asp Arg Phe Ser

```
            50                  55                  60
Gly Ser Lys Ser Gly Ala Ser Ala Ser Leu Ala Ile Gly Gly Leu Gln
 65                  70                  75                  80

Ser Glu Asp Glu Thr Asp Tyr Tyr Cys Ala Ala Trp Asp Val Ser Leu
                 85                  90                  95

Asn Ala Tyr Val Phe Gly Thr Gly Thr Lys Val Thr Val Leu Gly
                100                 105                 110

<210> SEQ ID NO 23
<211> LENGTH: 107
<212> TYPE: PRT
<213> ORGANISM: Murine

<400> SEQUENCE: 23

Glu Ile Val Leu Thr Gln Ser Pro Ala Ile Thr Ala Ala Ser Leu Gly
  1               5                  10                  15

Gln Lys Val Thr Ile Thr Cys Ser Ala Ser Ser Val Ser Ser Lys
                 20                  25                  30

Asn Trp Tyr Gln Gln Lys Ser Gly Thr Ser Pro Lys Pro Trp Ile Tyr
                 35                  40                  45

Glu Ile Ser Lys Leu Ala Ser Gly Val Pro Ala Arg Phe Ser Gly Ser
 50                  55                  60

Gly Ser Gly Thr Ser Tyr Ser Leu Thr Ile Asn Thr Met Glu Ala Glu
 65                  70                  75                  80

Asp Ala Ala Ile Tyr Tyr Cys Gln Gln Trp Thr Tyr Pro Leu Ile Thr
                 85                  90                  95

Phe Gly Ala Gly Thr Lys Leu Glu Leu Lys Arg
                100                 105

<210> SEQ ID NO 24
<211> LENGTH: 106
<212> TYPE: PRT
<213> ORGANISM: Murine

<400> SEQUENCE: 24

Asp Ile Val Leu Thr Gln Ser Pro Ala Ile Met Ser Ala Ser Pro Gly
  1               5                  10                  15

Glu Lys Val Thr Met Thr Cys Ser Ala Ser Ser Val Asn Tyr Met
                 20                  25                  30

Tyr Trp Tyr Gln Gln Lys Ser Gly Thr Ser Pro Lys Arg Trp Ile Tyr
                 35                  40                  45

Asp Thr Ser Lys Leu Ala Ser Gly Val Pro Val Arg Phe Ser Gly Ser
 50                  55                  60

Gly Ser Gly Thr Ser Tyr Ser Leu Thr Ile Ser Ser Met Glu Thr Glu
 65                  70                  75                  80

Asp Ala Ala Glu Tyr Tyr Cys Gln Gln Trp Gly Thr Asn Pro Thr Phe
                 85                  90                  95

Gly Gly Gly Thr Lys Leu Glu Ile Lys Arg
                100                 105

<210> SEQ ID NO 25
<211> LENGTH: 113
<212> TYPE: PRT
<213> ORGANISM: Murine

<400> SEQUENCE: 25

Asp Val Leu Met Thr Gln Thr Pro Leu Ser Leu Pro Val Ser Leu Gly
  1               5                  10                  15
```

```
Asp Gln Ala Ser Ile Ser Cys Arg Ser Asn Gln Thr Ile Leu Leu Ser
                20                  25                  30

Asp Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
               100                 105                 110

Arg
```

<210> SEQ ID NO 26
<211> LENGTH: 114
<212> TYPE: PRT
<213> ORGANISM: Murine

<400> SEQUENCE: 26

```
Asp Ile Val Met Thr Gln Ser Pro Ser Ser Leu Ser Val Ser Ala Gly
 1               5                  10                  15

Glu Arg Val Thr Met Ser Cys Lys Ser Ser Gln Ser Leu Leu Asn Ser
                20                  25                  30

Gly Asn Gln Lys Asn Phe Leu Ala Trp Tyr Gln Gln Lys Pro Gly Gln
            35                  40                  45

Pro Pro Lys Leu Leu Ile Tyr Gly Ala Ser Thr Arg Glu Ser Glu Val
        50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Ile
               100                 105                 110

Lys Arg
```

<210> SEQ ID NO 27
<211> LENGTH: 108
<212> TYPE: PRT
<213> ORGANISM: Murine

<400> SEQUENCE: 27

```
Asp Ile Val Leu Thr Gln Ser Pro Ala Thr Leu Ser Val Thr Pro Gly
 1               5                  10                  15

Asn Ser Val Ser Leu Ser Cys Arg Ala Ser Gln Ser Ile Gly Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys Arg
```

-continued

```
                100             105

<210> SEQ ID NO 28
<211> LENGTH: 113
<212> TYPE: PRT
<213> ORGANISM: Murine

<400> SEQUENCE: 28

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Gln Gly Asn Thr Tyr Leu Arg Trp Tyr Leu Gln Lys Pro Gly Gln Ser
        35                  40                  45

Pro Lys Val Lys Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Met Tyr Phe Cys Ser Gln Ser
                85                  90                  95

Thr His Val Pro Trp Thr Phe Gly Gly Gly Thr Lys Leu Glu Ile Lys
            100                 105                 110

Arg

<210> SEQ ID NO 29
<211> LENGTH: 107
<212> TYPE: PRT
<213> ORGANISM: Murine

<400> SEQUENCE: 29

Asp Ile Gln Met Thr Gln Ile Pro Ser Ser Leu Ser Ala Ser Leu Gly
 1               5                  10                  15

Asp Arg Val Ser Ile Ser Cys Arg Ala Ser Gln Asp Ile Asn Asn Phe
            20                  25                  30

Leu Asn Trp Tyr Gln Gln Lys Pro Asp Gly Thr Ile Lys Leu Leu Ile
        35                  40                  45

Tyr Phe Thr Ser Arg Ser Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Ala Leu Pro Arg
                85                  90                  95

Thr Phe Gly Gly Thr Lys Leu Glu Ile Lys Arg
            100                 105

<210> SEQ ID NO 30
<211> LENGTH: 105
<212> TYPE: PRT
<213> ORGANISM: Homo sapiens

<400> SEQUENCE: 30

Glu Leu Thr Gln Pro Pro Ser Val Ser Val Ser Pro Gly Gln Thr Ala
 1               5                  10                  15

Arg Ile Thr Cys Ser Ala Asn Ala Leu Pro Asn Gln Tyr Ala Tyr Trp
            20                  25                  30

Tyr Gln Gln Lys Pro Gly Arg Ala Pro Val Met Val Ile Tyr Lys Asp
        35                  40                  45
```

```
Thr Gln Arg Pro Ser Gly Ile Pro Gln Arg Phe Ser Ser Thr Ser
     50                  55                  60

Gly Thr Thr Val Thr Leu Thr Ile Ser Gly Val Gln Ala Glu Asp Glu
 65                  70                  75                  80

Ala Asp Tyr Tyr Cys Gln Ala Trp Asp Asn Ser Ala Ser Ile Phe Gly
                 85                  90                  95

Gly Gly Thr Lys Leu Thr Val Leu Gly
            100                 105

<210> SEQ ID NO 31
<211> LENGTH: 119
<212> TYPE: PRT
<213> ORGANISM: Murine

<400> SEQUENCE: 31

Gln Val Lys Leu Gln Glu Ser Gly Pro Ala Val Ile Lys Pro Ser Gln
 1               5                  10                  15

Ser Leu Ser Leu Thr Cys Ile Val Ser Gly Phe Ser Ile Thr Arg Thr
                 20                  25                  30

Asn Tyr Cys Trp His Trp Ile Arg Pro Gly Lys Gly Leu Glu Trp Met
             35                  40                  45

Gly Arg Ile Cys Tyr Glu Glu Ser Ile Tyr Tyr Ser Pro Ser Ile Lys
         50                  55                  60

Ser Arg Ser Thr Ile Ser Arg Asp Thr Ser Leu Asn Lys Phe Phe Ile
 65                  70                  75                  80

Gln Leu Ile Ser Val Thr Asn Glu Asp Thr Ala Met Tyr Tyr Cys Ser
                 85                  90                  95

Arg Glu Asn His Met Tyr Glu Thr Tyr Phe Asp Val Trp Gly Gln Gly
                100                 105                 110

Thr Thr Val Thr Val Ser Ser
            115

<210> SEQ ID NO 32
<211> LENGTH: 117
<212> TYPE: PRT
<213> ORGANISM: Murine

<400> SEQUENCE: 32

Asp Val Gln Leu Gln Glu Ser Gly Pro Gly Leu Val Lys Pro Ser Gln
 1               5                  10                  15

Ser Gln Ser Gln Ser Leu Thr Cys Thr Val Thr Gly Tyr Ser Ile Thr
                 20                  25                  30

Ser Asp Tyr Ala Trp Asn Trp Ile Arg Gln Phe Pro Gly Asn Lys Leu
             35                  40                  45

Glu Trp Met Gly Tyr Met Ser Tyr Ser Gly Ser Thr Arg Tyr Asn Pro
         50                  55                  60

Ser Leu Arg Ser Arg Ile Ser Ile Thr Arg Asp Thr Ser Lys Asn Gln
 65                  70                  75                  80

Phe Phe Leu Gln Leu Lys Ser Val Thr Thr Glu Asp Thr Ala Thr Tyr
                 85                  90                  95

Phe Cys Ala Arg Gly Trp Pro Leu Ala Tyr Trp Gly Gln Gly Thr Gln
                100                 105                 110

Val Ser Val Ser Glu
            115

<210> SEQ ID NO 33
<211> LENGTH: 115
```

-continued

```
<212> TYPE: PRT
<213> ORGANISM: Murine

<400> SEQUENCE: 33

Val Gln Leu Gln Gln Ser Asp Ala Glu Lys Val Lys Pro Gly Ala Ser
  1               5                  10                  15

Val Lys Ile Ser Cys Lys Ala Ser Gly Tyr Thr Phe Thr Asp His Ala
             20                  25                  30

Ile His Trp Ala Lys Gln Lys Pro Glu Gln Gly Leu Glu Trp Ile Gly
         35                  40                  45

Tyr Ile Ser Pro Gly Asn Asp Asp Ile Lys Tyr Asn Glu Lys Phe Lys
     50                  55                  60

Gly Lys Ala Thr Leu Thr Ala Asp Lys Ser Ser Thr Ala Tyr Met
 65                  70                  75                  80

Gln Leu Asn Ser Leu Thr Ser Glu Asp Ser Ala Val Tyr Phe Cys Lys
                 85                  90                  95

Arg Ser Thr Ala Trp Phe Ala Tyr Trp Gly Gln Gly Thr Leu Val Thr
            100                 105                 110

Val Ser Ser
        115

<210> SEQ ID NO 34
<211> LENGTH: 119
<212> TYPE: PRT
<213> ORGANISM: Murine

<400> SEQUENCE: 34

Glu Val Gln Pro Val Glu Thr Gly Gly Gly Leu Val Gln Pro Lys Gly
  1               5                  10                  15

Ser Leu Lys Leu Ser Cys Ala Ala Ser Gly Phe Ser Phe Asn Thr Asn
             20                  25                  30

Ala Asn Asn Trp Val Arg Gln Ala Pro Gly Lys Gly Leu Glu Trp Val
         35                  40                  45

Ala Arg Ser Lys Ser Asn Asn Tyr Ala Thr Tyr Tyr Ala Asp Ser Val
     50                  55                  60

Lys Asp Arg Phe Thr Ile Ser Arg Asp Asp Ser Gln Asn Met Leu Tyr
 65                  70                  75                  80

Leu Gln Met Asn Asn Leu Lys Thr Glu Asp Thr Ala Met Tyr Tyr Cys
                 85                  90                  95

Val Arg Asp Gln Thr Gly Thr Ala Trp Phe Ala Tyr Trp Gly Gln Gly
            100                 105                 110

Thr Leu Val Thr Val Ser Ala
        115

<210> SEQ ID NO 35
<211> LENGTH: 126
<212> TYPE: PRT
<213> ORGANISM: Homo sapiens

<400> SEQUENCE: 35

Glu Val Gln Leu Val Glu Ser Gly Gly Gly Leu Val Gln Phe Gly Arg
  1               5                  10                  15

Ser Leu Arg Leu Ser Cys Ala Ala Ser Gly Phe Thr Phe Asn Asp Tyr
             20                  25                  30

Ala Met His Trp Val Arg Gln Ala Pro Gly Lys Gly Leu Glu Trp Val
         35                  40                  45

Ser Gly Ile Ser Trp Asp Ser Ser Ile Gly Tyr Ala Asp Ser Val
```

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Met Ala Leu Tyr Tyr Cys
                 85                  90                  95

Val Lys Gly Arg Asp Tyr Tyr Asp Ser Gly Gly Tyr Phe Thr Val Ala
                100                 105                 110

Phe Asp Ile Trp Gly Gln Gly Thr Met Val Thr Val Ser Ser
                115                 120                 125

<210> SEQ ID NO 36
<211> LENGTH: 116
<212> TYPE: PRT
<213> ORGANISM: Murine

<400> SEQUENCE: 36

Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Thr Gly Tyr
                 20                  25                  30

Gly Val Asn Trp Val Arg Gln Pro Pro Gly Lys Gly Leu Glu Trp Leu
                 35                  40                  45

Gly Met Ile Trp Gly Asp Gly Asn Thr Asp Tyr Asn Ser Ala Leu Lys
 50                  55                  60

Ser Arg Leu Ser Ile Ser Lys Asp Asn Ser Lys Ser Gln Val Phe Leu
 65                  70                  75                  80

Lys Met Asn Ser Leu His Thr Asp Asp Thr Ala Arg Tyr Tyr Cys Ala
                 85                  90                  95

Arg Glu Arg Asp Tyr Arg Leu Asp Tyr Trp Gly Gln Gly Thr Thr Leu
                100                 105                 110

Thr Val Ser Ser
        115

<210> SEQ ID NO 37
<211> LENGTH: 119
<212> TYPE: PRT
<213> ORGANISM: Murine

<400> SEQUENCE: 37

Asp Val Gln Leu Gln Gln Ser Gly Pro Glu Leu Glu Lys Pro Gly Ala
  1               5                  10                  15

Ser Val Lys Ile Ser Cys Lys Ala Ser Gly Phe Ser Leu Pro Gly His
                 20                  25                  30

Asn Ile Asn Trp Ile Val Gln Arg Asn Gly Lys Ser Leu Glu Trp Ile
                 35                  40                  45

Gly Asn Ile Asp Pro Tyr Tyr Gly Gly Thr Asn Phe Asn Pro Lys Phe
 50                  55                  60

Lys Gly Lys Ala Thr Leu Thr Val Asp Lys Ser Ser Ser Thr Leu Tyr
 65                  70                  75                  80

Met His Leu Thr Ser Leu Gln Ser Glu Asp Ser Ala Val Tyr Tyr Cys
                 85                  90                  95

Ala Arg Arg Arg Asp Gly Asn Tyr Gly Phe Thr Tyr Trp Gly Gln Gly
                100                 105                 110

Thr Leu Val Thr Val Ser Ala
        115
```

```
<210> SEQ ID NO 38
<211> LENGTH: 120
<212> TYPE: PRT
<213> ORGANISM: Murine

<400> SEQUENCE: 38

Glu Val Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Phe
            20                  25                  30

Gly Met Ser Trp Val Arg His Thr Pro Asp Lys Arg Leu Glu Trp Val
        35                  40                  45

Ala Thr Ile Ser Asn Gly Gly Tyr Thr Tyr Tyr Gln Asp Ser Val
    50                  55                  60

Lys Gly Arg Phe Thr Ile Ser Arg Asp Asn Ala Lys Asn Thr Leu Phe
 65                  70                  75                  80

Leu Glu Met Thr Ser Leu Lys Ser Glu Asp Ala Gly Leu Tyr Tyr Cys
                85                  90                  95

Ala Arg Arg Glu Arg Tyr Asp Glu Lys Gly Phe Ala Tyr Trp Gly Arg
            100                 105                 110

Gly Thr Leu Val Thr Val Ser Ala
        115                 120

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Humanized
      murine

<400> SEQUENCE: 39

Glu Val Gln Leu Val Glu Ser Gly Gly Gly Leu Val Gln Pro Gln Gln
 1               5                  10                  15

Phe Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 40
<211> LENGTH: 115
<212> TYPE: PRT
<213> ORGANISM: Murine

<400> SEQUENCE: 40

Gln Val Gln Leu Gln Glu Ser Gly Pro Gly Ile Leu Gln Pro Ser Gln
 1               5                  10                  15

Ser Leu Ser Leu Thr Cys Ser Phe Ser Gly Phe Ser Leu Ser Thr Tyr
            20                  25                  30
```

```
Gly Met Gly Val Ser Trp Ile Arg Gln Pro Ser Gly Lys Gly Leu Glu
         35                  40                  45

Trp Leu Ala His Ile Phe Trp Asp Gly Asp Lys Arg Tyr Asn Pro Ser
 50                  55                  60

Leu Lys Ser Arg Leu Lys Ile Ser Lys Asp Thr Ser Asn Asn Gln Val
 65                  70                  75                  80

Phe Leu Lys Ile Thr Ser Val Asp Thr Ala Asp Thr Ala Thr Tyr Tyr
                 85                  90                  95

Cys Val Gln Glu Gly Tyr Ile Tyr Trp Gly Gln Gly Thr Ser Val Thr
                100                 105                 110

Val Ser Ser
        115

<210> SEQ ID NO 41
<211> LENGTH: 122
<212> TYPE: PRT
<213> ORGANISM: Murine

<400> SEQUENCE: 41

Gln Val Gln Leu Lys Glu Ser Gly Pro Gly Leu Val Ala Pro Ser Gln
  1               5                  10                  15

Thr Leu Ser Ile Thr Cys Thr Val Ser Gly Phe Leu Leu Ile Ser Asn
                 20                  25                  30

Gly Val His Trp Val Arg Gln Pro Pro Gln Lys Gly Leu Glu Trp Leu
         35                  40                  45

Gly Val Ile Trp Ala Gly Gly Asn Thr Asn Tyr Asn Ser Ala Leu Met
 50                  55                  60

Ser Arg Val Ser Ile Ser Lys Asp Asn Ser Lys Ser Gln Val Phe Leu
 65                  70                  75                  80

Lys Met Lys Ser Leu Gln Thr Asp Asp Thr Ala Met Tyr Tyr Cys Ala
                 85                  90                  95

Arg Asp Phe Tyr Asp Tyr Asp Val Phe Tyr Tyr Ala Met Asp Tyr Trp
                100                 105                 110

Gly Gln Gly Thr Ser Val Thr Val Ser Ser
        115                 120

<210> SEQ ID NO 42
<211> LENGTH: 120
<212> TYPE: PRT
<213> ORGANISM: Murine

<400> SEQUENCE: 42

Glu Val Gln Leu Val Glu Ser Gly Gly Asp Leu Val Lys Pro Gly Gly
  1               5                  10                  15

Ser Leu Lys Leu Ser Cys Ala Ala Ser Gly Phe Ser Phe Ser Ser Tyr
                 20                  25                  30

Gly Met Ser Trp Val Arg Gln Thr Pro Asp Lys Arg Leu Glu Trp Val
         35                  40                  45

Ala Thr Ile Ser Asn Gly Gly Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Ser Ala Met Tyr Tyr Cys
                 85                  90                  95

Ala Arg Arg Glu Arg Tyr Asp Glu Asn Gly Phe Ala Tyr Trp Gly Gln
                100                 105                 110
```

```
Gly Thr Leu Val Thr Val Ser Ala
        115                 120

<210> SEQ ID NO 43
<211> LENGTH: 118
<212> TYPE: PRT
<213> ORGANISM: Murine

<400> SEQUENCE: 43

Val Gln Leu Gln Gln Ser Gly Pro Glu Leu Lys Pro Gly Ala Ser
  1               5                  10                  15

Val Arg Met Ser Cys Lys Ser Gly Tyr Ile Phe Thr Asp Phe Tyr
                20                  25                  30

Met Asn Trp Val Arg Gln Ser His Gly Lys Ser Leu Asp Tyr Ile Gly
            35                  40                  45

Tyr Ile Ser Pro Tyr Ser Gly Val Thr Gly Tyr Asn Gln Lys Phe Lys
        50                  55                  60

Gly Lys Ala Thr Leu Thr Val Asp Lys Ser Ser Ser Thr Ala Tyr Met
 65                  70                  75                  80

Glu Leu Arg Ser Leu Thr Ser Glu Asp Ser Ala Val Tyr Tyr Cys Ala
                85                  90                  95

Gly Ser Ser Gly Asn Lys Trp Ala Met Asp Tyr Trp Gly His Gly Ala
            100                 105                 110

Ser Val Thr Val Ser Ser
        115

<210> SEQ ID NO 44
<211> LENGTH: 114
<212> TYPE: PRT
<213> ORGANISM: Murine

<400> SEQUENCE: 44

Glu Val Thr Leu Val Glu Ser Gly Gly Asp Ser Val Lys Pro Gly Gly
  1               5                  10                  15

Ser Leu Lys Lys Ser Cys Ala Ala Ser Gly Phe Thr Leu Ser Gly Glu
                20                  25                  30

Thr Met Ser Trp Val Arg Gln Thr Pro Glu Lys Arg Leu Glu Trp Val
            35                  40                  45

Ala Thr Thr Leu Ser Gly Gly Gly Phe Thr Phe Tyr Ser Ala Ser Val
        50                  55                  60

Lys Gly Arg Phe Thr Ile Ser Arg Asp Asn Ala Gln Asn Asn Leu Tyr
 65                  70                  75                  80

Leu Gln Leu Asn Ser Leu Arg Ser Glu Asp Thr Ala Leu Tyr Phe Cys
                85                  90                  95

Ala Ser His Arg Phe Val His Trp Gly His Gly Thr Leu Val Thr Val
            100                 105                 110

Ser Ala

<210> SEQ ID NO 45
<211> LENGTH: 118
<212> TYPE: PRT
<213> ORGANISM: Murine

<400> SEQUENCE: 45

Gln Val Gln Leu Gln Gln Ser Gly Pro Glu Leu Val Arg Pro Gly Ser
  1               5                  10                  15

Ser Val Lys Ile Ser Cys Lys Gly Ser Gly Tyr Thr Phe Thr Thr Tyr
```

```
                    20                  25                  30
Ala Met His Trp Val Lys Gln Ser His Ala Lys Ser Leu Glu Trp Ile
            35                  40                  45

Gly Leu Ile Ser Pro Ser Ser Gly Tyr Thr Ser Tyr Asn Gly Glu Phe
        50                  55                  60

Lys Gly Lys Ala Thr Met Thr Val Asp Lys Ser Ser Thr Ala Tyr
 65              70                  75                  80

Met Glu Leu Ala Arg Leu Thr Ser Glu Asp Ser Ala Ile Tyr Tyr Cys
                85                  90                  95

Ala Arg Val Met Gly Glu Gln Tyr Phe Asp Phe Trp Gly Ala Gly Thr
                100                 105                 110

Thr Val Thr Val Ser Ser
            115

<210> SEQ ID NO 46
<211> LENGTH: 119
<212> TYPE: PRT
<213> ORGANISM: Murine

<400> SEQUENCE: 46

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asp Gly Tyr Thr Thr Glu Tyr Ser Ala
        50                  55                  60

Ser Val Lys Gly Arg Phe Thr Ile Ser Arg Asp Asn Ser Gln Ser Ile
 65              70                  75                  80

Leu Tyr Leu Gln Met Asn Thr Leu Arg Ala Glu Asp Ser Ala Thr Tyr
                85                  90                  95

Tyr Cys Thr Arg Asp Pro Tyr Gly Pro Ala Ala Tyr Trp Gly Gln Gly
                100                 105                 110

Thr Leu Val Thr Val Ser Ala
            115

<210> SEQ ID NO 47
<211> LENGTH: 117
<212> TYPE: PRT
<213> ORGANISM: Homo sapiens

<400> SEQUENCE: 47

Pro Leu Val Leu Gln Glu Ser Gly Pro Gly Leu Val Lys Pro Ser Glu
 1               5                  10                  15

Ala Leu Ser Leu Thr Cys Thr Val Ser Gly Asp Ser Ile Asn Thr Ile
                20                  25                  30

Leu Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Tyr Gly Asn Pro Ser
        50                  55                  60

Leu Lys Ser Arg Val Thr Ile Ser Val Asn Thr Ser Lys Asn Gln Phe
 65              70                  75                  80

Tyr Ser Lys Leu Ser Ser Val Thr Ala Ala Asp Thr Ala Val Tyr Tyr
                85                  90                  95

Cys Ala Arg Val Pro Leu Val Val Asn Pro Trp Gly Gln Gly Thr Leu
```

-continued

```
              100                 105                 110
Val Thr Val Ser Ser
        115

<210> SEQ ID NO 48
<211> LENGTH: 120
<212> TYPE: PRT
<213> ORGANISM: Anous Minutus
<220> FEATURE:
<223> OTHER INFORMATION: Noddy Tern

<400> SEQUENCE: 48

Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr Asn Tyr
             20                  25                  30

Gly Met Asn Trp Val Lys Gln Ala Pro Gly Lys Gly Leu Lys Trp Met
         35                  40                  45

Gly Trp Ile Asn Thr Asn Thr Gly Glu Pro Thr Tyr Gly Glu Glu Phe
     50                  55                  60

Lys Gly Arg Phe Ala Phe Ser Leu Glu Thr Ser Ala Ser Thr Ala Asn
 65                  70                  75                  80

Leu Gln Ile Asn Asn Leu Lys Asn Glu Asp Thr Ala Thr Phe Phe Cys
                 85                  90                  95

Ala Arg Gly Glu Asp Asn Phe Gly Ser Leu Ser Asp Tyr Trp Gly Gln
            100                 105                 110

Gly Thr Thr Val Thr Val Ser Ser
        115                 120

<210> SEQ ID NO 49
<211> LENGTH: 116
<212> TYPE: PRT
<213> ORGANISM: Murine

<400> SEQUENCE: 49

Arg Val Gln Leu Leu Glu Ser Gly Ala Glu Leu Met Lys Pro Gly Ala
  1               5                  10                  15

Ser Val Gln Ile Ser Cys Lys Ala Thr Gly Tyr Thr Phe Ser Glu Tyr
             20                  25                  30

Trp Ile Glu Trp Val Lys Glu Arg Pro Gly His Gly Leu Glu Trp Ile
         35                  40                  45

Gly Glu Ile Leu Pro Gly Ser Gly Arg Thr Asn Tyr Arg Glu Lys Phe
     50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gly Tyr Ser Ser Met Asp Tyr Trp Gly Gln Gly Thr Ser Val
            100                 105                 110

Thr Val Ser Ala
        115

<210> SEQ ID NO 50
<211> LENGTH: 119
<212> TYPE: PRT
<213> ORGANISM: Murine

<400> SEQUENCE: 50
```

-continued

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ala Phe Thr Asn Tyr
                20                  25                  30

Gly Val Asn Trp Val Lys Glu Ala Pro Gly Lys Glu Leu Lys Trp Met
            35                  40                  45

Gly Trp Ile Asn Ile Tyr Thr Gly Glu Pro Thr Tyr Val Asp Asp Phe
    50                  55                  60

Lys Gly Arg Phe Ala Phe Ser Leu Glu Thr Ser Ala Ser Thr Ala Tyr
65                  70                  75                  80

Leu Glu Ile Asn Asn Leu Lys Asn Glu Asp Thr Ala Thr Tyr Phe Cys
                85                  90                  95

Thr Arg Gly Asp Tyr Val Asn Trp Tyr Phe Asp Val Trp Gly Ala Gly
                100                 105                 110

Thr Thr Val Thr Val Ser Ser
            115

<210> SEQ ID NO 51
<211> LENGTH: 124
<212> TYPE: PRT
<213> ORGANISM: Murine

<400> SEQUENCE: 51

Gln Val Gln Leu Gln Gln Ser Gly Ala Glu Leu Val Arg Ala Gly Ser
1               5                   10                  15

Ser Val Lys Met Ser Cys Lys Ala Ser Gly Tyr Thr Phe Thr Ser Tyr
                20                  25                  30

Gly Val Asn Trp Val Lys Gln Arg Pro Gly Gln Gly Leu Glu Trp Ile
            35                  40                  45

Gly Tyr Ile Asn Pro Gly Lys Gly Tyr Leu Ser Tyr Asn Glu Lys Phe
    50                  55                  60

Lys Gly Lys Thr Thr Leu Thr Val Asp Arg Ser Ser Ser Thr Ala Tyr
65                  70                  75                  80

Met Gln Leu Arg Ser Leu Thr Ser Glu Asp Ala Ala Val Tyr Phe Cys
                85                  90                  95

Ala Arg Ser Phe Tyr Gly Gly Ser Asp Leu Ala Val Tyr Tyr Phe Asp
                100                 105                 110

Ser Trp Gly Gln Gly Thr Thr Leu Thr Val Ser Ser
            115                 120

<210> SEQ ID NO 52
<211> LENGTH: 126
<212> TYPE: PRT
<213> ORGANISM: Homo sapiens

<400> SEQUENCE: 52

Glu Val Gln Leu Val Gln Ser Gly Gly Val Val Gln Pro Gly Arg
1               5                   10                  15

Ser Leu Arg Leu Ser Cys Ser Ser Gly Phe Ile Phe Ser Ser Tyr
                20                  25                  30

Ala Met Tyr Trp Val Arg Gln Ala Pro Gly Lys Gly Leu Glu Trp Val
            35                  40                  45

Ala Ile Ile Trp Asp Asp Gly Ser Asp Gln His Tyr Ala Asp Ser Val
    50                  55                  60

Lys Gly Arg Phe Thr Ile Ser Arg Asn Asp Ser Lys Asn Ser Leu Phe
65                  70                  75                  80

```
Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
            100                 105                 110

Pro Asp Tyr Trp Gly Gln Gly Thr Pro Val Thr Val Ser Ser
        115                 120                 125

<210> SEQ ID NO 53
<211> LENGTH: 118
<212> TYPE: PRT
<213> ORGANISM: Murine

<400> SEQUENCE: 53

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Lys Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Gly Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Leu His Tyr Tyr Gly Tyr Asn Ala Tyr Trp Gly Gln Gly Thr
            100                 105                 110

Leu Val Thr Val Ser Ala
        115

<210> SEQ ID NO 54
<211> LENGTH: 115
<212> TYPE: PRT
<213> ORGANISM: Murine

<400> SEQUENCE: 54

Val Gln Leu Gln Gln Ser Gly Ala Glu Leu Met Lys Pro Gly Ala Ser
1               5                   10                  15

Val Lys Ile Ser Cys Lys Ala Ser Gly Tyr Thr Phe Ser Asp Tyr Trp
            20                  25                  30

Ile Glu Trp Val Lys Gln Arg Pro Gly His Gly Leu Glu Trp Ile Gly
        35                  40                  45

Glu Ile Leu Pro Gly Ser Gly Ser Thr Asn Tyr His Glu Arg Phe Lys
    50                  55                  60

Gly Lys Ala Thr Phe Thr Ala Asp Thr Ser Ser Ser Thr Ala Tyr Met
65                  70                  75                  80

Gln Leu Asn Ser Leu Thr Ser Glu Asp Ser Ala Val Tyr Tyr Cys Leu
                85                  90                  95

His Gly Asn Tyr Asp Phe Asp Gly Trp Gly Gln Gly Thr Thr Leu Thr
            100                 105                 110

Val Ser Ser
        115

<210> SEQ ID NO 55
<211> LENGTH: 119
<212> TYPE: PRT
<213> ORGANISM: Murine
```

```
<400> SEQUENCE: 55

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Arg Cys
            20                  25                  30

Ala Met Ser Trp Val Arg Gln Thr Pro Glu Lys Arg Leu Glu Trp Val
        35                  40                  45

Ala Gly Ile Ser Ser Gly Gly Ser Tyr Thr Phe Tyr Pro Asp Thr Val
    50                  55                  60

Lys Gly Arg Phe Ile Ile Ser Arg Asn Asn Ala Arg Asn Thr Leu Ser
65                  70                  75                  80

Leu Gln Met Ser Ser Leu Arg Ser Glu Asp Thr Ala Ile Tyr Tyr Cys
                85                  90                  95

Thr Arg Tyr Ser Ser Asp Pro Phe Tyr Phe Asp Tyr Trp Gly Gln Gly
            100                 105                 110

Thr Thr Leu Thr Val Ser Ser
        115

<210> SEQ ID NO 56
<211> LENGTH: 122
<212> TYPE: PRT
<213> ORGANISM: Murine

<400> SEQUENCE: 56

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Gly Asn Lys Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asn Tyr Tyr Gly Ser Thr Trp Tyr Phe Asp Val Trp
            100                 105                 110

Gly Ala Gly Thr Thr Val Thr Val Ser Ser
        115                 120

<210> SEQ ID NO 57
<211> LENGTH: 113
<212> TYPE: PRT
<213> ORGANISM: Murine

<400> SEQUENCE: 57

Asp Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Asp
            20                  25                  30

Tyr Trp Ser Trp Ile Arg Lys Phe Pro Gly Asn Arg Leu Glu Tyr Met
        35                  40                  45

Gly Tyr Val Ser Tyr Ser Gly Ser Thr Tyr Tyr Asn Pro Ser Leu Lys
    50                  55                  60
```

```
Ser Arg Ile Ser Ile Thr Arg Asp Thr Ser Lys Asn Gln Tyr Tyr Leu
 65                  70                  75                  80

Asp Leu Asn Ser Val Thr Thr Glu Asp Thr Ala Thr Tyr Tyr Cys Ala
                 85                  90                  95

Asn Trp Asp Gly Asp Tyr Trp Gly Gln Gly Thr Leu Val Thr Val Ser
            100                 105                 110

Ala

<210> SEQ ID NO 58
<211> LENGTH: 118
<212> TYPE: PRT
<213> ORGANISM: Murine

<400> SEQUENCE: 58

Glu Val Gln Leu Asp Glu Thr Gly Gly Gly Leu Val Gln Pro Gly Arg
 1               5                  10                  15

Pro Met Lys Leu Ser Cys Val Ala Ser Gly Phe Thr Phe Ser Asp Tyr
                 20                  25                  30

Trp Met Asn Trp Val Arg Gln Ser Pro Glu Lys Gly Leu Glu Trp Val
             35                  40                  45

Ala Gln Ile Arg Asn Lys Pro Tyr Asn Tyr Glu Thr Tyr Tyr Ser Asp
         50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Gly Met Asp Tyr Trp Gly Gln Gly Thr
            100                 105                 110

Ser Val Thr Val Ser Ser
        115
```

```
<210> SEQ ID NO 59
<211> LENGTH: 121
<212> TYPE: PRT
<213> ORGANISM: Murine

<400> SEQUENCE: 59

Glu Val Gln Leu Gln Gln Ser Gly Val Glu Leu Val Arg Ala Gly Ser
 1               5                  10                  15

Ser Val Lys Met Ser Cys Lys Ala Ser Gly Tyr Thr Phe Thr Ser Asn
                 20                  25                  30

Gly Ile Asn Trp Val Lys Gln Arg Pro Gly Gln Gly Leu Glu Trp Ile
             35                  40                  45

Gly Tyr Asn Asn Pro Gly Asn Gly Tyr Ile Ala Tyr Asn Glu Lys Phe
         50                  55                  60

Lys Gly Lys Thr Thr Leu Thr Val Asp Lys Ser Ser Ser Thr Ala Tyr
 65                  70                  75                  80

Met Gln Leu Arg Ser Leu Thr Ser Glu Asp Ser Ala Val Tyr Phe Cys
                 85                  90                  95
```

Ala Arg Ser Glu Tyr Tyr Gly Gly Ser Tyr Lys Phe Asp Tyr Trp Gly
                100                 105                 110

Gln Gly Thr Thr Leu Thr Val Ser Ser
            115                 120

<210> SEQ ID NO 60
<211> LENGTH: 121
<212> TYPE: PRT
<213> ORGANISM: Homo sapiens

<400> SEQUENCE: 60

Ala Val Gln Leu Val Gln Ala Gly Gly Val Val Gln Pro Gly Arg
 1               5                  10                  15

Ser Leu Arg Leu Ser Cys Ile Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asn Gly Ser Arg Thr Tyr Tyr Gly Asp Ser Val
    50                  55                  60

Lys Gly Arg Phe Thr Ile Ser Arg Asp Asn Ser Lys Arg Thr Leu Tyr
65                  70                  75                  80

Met Gln Met Asn Ser Leu Arg Thr Glu Asp Thr Ala Val Tyr Tyr Cys
                85                  90                  95

Ala Arg Asp Pro Asp Ile Leu Thr Ala Phe Ser Phe Asp Tyr Trp Gly
                100                 105                 110

Gln Gly Val Leu Val Thr Val Ser Ser
            115                 120

TABLE 1

Sequence variability of residues contributing to the v/c interface

| Position | L9 | | | L10 | | | L12 | | | L15 | | | L39 | | | L40 | | | L41 | | | L80 | | |
|---|---|---|---|---|---|---|---|---|---|---|---|---|---|---|---|---|---|---|---|---|---|---|---|---|
| % exp. (FAB) | 91 | | | 59 | | | 41 | | | 48 | | | 37 | | | 64 | | | 114 | | | 57 | | |
| % exp. (ind.) | 91 | | | 65 | | | 47 | | | 49 | | | 37 | | | 82 | | | 121 | | | 74 | | |
| % buried v/c | 0 | | | 10 | | | 12 | | | 0 | | | 1 | | | 22 | | | 3 | | | 21 | | |
| Species | kappa | lambda | | kappa | | | kappa | lambda | | kappa | lambda | | kappa | lambda | | kappa | lambda | | kappa | lambda | | kappa | lambda | |
| | hu mu | hu mu | | hu mu | | | hu mu | hu mu | | hu mu | hu mu | | hu mu | hu mu | | hu mu | hu mu | | hu mu | hu mu | | hu mu | hu mu | |
| Seq. 4-4-20 | Leu | | | Ser | | | Pro | | | Leu | | | Lys | | | Pro | | | Gly | | | Ala | | |
| Consensus | Ser Ala | Ser Ala | | Thr Ser | | | Ser Ser | Pro Ser | | Leu Pro | Leu Pro | | Lys Lys | Lys Lys | | Pro Pro | Pro Pro | | Gly Gly | Gly Gly | | Pro Ala | Ala Thr | |

Distribution:

| | | | | | | | | | | | | | | | | | | | | | | | | |
|---|---|---|---|---|---|---|---|---|---|---|---|---|---|---|---|---|---|---|---|---|---|---|---|---|
| Asp | 8 | 0 | 4 | 0 | 0 | 0 | 0 | 0 | 15 | 0 | 0 | 0 | 0 | 0 | 0 | 0 | 0 | 0 | 0 | 10 | 3 | 0 | 0 | 0 |
| Glu | 0 | 0 | 69 | 82 | 0 | 0 | 0 | 0 | 68 | 0 | 0 | 0 | 0 | 0 | 0 | 0 | 0 | 0 | 0 | 4 | 0 | 8 | 0 | 0 |
| Lys | 0 | 0 | 0 | 0 | 0 | 0 | 0 | 0 | 0 | 0 | 0 | 0 | 83 | 92 | 0 | 0 | 0 | 0 | 0 | 1 | 0 | 0 | 0 | 0 |
| Arg | 0 | 6 | 0 | 0 | 0 | 0 | 0 | 0 | 0 | 0 | 0 | 0 | 14 | 7 | 0 | 0 | 0 | 0 | 0 | 2 | 2 | 0 | 0 | 0 |
| His | 0 | 4 | 0 | 0 | 0 | 0 | 0 | 0 | 0 | 0 | 0 | 0 | 1 | 0 | 0 | 0 | 1 | 0 | 0 | 1 | 3 | 0 | 0 | 0 |
| Thr | 0 | 0 | 0 | 0 | 49 | 6 | 0 | 3 | 0 | 0 | 0 | 0 | 1 | 0 | 0 | 2 | 1 | 0 | 1 | 1 | 0 | 3 | 0 | 94 |
| Ser | 43 | 24 | 90 | 4 | 48 | 60 | 84 | 50 | 0 | 0 | 1 | 0 | 1 | 0 | 0 | 19 | 5 | 0 | 2 | 1 | 0 | 6 | 17 | 0 |
| Asn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 19 | 0 |
| Gly | 25 | 1 | 0 | 0 | 0 | 0 | 0 | 0 | 0 | 0 | 0 | 0 | 0 | 0 | 0 | 0 | 3 | 0 | 99 | 80 | 90 | 0 | 0 | 0 |
| Ala | 11 | 41 | 7 | 90 | 0 | 0 | 4 | 23 | 0 | 0 | 8 | 1 | 0 | 1 | 0 | 0 | 0 | 0 | 0 | 0 | 2 | 16 | 0 | 56 |
| Cys | 0 | 0 | 0 | 0 | 0 | 0 | 0 | 0 | 0 | 0 | 28 | 0 | 0 | 0 | 0 | 45 | 3 | 0 | 0 | 0 | 0 | 0 | 0 | 4 |
| Pro | 0 | 2 | 0 | 0 | 0 | 0 | 11 | 20 | 0 | 0 | 10 | 1 | 0 | 3 | 0 | 41 | 77 | 92 | 0 | 0 | 0 | 74 | 9 | 0 |
| Val | 1 | 0 | 2 | 1 | 0 | 0 | 0 | 0 | 0 | 0 | 2 | 0 | 0 | 0 | 0 | 1 | 0 | 0 | 0 | 0 | 0 | 0 | 2 | 1 |
| Ile | 0 | 0 | 1 | 3 | 24 | 0 | 0 | 0 | 0 | 0 | 49 | 14 | 0 | 0 | 0 | 0 | 0 | 0 | 0 | 0 | 0 | 0 | 5 | 0 |
| Leu | 11 | 19 | 0 | 0 | 2 | 2 | 0 | 0 | 0 | 0 | 1 | 0 | 0 | 24 | 0 | 4 | 0 | 0 | 0 | 0 | 0 | 0 | 0 | 0 |
| Met | 0 | 0 | 0 | 0 | 2 | 7 | 0 | 0 | 0 | 0 | 0 | 0 | 0 | 3 | 0 | 0 | 3 | 0 | 0 | 0 | 0 | 0 | 0 | 0 |
| Phe | 0 | 1 | 0 | 0 | 0 | 0 | 0 | 0 | 0 | 0 | 0 | 0 | 0 | 2 | 0 | 0 | 0 | 0 | 0 | 2 | 0 | 2 | 0 | 0 |
| Tyr | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| Trp | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| Position | L81 | | | L83 | | | L103 | | | L105 | | | L106 | | | L106A | | | L107 | | | L108 | | |
|---|---|---|---|---|---|---|---|---|---|---|---|---|---|---|---|---|---|---|---|---|---|---|---|---|
| % exp. (FAB) | 70 | | | 17 | | | 42 | | | 19 | | | 14 | | | 56 | | | 56 | | | 47 | | |
| % exp. (ind.) | 74 | | | 38 | | | 58 | | | 57 | | | 28 | | | 65 | | | 65 | | | 103 | | |
| % buried v/c | 5 | | | 46 | | | 26 | | | 66 | | | 56 | | | 15 | | | 15 | | | 55 | | |
| Species | kappa | lambda | | kappa | lambda | | kappa | lambda | | kappa | lambda | | kappa | lambda | | kappa | lambda | | kappa | lambda | | kappa | lambda | |
| | hu mu | hu mu | | hu mu | hu mu | | hu mu | hu mu | | hu mu | hu mu | | hu mu | hu mu | | hu mu | hu mu | | hu mu | hu mu | | hu mu | hu mu | |
| Seq. 4-4-20 | Glu | | | Leu | | | Lys | | | Glu | | | Ile | | | Leu | | | Lys | | | Arg | | |
| Consensus | Glu Glu | Glu Glu | | Leu Glu | Leu Glu | | Lys Lys | Lys Lys | | Glu Thr | Glu Thr | | Ile Ile | Ile Val | | Val Val | Leu Leu | | Lys Lys | Gly Gly | | Arg Arg | Arg Gln | |

Distribution:

| | | | | | | | | | | | | | | | | | | | | | | | | |
|---|---|---|---|---|---|---|---|---|---|---|---|---|---|---|---|---|---|---|---|---|---|---|---|---|
| Asp | 10 | 7 | 0 | 0 | 0 | 0 | 0 | 0 | 0 | 2 | 0 | 0 | 0 | 0 | 0 | 0 | 0 | 0 | 0 | 0 | 0 | 0 | 0 | 0 |
| Glu | 86 | 93 | 0 | 0 | 0 | 0 | 0 | 0 | 0 | 2 | 0 | 0 | 12 | 84 | 0 | 0 | 0 | 0 | 0 | 0 | 0 | 0 | 0 | 0 |
| Lys | 0 | 0 | 0 | 0 | 0 | 99 | 0 | 0 | 98 | 1 | 83 | 6 | 0 | 0 | 100 | 0 | 0 | 0 | 0 | 0 | 94 | 97 | 1 | 0 |
| Arg | 0 | 0 | 0 | 0 | 88 | 0 | 0 | 0 | 1 | 0 | 6 | 2 | 0 | 0 | 0 | 0 | 0 | 0 | 0 | 1 | 2 | 1 | 8 | 3 |
| His | 0 | 0 | 0 | 0 | 8 | 0 | 0 | 0 | 0 | 0 | 0 | 0 | 0 | 1 | 0 | 0 | 0 | 0 | 0 | 0 | 0 | 0 | 0 | 0 |
| Thr | 0 | 0 | 0 | 0 | 2 | 0 | 3 | 0 | 0 | 99 | 2 | 0 | 0 | 0 | 0 | 0 | 0 | 0 | 0 | 0 | 1 | 0 | 0 | 6 |

TABLE 1-continued

Sequence variability of residues contributing to the v/c interface

| Position | H9 | H10 | H11 | H13 | H14 | H41 | H42 | H43 | H84 | H87 | H89 | H105 | H108 | H110 | H112 | H113 |
|---|---|---|---|---|---|---|---|---|---|---|---|---|---|---|---|---|
| % exp. (FAB) | 29 | 65 | 31 | 69 | 36 | 72 | 111 | 65 | 76 | 28 | 34 | 72 | 52 | 26 | 25 | 72 |
| % exp. (ind.) | 33 | 72 | 71 | 73 | 36 | 72 | 115 | 78 | 77 | 31 | 37 | 82 | 64 | 55 | 68 | 78 |
| % buried v/c | 7 | 8 | 58 | 5 | 0 | 0 | 3 | 2 | 2 | 8 | 1 | 1 | 18 | 52 | 62 | 7 |
| Species | hu mu | hu mu | hu mu | hu mu | hu mu | hu mu | hu mu | hu mu | hu mu | hu mu | hu mu | hu mu | hu mu | hu mu | hu mu | hu mu |
| Seq. 4-4-20 | Gly Pro | Gly Glu | Leu Leu | Gln Lys | Pro Pro | Pro Arg | Glu Pro | Lys Gly | Val Ser | Met Thr | Ile Val | Gln Gln | Ser Thr | Thr Thr | Ser Ser | Ser Ser |
| Consensus | Gly Gly | Gly Glu | Leu Leu | Lys Lys | Pro Pro | Ala Arg | Pro Pro | Gly Gly | Ala Ser | Thr Thr | Val Val | Gln Gln | Leu Thr | Thr Thr | Ser Ser | Ser Ser |

Distribution:

| | | | | | | | | | | | | | | | | |
|---|---|---|---|---|---|---|---|---|---|---|---|---|---|---|---|---|
| Asp | 0 0 | 5 2 | 0 0 | 0 0 | 0 0 | 0 0 | 0 0 | 0 2 | 1 0 | 0 0 | 0 0 | 0 1 | 0 0 | 0 0 | 0 0 | 0 0 |
| Glu | 2 0 | 27 54 | 0 0 | 2 0 | 0 0 | 0 0 | 0 0 | 1 19 | 0 0 | 0 0 | 0 1 | 1 0 | 1 0 | 0 0 | 0 0 | 0 0 |
| Lys | 0 0 | 0 0 | 0 0 | 59 54 | 0 0 | 3 0 | 0 0 | 0 1 | 0 0 | 0 0 | 0 1 | 10 0 | 1 0 | 0 0 | 0 0 | 0 0 |
| Arg | 0 0 | 1 0 | 0 0 | 3 18 | 0 0 | 36 0 | 1 0 | 0 0 | 0 0 | 0 0 | 0 0 | 5 1 | 3 0 | 0 0 | 0 0 | 0 0 |
| His | 0 0 | 0 1 | 0 0 | 1 0 | 0 0 | 0 1 | 0 0 | 0 0 | 0 0 | 0 0 | 0 4 | 1 0 | 0 0 | 0 0 | 0 0 | 0 0 |
| Thr | 1 2 | 1 0 | 0 0 | 0 0 | 0 0 | 13 0 | 1 11 | 8 0 | 4 12 | 96 46 | 4 15 | 0 4 | 23 0 | 89 2 | 0 0 | 0 0 |
| Ser | 1 1 | 0 2 | 0 0 | 0 0 | 0 0 | 18 2 | 2 1 | 0 0 | 18 70 | 2 51 | 0 0 | 0 0 | 0 51 | 2 99 | 98 100 | 97 77 |
| Asn | 0 0 | 0 0 | 0 1 | 0 0 | 0 0 | 0 10 | 0 3 | 0 0 | 0 3 | 0 1 | 0 0 | 0 0 | 1 23 | 0 0 | 0 0 | 0 0 |
| Gln | 0 0 | 0 2 | 20 6 | 34 22 | 0 0 | 0 0 | 0 1 | 0 0 | 0 0 | 0 0 | 0 0 | 80 83 | 0 0 | 0 0 | 0 0 | 0 1 |
| Gly | 42 29 | 61 38 | 0 1 | 0 0 | 0 1 | 0 0 | 0 0 | 90 76 | 0 12 | 1 0 | 2 0 | 0 11 | 1 0 | 0 0 | 0 0 | 0 22 |
| Ala | 33 31 | 3 1 | 6 32 | 0 5 | 0 8 | 59 0 | 7 1 | 1 2 | 55 0 | 0 1 | 0 0 | 2 0 | 0 25 | 0 0 | 0 0 | 0 0 |
| Cys | 0 0 | 0 0 | 1 2 | 0 0 | 0 0 | 0 7 | 1 2 | 0 0 | 0 0 | 0 0 | 0 1 | 0 0 | 0 0 | 0 0 | 0 0 | 0 0 |
| Pro | 21 36 | 0 0 | 0 7 | 0 0 | 96 85 | 18 14 | 94 83 | 0 0 | 14 4 | 0 1 | 0 1 | 0 0 | 0 0 | 0 0 | 0 0 | 0 0 |
| Val | 0 1 | 0 0 | 0 0 | 0 0 | 0 0 | 1 1 | 1 0 | 1 0 | 4 1 | 0 0 | 76 50 | 2 0 | 1 1 | 0 1 | 1 0 | 2 0 |
| Ile | 0 0 | 0 0 | 38 1 | 0 0 | 0 0 | 1 1 | 0 0 | 0 0 | 1 0 | 0 0 | 5 13 | 0 0 | 0 0 | 0 7 | 1 0 | 0 0 |
| Leu | 0 0 | 0 0 | 60 95 | 0 0 | 0 3 | 0 7 | 0 0 | 0 0 | 1 0 | 0 0 | 6 7 | 0 0 | 63 0 | 0 0 | 0 0 | 0 0 |
| Met | 0 0 | 0 0 | 0 2 | 0 0 | 0 0 | 1 0 | 0 0 | 0 0 | 7 0 | 0 0 | 7 13 | 0 0 | 9 0 | 0 0 | 0 0 | 0 0 |
| Phe | 0 0 | 0 0 | 0 0 | 0 0 | 0 0 | 0 6 | 0 0 | 0 0 | 2 0 | 1 0 | 0 0 | 0 0 | 0 0 | 0 0 | 0 0 | 0 0 |
| Tyr | 0 0 | 0 0 | 0 0 | 0 0 | 0 0 | 0 0 | 0 0 | 0 0 | 0 0 | 0 0 | 0 0 | 0 0 | 0 0 | 0 0 | 0 0 | 0 0 |
| Trp | 0 0 | 0 0 | 0 0 | 0 0 | 0 0 | 0 0 | 0 0 | 0 0 | 0 0 | 0 0 | 0 0 | 0 0 | 0 0 | 0 0 | 0 0 | 0 0 |
| Ser | 0 0 | 0 0 | 2 0 | 0 0 | 0 0 | 4 0 | 0 0 | 0 1 | 0 0 | 0 0 | 0 2 | 0 0 | 1 0 | 5 0 | 0 0 | 0 0 |
| Asn | 0 0 | 0 1 | 0 0 | 0 0 | 0 0 | 2 0 | 0 0 | 0 0 | 0 0 | 0 1 | 0 0 | 2 0 | 1 0 | 0 0 | 0 0 | 0 0 |
| Gln | 0 0 | 1 17 | 0 0 | 0 0 | 0 0 | 4 2 | 0 0 | 0 0 | 0 0 | 0 0 | 0 0 | 0 0 | 0 0 | 0 0 | 0 0 | 54 0 |
| Gly | 1 0 | 0 0 | 0 31 | 0 0 | 0 0 | 0 0 | 0 0 | 0 0 | 0 0 | 0 0 | 0 0 | 0 0 | 0 0 | 0 92 | 0 0 | 0 0 |
| Ala | 0 0 | 0 0 | 0 0 | 0 0 | 0 0 | 0 0 | 0 0 | 0 0 | 0 0 | 0 0 | 0 0 | 0 0 | 83 0 | 0 0 | 0 0 | 0 0 |
| Cys | 0 0 | 0 0 | 0 0 | 0 0 | 0 0 | 0 0 | 0 0 | 0 0 | 0 0 | 0 0 | 0 0 | 0 0 | 0 1 | 0 0 | 0 0 | 0 0 |
| Pro | 0 0 | 0 1 | 0 0 | 0 0 | 0 0 | 0 0 | 0 0 | 0 0 | 0 0 | 0 0 | 0 0 | 0 0 | 0 0 | 0 0 | 0 0 | 0 6 |
| Val | 0 0 | 0 0 | 20 12 | 0 0 | 0 0 | 3 0 | 0 1 | 0 0 | 3 0 | 0 0 | 2 0 | 0 2 | 0 0 | 0 0 | 0 0 | 0 0 |
| Ile | 0 0 | 0 0 | 6 11 | 0 0 | 0 0 | 1 0 | 0 0 | 1 0 | 88 0 | 0 0 | 97 0 | 97 0 | 0 3 | 0 0 | 0 0 | 0 0 |
| Leu | 0 0 | 0 0 | 1 32 | 0 0 | 0 0 | 0 0 | 100 0 | 3 0 | 1 0 | 73 0 | 0 0 | 0 0 | 0 0 | 0 0 | 0 0 | 0 0 |
| Met | 0 0 | 6 0 | 0 2 | 0 0 | 0 0 | 0 0 | 0 0 | 2 0 | 3 0 | 25 0 | 0 0 | 0 0 | 3 0 | 0 0 | 0 0 | 0 0 |
| Phe | 0 0 | 0 0 | 72 7 | 0 0 | 0 0 | 0 0 | 0 0 | 0 0 | 0 0 | 0 0 | 0 0 | 0 0 | 0 0 | 0 0 | 0 0 | 0 0 |
| Tyr | 0 0 | 0 0 | 0 0 | 0 0 | 0 0 | 0 0 | 0 0 | 0 0 | 0 0 | 0 0 | 0 0 | 0 0 | 0 1 | 0 0 | 0 0 | 0 0 |
| Trp | 0 0 | 0 0 | 0 0 | 0 0 | 0 0 | 0 0 | 0 0 | 0 0 | 0 0 | 0 0 | 0 0 | 0 0 | 0 0 | 0 0 | 0 0 | 0 0 |

TABLE 2

| | Mutations introduced in the scFv fragment of the antibody 4-4-20 | | | |
|---|---|---|---|---|
| | L15E ($V_L$) | L11N ($V_H$) | L11D ($V_H$) | V84D ($V_H$) |
| Flu 1 | ● | | | |
| Flu 2 | | ● | | |
| Flu 3 | | | ● | |
| Flu 4 | | | | ● |
| Flu 5 | | ● | | ● |
| Flu 6 | | | ● | ● |
| Flu 7 | ● | ● | | |
| Flu 8 | ● | | ● | |
| Flu 9 | ● | ● | | ● |
| Flu 4 short | | | | ● |

TABLE 3

| | $K_D$ values of the different scFv mutants determined in fluorescence titration | | | | |
|---|---|---|---|---|---|
| | Flu wt | Flu 3 | Flu 4 | Flu 6 | Flu wt # |
| $K_D$ (nM) | 80 ± 7 | 60 ± 12 | 70 ± 10 | 75 ± 13 | 90 |

What is claimed is:

1. A nucleic acid sequence encoding a modified single chain Fv molecule, wherein said single chain Fv molecule comprises a heavy chain variable domain and a light chain variable domain that interact to form an antigen binding site, wherein said heavy chain variable domain comprises an intra-heavy chain inter-domain interface region and said light chain variable domain comprises an intra-light chain inter-domain interface region and wherein at least one amino acid in an intrachain inter-domain interface region is modified so as to decrease the hydrophobicity in said intra-chain inter-domain interface region.

2. A nucleic acid sequence encoding a modified polypeptide comprising a heavy chain variable domain, wherein said heavy chain variable domain comprises an intra-heavy chain inter-domain interface region, and wherein at least one aznino acid in said intra-heavy chain inter-domain interface region is modified so as to decrease the hydrophobicity in said region.

3. The nucleic acid sequence according to claim 2, wherein said intra-heavy chain inter-domain interface comprises residues 9, 10, 11, 13, 14, 41, 42, 43, 84, 87, 89, 105, 108, 110, 112, 113 of said heavy chain variable domain.

4. A nucleic acid sequence encoding a modified polypeptide comprising a light chain variable domain, wherein said light chain variable domain comprises an intra-light chain inter-domain interface region, and wherein at least one amino acid in said intra-light chain inter-domain interface region is modified so as to decrease the hydrophobicity in said region.

5. The nucleic acid sequence according to claim 4, wherein said inter-domain interface comprises residues 9, 10, 12, 15, 39, 40, 41, 80, 81, 83, 103, 105, 106, 106A, 107, 108 of said light chain variable domain.

6. The nucleic acid sequence according to claim 1 in which said modification comprises insertion of one or more hydrophilic amino acids or deletion of one or more hydrophobic amino acids.

7. The nucleic acid sequence according to claim 1 which said modification comprises any two or more of:

a) a substitution of one or more amino acids with amino acids which are more hydrophilic than the one or more amino acids being substituted for;

b) an insertion of one or more hydrophilic amino acids; and c) a deletion of one or more hydrophobic amino acids.

8. The nucleic acid sequence according to claim 6 or 7 in which said substituted or inserted amino acid is selected from the group consisting of Asn, Asp, Arg, Gln, Glu, Gly, His, Lys, Ser, and Thr.

9. The nucleic acid sequence according to claim 2, 3 or 5, further comprising a contiguous sequence which encodes one or more additional moieties.

10. The nucleic acid sequence according to claim 9 in which at least one of said additional moieties is a toxin, a cytokine, or a reporter enzyme.

11. The nucleic acid sequence according to claim 10 in which at least one of said additional moieties is at least part of a surface protein of an organism.

12. The nucleic acid sequence according to claim 11 in which said organism is a filamentous bacteriophage.

13. The nucleic acid sequence according to claim 12 which said surface protein is the geneIII protein.

14. The nucleic acid sequence according to claim 9 in which at least one of said additional moieties is capable of binding a metal ion.

15. The nucleic acid sequence according to claim 14 in which at least one of said additional moieties comprises at least five hisitidines.

16. The nucleic acid sequence according to claim 9 in which said additional moiety is a labeling tag peptide.

17. The nucleic acid sequence according to claim 16 in which said labeling tag peptide is c-myc or FLAG.

18. The nucleic acid sequence according to claim 9 in which said additional moiety comprises a peptic comprising an association domain.

19. The nucleicacid sequence according to claim 18 in which said association domain comprises a leucine zipper or a helix-turn-helix motif.

20. A vector comprising a nucleic acid sequence according to claim 1, 2 or 3.

21. A host cell comprising a vector according to claim 20.

22. The nucleic acid sequence according to claim 1, wherein at least one amino acid in said intra-heavy chain inter-domain interface and at least one amino acid in said intra-light chain inter-domain interface is modified.

* * * * *